US008664207B2

(12) United States Patent
Li et al.

(10) Patent No.: US 8,664,207 B2
(45) Date of Patent: Mar. 4, 2014

(54) ORGANIC COMPOUNDS

(75) Inventors: Peng Li, New York, NY (US); Jun Zhao, New York, NY (US); Hailin Zheng, New York, NY (US); Lawrence Wennogle, New York, NY (US)

(73) Assignee: Intra-Cellular Therapies, Inc., New York, NY (US)

( * ) Notice: Subject to any disclaimer, the term of this patent is extended or adjusted under 35 U.S.C. 154(b) by 132 days.

(21) Appl. No.: 13/133,101

(22) PCT Filed: Dec. 7, 2009

(86) PCT No.: PCT/US2009/006438
§ 371 (c)(1),
(2), (4) Date: Jun. 6, 2011

(87) PCT Pub. No.: WO2010/065148
PCT Pub. Date: Jun. 10, 2010

(65) Prior Publication Data
US 2011/0237561 A1    Sep. 29, 2011

Related U.S. Application Data

(60) Provisional application No. 61/120,440, filed on Dec. 6, 2008.

(51) Int. Cl.
*A61K 31/565* (2006.01)
*A61K 31/57* (2006.01)
*A61K 31/519* (2006.01)
*C07D 471/14* (2006.01)

(52) U.S. Cl.
USPC .......................... 514/171; 514/267; 544/251

(58) Field of Classification Search
USPC .................. 514/171, 267; 544/251
See application file for complete search history.

(56) References Cited

U.S. PATENT DOCUMENTS

| | | | |
|---|---|---|---|
| 5,202,328 | A | 4/1993 | De Laszlo et al. |
| 5,294,612 | A | 3/1994 | Bacon et al. |
| 5,393,755 | A | 2/1995 | Neustadt et al. |
| 5,824,683 | A | 10/1998 | McKittrick et al. |
| 5,939,419 | A | 8/1999 | Tulshlan |
| 6,013,621 | A | 1/2000 | Nishi et al. |
| 6,133,273 | A | 10/2000 | Gilbert et al. |
| 6,235,742 | B1 | 5/2001 | Bell et al. |
| 6,492,371 | B2 | 12/2002 | Roylance |
| 6,756,373 | B1 | 6/2004 | Allerton et al. |
| 6,969,719 | B2 | 11/2005 | Asberom et al. |
| 7,153,824 | B2 | 12/2006 | Palmer et al. |
| 7,157,451 | B2 | 1/2007 | Atwal et al. |
| 8,273,750 | B2 | 9/2012 | Li et al. |
| 8,273,751 | B2 | 9/2012 | Li et al. |
| 2003/0069246 | A1 | 4/2003 | Darrow et al. |
| 2003/0092908 | A1 | 5/2003 | Pitts et al. |
| 2003/0162782 | A1 | 8/2003 | Grossman et al. |
| 2005/0075795 | A1 | 4/2005 | Pandit |
| 2005/0113379 | A1 | 5/2005 | Ge et al. |
| 2006/0252790 | A1 | 11/2006 | Allen et al. |
| 2008/0176961 | A1 | 7/2008 | Greengard et al. |
| 2008/0188492 | A1 | 8/2008 | Li et al. |
| 2008/0193964 | A1 | 8/2008 | Greengard et al. |
| 2008/0194592 | A1 | 8/2008 | Mates et al. |
| 2010/0087450 | A1 | 4/2010 | Fienberg et al. |
| 2010/0173878 | A1 | 7/2010 | Li et al. |
| 2010/0273753 | A1 | 10/2010 | Li et al. |
| 2010/0273754 | A1 | 10/2010 | Li |
| 2010/0323997 | A1 | 12/2010 | Fienberg et al. |
| 2011/0245214 | A1 | 10/2011 | Li et al. |
| 2011/0281832 | A1 | 11/2011 | Li et al. |
| 2011/0312978 | A1 | 12/2011 | Davis et al. |
| 2012/0053190 | A1 | 3/2012 | Fienberg et al. |
| 2012/0071450 | A1 | 3/2012 | Li et al. |
| 2012/0094966 | A1 | 4/2012 | Li et al. |
| 2012/0136013 | A1 | 5/2012 | Li et al. |

FOREIGN PATENT DOCUMENTS

| | | |
|---|---|---|
| DE | 19931206 | 1/2001 |
| EP | 0095289 | 11/1983 |
| EP | 0201188 | 12/1986 |
| EP | 0636626 | 2/1995 |
| EP | 0911333 | 4/2002 |
| WO | WO 91/19717 | 12/1991 |
| WO | WO 94/19351 | 9/1994 |
| WO | WO 98/46606 | 10/1998 |
| WO | WO 98/52568 | 11/1998 |
| WO | WO 01/27113 | 4/2001 |
| WO | WO 02/074312 | 9/2002 |
| WO | WO 03/002567 | 1/2003 |
| WO | WO 03/020702 | 3/2003 |
| WO | WO 03/020724 | 3/2003 |
| WO | WO 03/042216 | 5/2003 |
| WO | WO 2006/133261 | 12/2006 |

(Continued)

OTHER PUBLICATIONS

"Autism," [retrieved on May 14, 2008]. Retrieved online via Internet, URL: http://www.nlm.nih.gov/medlineplus/autism.html.*
"Anxiety," [retrieved on May 14, 2008]. Retrieved online via Internet, URL: http://www.nlm.nih.gov/medlineplus/anxiety.html.*
Ahn, H., et al. "Potent Tetracyclic Guanine Inhibitors of PDE1 and PDE5 Cyclic Guanosine Monophosphate Phosphodiesterases with Oral Antihypertensive Activity", J. Med. Chem. (1997) 40(14):2196-2210.
Banker, Gilbert S. et al., Modem Pharmaceutics, Marcel Dekker, New York, 1996.
Bender et al., "Cyclic Nucleotide Phosphodiesterases: Molecular Regulation to Clinical Use" PharmcoL Rev., 2006, 58, pp. 488-520.

(Continued)

*Primary Examiner* — Kristin Vajda
(74) *Attorney, Agent, or Firm* — Hoxie & Associates, LLC

(57) ABSTRACT

Optionally substituted 4,5,7,8-tetrahydro-(optionally 4-oxo, 4-thioxo or 4-imino)-2H-imidazo[1,2-a]pyrrolo[3,4-e]pyrimidine or 4,5,7,8,9-pentahydro-(optionally 4-oxo, 4-thioxo or 4-imino)-2H-pyrimido[1,2-a]pyrrolo[3,4-e]pyrimidine compounds or Compounds of Formula (I), processes for their production, their use as pharmaceuticals and pharmaceutical compositions comprising the same.

31 Claims, No Drawings

(56) References Cited

FOREIGN PATENT DOCUMENTS

| | | |
|---|---|---|
| WO | WO 2007/143568 | 12/2007 |
| WO | WO 2007/143705 | 12/2007 |
| WO | WO 2008/063505 | 5/2008 |
| WO | WO 2009/073210 | 6/2009 |
| WO | WO 2009/075784 | 6/2009 |
| WO | WO 2011/043816 | 4/2011 |
| WO | WO 2011/153129 | 12/2011 |
| WO | WO 2011/153135 | 12/2011 |
| WO | WO 2011/153136 | 12/2011 |
| WO | WO 2011/153138 | 12/2011 |

OTHER PUBLICATIONS

Chebib et al., 1-Phenylpyrazolo[3,4-d]pyrimidines; Structure-Activity Relationships for C6 Substituents at $A_1$ and $A_{2A}$ Adenosine Receptors Bioorganic & Medicinal Chemistry (2000) 8:2581-2590.

Dewald et al., Synthesis and Potential Antipsychotic Activity of 1 H-Imidazo[1.2-c]pyrazolo[3,4-e]pyrimidines', J. Med. Chem. 1988, 31, pp. 454-461.

Fienberg et al., "DARPP-32: Regulator of the Efficacy of Dopaminergic Neurotransmission", Science, (1998) 281, pp. 838-842.

Greengard et al., "Beyond the Dopamine Receptor: the DARPP-32lProtein Phosphatase-1 Cascade", Neuron, 1999,23, pp. 435,447.

Han et al., "The Calcium/Calmodulin-dependent Phosphodiesterase PDE1C Downregulates Glucose-induced Insulin Secretion", J. Bio, Chem., 1999,274(32), pp. 22337-22344.

Jiang, et al., Chemoenzymatic Asymmetric Total Synthesis of Phosphodiesterase Inhibitors: Preparation of a Polycyclic Pyrazolo[3,4-d]pyrimidine from an Acylnitroso Oiels-Alder Cycloadduct-Derived Aminocyclopentenol, J. Org. Chem., 70, 2824-2827 (2004).

Mani et al., Science (2000) 287: 1053.

Murray et al., "Expression and activity of cAMP phosphodiesterase isoforms in pulmonary artery smooth muscle cells from patients with pulmonary hypertension: role for PDE1", Am. J. Physiol. Lunr:l Cell Mol. Physiol. 2007, 292, pp. L294-L303.

Nishi, A., et al., "Advanced Research on Dopamine Signaling to Develop Drugs for the Treatment of Mental Disorders: Biochemical and Behavioral Profiles of Phosphodiesterase Inhibition in Dopaminergic Neurotransmission", J. Pharmacol. Sci. vol. 114, pp. 6-16, (2010).

Polli et al., "Expression of a Calmodulin-Dependent Phosphodiesterase Isoform (PDE1 B1) Correlates With Brain Regions Having Extensive Dopaminergic Innervation," (1994), The Journal of Neuroscience, 14:1251-1261.

Porsolt et al. Nature (1977) 266:730-732.

Poulsen et al. HIgh-Pressure Synthesis of Enantiomerlcally Pure C-6 Substituted Pyrazolo[3,4-d]pyrimidines Biorganic & Medicinal Chemistry letter (2001) 11:191-193.

Reed et al., "Phosphodiesterase 1 B Knock-Out Mice Exhibit Exaggerated Locomotor Hyperactivity and DARPP-32 Phosphorylation in Response to Dopamine Agonists and Display Impaired Spatial Learning", The Journal of Neuroscience, 2002, 22(12), pp. 5188-5197.

Rybalkin et al., "Cyclic GMP Phosphodiesterases and Regulation of Smooth Muscle Function", Circ. Res. 2003,93, pp. 280-291.

Shimizu et al., "Calmodulin-Dependent Cyclic Nucleotide Phosphodiesterase (PDE1) Is a Pharmacological Target of Differentiation-Inducing Factor-1, an Antitumor Agent Isolated from Dictyostelium", Cancer Research, 2004, 64, pp. 2568-2571.

Turko et al., Inhibition of Cyclic GMP-Binding Cyclic GMP-Specific Phosphodiesterase (Type 5) by Sildenafil and Related Compounds Molecular Pharmacology (1990) 56:124-130.

Vatter, et al., Differential Phosphodiesterase Expression and Cytosolic Ca2+ in Human CNS Tumour Cells and in Non-Malignant and Malignant Cells of Rat Origin, J. of Neurochemistry, 93, 321-329 (2005).

Wolff, Manfred E., Burger's Medicinal Chemistry and Drug Discovery, Fifth Ed., vol. 1: Principles and Practice, John Wiley & Sons, 1995, 975.

Xia, et al., Synthesis and Evaluation of Polycyclic Pyrazolo[3,4-d]pyrimidines as PDE1 and PDE5 cGMP Phosphodiesterase Inhibitors, J. Med. Chem., 40, 4372-77 (1997).

Al-Afaleq, E., et al., "Heterocyclic o-Aminonitriles: Preparation of Pyrazolo[3,4-d]-pyrimidines with Modification of the substituents at the 1-position", *Molecules*, 6, pp. 621-638, (2001).

Blokland, "PDE Inhibition and Cognition Enhancement", vol. 22 No. 4, pp. 349-354 (2012) (Abstract Only).

Gelbin, et al., "Ketene-S, N-acetals as synthons for heterocycles new synthesis of pyrimidinones", *Journal Fuer Praktische Chemie*, vol. 329, No. 5, pp. 753-766, (1987).

Goodman & Gilman, The Pharmacological Basis of Therapeutics, McGraw-Hill Interamericana. 2007, p. 892. (cited within text of Office Action from corresponding Costa Rican application, attached herein).

Office Action from related U.S. Appl. No. 13/133,082 mailed on Feb. 6, 2013.

Office Action from related U.S. Appl. No. 13/133,033 mailed on Feb. 6, 2013.

Chen et al., Effects of Bimatoprost 0.03% on Ocular Hemodynamics in Normal Tension Glaucoma; Journal of Ocular Pharmacology nd Therpaeutics, vol. 22, No. 3, 2006.

Noguchi et al; "A Facile Preparation of 7-(substitued amino-)-6H-pyrrolo[3,4-d]-pyrimidine Derivatives"; Bulletin Chem. Soc. Of Japan, 62(9), 3043-5; (1989).

\* cited by examiner

ORGANIC COMPOUNDS

CROSS REFERENCE TO RELATED APPLICATIONS

This application is a U.S. filing under 35 U.S.C. 371 of PCT/US2009/06438 filed on Dec. 7, 2009, which claims the benefit of U.S. Provisional Application No. 61/120,440 filed on Dec. 6, 2008, the contents of each of which are incorporated herein by reference.

TECHNICAL FIELD

The present invention relates to optionally substituted 4,5,7,8-tetrahydro-(optionally 4-oxo, 4-thioxo or 4-imino)-2H-imidazo[1,2-a]pyrrolo[3,4-e]pyrimidine or 4,5,7,8,9-pentahydro-(optionally 4-oxo, 4-thioxo or 4-imino)-2H-pyrimido[1,2-a]pyrrolo[3,4-e]pyrimidine, for example, compounds of Formula II (Formula II-A and II-B) and Formula I (Formula I-A and I-B) as described below, processes for their production, their use as pharmaceuticals and pharmaceutical compositions comprising them. Of particular interest are novel compounds useful as inhibitors of phosphodiesterase 1 (PDE1), e.g., in the treatment of diseases involving disorders of the dopamine D1 receptor intracellular pathway, such as Parkinson's disease, depression, narcolepsy, damage to cognitive function, e.g., in schizophrenia, or disorders that may be ameliorated through enhanced progesterone-signaling pathway, e.g., female sexual dysfunction as well as other disease or conditions characterized by low levels of cAMP and/or cGMP in cells expressing PDE1 and those characterized by reduced dopamine D1 receptor signaling activities.

BACKGROUND OF THE INVENTION

Eleven families of phosphodiesterases (PDEs) have been identified but only PDEs in Family I, the $Ca^{2+}$-calmodulin-dependent phosphodiesterases (CaM-PDEs), have been shown to mediate both the calcium and cyclic nucleotide (e.g. cAMP and cGMP) signaling pathways. The three known CaM-PDE genes, PDE1A, PDE1B, and PDE1C, are all expressed in central nervous system tissue. PDE1A is expressed throughout the brain with higher levels of expression in the CA1 to CA3 layers of the hippocampus and cerebellum and at a low level in the striatum. PDE1A is also expressed in the lung and heart. PDE1B is predominately expressed in the striatum, dentate gyms, olfactory tract and cerebellum, and its expression correlates with brain regions having high levels of dopaminergic innervation. Although PDE1B is primarily expressed in the central nervous system, it may be detected in the heart. PDE1C is primarily expressed in olfactory epithelium, cerebellar granule cells, and striatum. PDE1C is also expressed in the heart and vascular smooth muscle.

Cyclic nucleotide phosphodiesterases decrease intracellular cAMP and cGMP signaling by hydrolyzing these cyclic nucleotides to their respective inactive 5'-monophosphates (5'AMP and 5'GMP). CaM-PDEs play a critical role in mediating signal transduction in brain cells, particularly within an area of the brain known as the basal ganglia or striatum. For example, NMDA-type glutamate receptor activation and/or dopamine D2 receptor activation result in increased intracellular calcium concentrations, leading to activation of effectors such as calmodulin-dependent kinase II (CaMKII) and calcineurin and to activation of CaM-PDEs, resulting in reduced cAMP and cGMP. Dopamine D1 receptor activation, on the other hand, leads to activation of nucleotide cyclases, resulting in increased cAMP and cGMP. These cyclic nucleotides in turn activate protein kinase A (PKA; cAMP-dependent protein kinase) and/or protein kinase G (PKG; cGMP-dependent protein kinase) that phosphorylate downstream signal transduction pathway elements such as DARPP-32 (dopamine and cAMP-regulated phosphoprotein) and cAMP responsive element binding protein (CREB). Phosphorylated DARPP-32 in turn inhibits the activity of protein phosphates-1 (PP-1), thereby increasing the state of phosphorylation of substrate proteins such as progesterone receptor (PR), leading to induction of physiologic responses. Studies in rodents have suggested that inducing cAMP and cGMP synthesis through activation of dopamine D1 or progesterone receptor enhances progesterone signaling associated with various physiological responses, including the lordosis response associated with receptivity to mating in some rodents. See Mani, et al., Science (2000) 287: 1053, the contents of which are incorporated herein by reference.

CaM-PDEs can therefore affect dopamine-regulated and other intracellular signaling pathways in the basal ganglia (striatum), including but not limited to nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), DARPP-32, and endorphin intracellular signaling pathways.

Phosphodiesterase (PDE) activity, in particular, phosphodiesterase 1 (PDE1) activity, functions in brain tissue as a regulator of locomotor activity and learning and memory. PDE1 is a therapeutic target for regulation of intracellular signaling pathways, preferably in the nervous system, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), endorphin intracellular signaling pathway and progesterone signaling pathway. For example, inhibition of PDE1B should act to potentiate the effect of a dopamine D1 agonist by protecting cGMP and cAMP from degradation, and should similarly inhibit dopamine D2 receptor signaling pathways, by inhibiting PDE1 activity. Chronic elevation in intracellular calcium levels is linked to cell death in numerous disorders, particularly in neurodegerative diseases such as Alzheimer's, Parkinson's and Huntington's Diseases and in disorders of the circulatory system leading to stroke and myocardial infarction. PDE1 inhibitors are therefore potentially useful in diseases characterized by reduced dopamine D1 receptor signaling activity, such as Parkinson's disease, restless leg syndrome, depression, narcolepsy and cognitive impairment. PDE1 inhibitors are also useful in diseases that may be alleviated by the enhancement of progesterone-signaling such as female sexual dysfunction.

There is thus a need for compounds that selectively inhibit PDE1 activity, especially PDE1A and/or PDE1B activity.

SUMMARY OF THE INVENTION

The invention provides optionally substituted 4,5,7,8-tetrahydro-2H-imidazo[1,2-a]pyrrolo[3,4-e]pyrimidine or 4,5,7,8,9-pentahydro-2H-pyrimido[1,2-a]pyrrolo[3,4-e]pyrimidine, e.g., a Compound of Formula II, e.g., II-A or II-B:

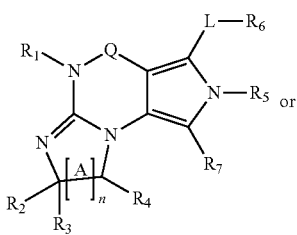

Formula II-A

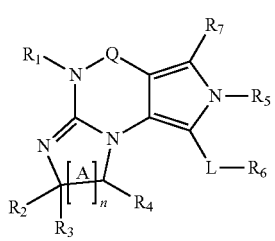

Formula II-B wherein
(i) Q is C(=O), C(=S), C(=N(R$_{20}$)) or CH$_2$;
(ii) L is a single bond, —N(H)—, —CH$_2$—, —S—, —S(O)— or —S(O$_2$)—;
(iii) R$_1$ is H or C$_{1-4}$ alkyl (e.g., methyl);
(iv) R$_4$ is H or C$_{1-6}$ alkyl (e.g., methyl or isopropyl) and R$_2$ and R$_3$ are, independently,
H
C$_{1-6}$alkyl (e.g., methyl, isopropyl) optionally substituted with halo or hydroxy (e.g., R$_2$ and R$_3$ are both methyl, or R$_2$ is H and R$_3$ is methyl, ethyl, isopropyl or hydroxyethyl),
aryl,
heteroaryl,
(optionally hetero)arylalkoxy,
(optionally hetero)arylC$_{1-6}$alkyl; or
R$_2$ and R$_3$ together form a 3- to 6-membered ring;
or
R$_2$ is H and R$_3$ and R$_4$ together form a di-, tri- or tetramethylene bridge (pref. wherein the R$_3$ and R$_4$ together have the cis configuration, e.g., where the carbons carrying R$_3$ and R$_4$ have the R and S configurations, respectively);
or
(v) R$_5$ is
a) -D-E-F, wherein:
D is C$_{1-4}$alkylene (e.g., methylene, ethylene or prop-2-yn-1-ylene);
E is a single bond, C$_{2-4}$alkynylene (e.g., arylene (e.g., phenylene) or heteroarylene (e.g., pyridylene);
F is
H,
aryl (e.g., phenyl),
heteroaryl (e.g., pyridyl, diazolyl, triazolyl, for example, pyrid-2-yl, imidazol-1-yl, 1,2,4-triazol-1-yl),
halo (e.g., F, Br, Cl),
haloC$_{1-4}$alkyl (e.g., trifluoromethyl),
—C(O)—R$_{15}$,
—N(R$_{16}$)(R$_{17}$), or
C$_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
wherein D, E and F are independently and optionally substituted with one or more halo (e.g., F, Cl or Br), C$_{1-4}$alkyl (e.g., methyl), haloC$_{1-4}$alkyl (e.g., trifluoromethyl), C$_{1-4}$alkoxy (e.g., methoxy), hydroxy, C$_{1-4}$carboxy, or an additional aryl or heteroaryl (e.g., biphenyl or pyridylphenyl),
for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), haloC$_{1-4}$alkyl (e.g., 5-trifluoromethylpyrid-2-yl) or C$_{1-4}$alkyl (e.g., 5-methylpyrid-2-yl), or F is aryl, e.g., phenyl, substituted with one or more halo (e.g., 4-fluorophenyl) or F is a C$_{3-7}$heterocycloalkyl (e.g., pyrrolidinyl) optionally substituted with a C$_{1-6}$alkyl (e.g., 1-methylpyrrolidin-3-yl); or
b) a substituted heteroarylalkyl, e.g., substituted with haloC$_{1-4}$alkyl;
c) attached to the nitrogen on the pyrrolo portion of Formula II-A or II-B and is a moiety of Formula A

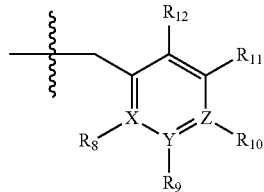

Formula A wherein X, Y and Z are, independently, N or C, and R$_8$, R$_9$, R$_{11}$ and R$_{12}$ are independently H or halogen (e.g., Cl or F), and R$_{10}$ is
halogen,
C$_{1-4}$alkyl,
haloC$_{1-4}$alkyl (e.g., triflouromethyl)
C$_{1-4}$alkoxy (e.g. methoxy),
C$_{3-7}$cycloalkyl,
heteroC$_{3-7}$cycloalkyl (e.g., pyrrolidinyl or piperidinyl),
C$_{1-4}$haloalkyl (e.g., trifluoromethyl),
aryl (e.g., phenyl),
heteroaryl (e.g., pyridyl (for example pyrid-2-yl or pyrid-4-yl), or thiadiazolyl (e.g., 1,2,3-thiadiazol-4-yl)), diazolyl (e.g., imidazol-1-yl), triazolyl (e.g., 1,2,4-triazol-1-yl), tetrazolyl,
arylcarbonyl (e.g., benzoyl),
alkylsulfonyl (e.g., methylsulfonyl),
heteroarylcarbonyl, or
alkoxycarbonyl;
wherein the aryl, heteroaryl, cycloalkyl or heterocycloalkyl is independently, optionally substituted with one or more C$_{1-4}$alkyl (e.g., methyl), halogen (e.g., chloro or fluoro), haloC$_{1-4}$alkyl (e.g., trifluoromethyl), hydroxy, C$_{1-4}$carboxy, —SH or an additional aryl, heteroaryl (e.g., biphenyl or pyridylphenyl) or C$_{3-8}$cycloalkyl,
preferably R$_{10}$ is phenyl, pyridyl, piperidinyl or pyrrolidinyl optionally substituted with the substituents previously defined, e.g. optionally substituted with halo or alkyl
provided that when X, Y, or Z is nitrogen, R$_8$, R$_9$, or R$_{10}$, respectively, is not present;
(vi) R$_6$ is
H,
C$_{1-4}$alkyl (e.g., methyl, ethyl, n-propyl, isobutyl),
C$_{3-7}$cycloalkyl (e.g., cyclopentyl or cyclohexyl),
heteroC$_{3-7}$cycloalkyl (e.g., pyrrolidinyl, piperidinyl, morpholinyl),
aryl (e.g., phenyl),
heteroaryl (e.g., pyrid-4-yl), arylC$_{1-4}$alkyl (e.g., benzyl), arylamino (e.g., phenylamino), heteroarylamino, N,N-diC$_{1-4}$alkylamino, N,N-diarylamino, N-aryl-N-(arylC$_{1-4}$alkyl)amino (e.g., N-phenyl-N-(1,1'-biphen-4-ylmethyl)amino), or

—N(R$_{18}$)(R$_{19}$), wherein the aryl and heteroaryl are optionally substituted with one or more C$_{1-4}$alkyl (e.g., methyl), halogen (e.g., chloro or fluoro), haloC$_{1-4}$alkyl (e.g., trifluoromethyl), hydroxy, C$_{1-4}$carboxy, or an additional aryl, heteroaryl (e.g., biphenyl or pyridylphenyl) or C$_{3-8}$cycloalkyl;

(vii) R$_7$ is H, C$_{1-6}$alkyl (e.g., methyl or ethyl), halogen (e.g., Cl), —N(R$_{18}$)(R$_{19}$), hydroxy or C$_{1-6}$alkoxy;

(viii) n=0 or 1;

(ix) when n=1, A is —C(R$_{13}$R$_{14}$)—, wherein R$_{13}$ and R$_{14}$, are, independently, H or C$_{1-4}$alkyl, aryl, heteroaryl, (optionally hetero)arylC$_{1-4}$alkoxy, (optionally hetero)arylC$_{1-4}$alkyl or R$_{14}$ can form a bridge with R$_2$ or R$_4$;

(x) R$_{15}$ is C$_{1-4}$alkyl, haloC$_{1-4}$alkyl, —OH or —OC$_{1-4}$alkyl (e.g., —OCH$_3$)

(xi) R$_{16}$ and R$_{17}$ are independently H or C$_{1-4}$alkyl;

(xii) R$_{18}$ and R$_{19}$ are independently

H,

C$_{1-4}$alky (e.g., methyl, ethyl, n-propyl, isobutyl),

C$_{3-8}$cycloalky (e.g., cyclohexyl or cyclopenyl), heteroC$_{3-8}$cycloalky (e.g., pyrrolidinyl, piperidinyl, morpholinyl), aryl (e.g., phenyl) or heteroaryl (e.g., pyridyl), wherein said aryl and heteroaryl are optionally substituted with one or more halo (e.g., fluorophenyl, e.g., 4-fluorophenyl), hydroxy (e.g., hydroxyphenyl, e.g., 4-hydroxyphenyl or 2-hydroxyphenyl), C$_{1-4}$alkyl (e.g., methyl), haloC$_{1-4}$alkyl (e.g., trifluoromethyl), C$_{1-4}$carboxy, or an additional aryl, heteroaryl (e.g., biphenyl or pyridylphenyl) or C$_{3-8}$cycloalkyl, (xiii) R$_{20}$ is H, C$_{1-4}$alkyl or C$_{3-7}$cycloalkyl;

in free or salt form.

In another aspect, the invention provides a Compound of Formula I, e.g. Formula I-A and I-B:

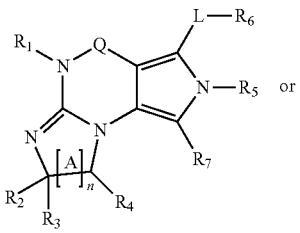

Formula I-A

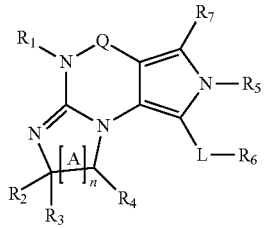

Formula I-B wherein (i) Q is C(=O), C(=S), C(=N(R$_{20}$)) or CH$_2$;

(ii) L is a single bond, —N(H)—, —CH$_2$—, —S—, —S(O)— or —S(O$_2$)—;

(iii) R$_1$ is H or C$_{1-4}$ alkyl (e.g., methyl);

(iv) R$_4$ is H or C$_{1-6}$ alkyl (e.g., methyl or isopropyl) and R$_2$ and R$_3$ are, independently, H or C$_{1-6}$alkyl (e.g., methyl, isopropyl) optionally substituted with halo or hydroxy (e.g., R$_2$ and R$_3$ are both methyl, or R$_2$ is H and R$_3$ is methyl, ethyl, isopropyl or hydroxyethyl), aryl, heteroaryl, (optionally hetero)arylalkoxy, or (optionally hetero)arylC$_{1-6}$alkyl;

or

R$_2$ is H and R$_3$ and R$_4$ together form a di-, tri- or tetramethylene bridge (pref. wherein the R$_3$ and R$_4$ together have the cis configuration, e.g., where the carbons carrying R$_3$ and R$_4$ have the R and S configurations, respectively);

(v) R$_5$ is a) -D-E-F, wherein:

D is C$_{1-4}$alkylene (e.g., methylene, ethylene or prop-2-yn-1-ylene);

E is a single bond, C$_{2-4}$alkynylene (e.g., —C≡C—), arylene (e.g., phenylene) or heteroarylene (e.g., pyridylene);

F is

H, aryl (e.g., phenyl), heteroaryl (e.g., pyridyl, diazolyl, triazolyl, for example, pyrid-2-yl, imidazol-1-yl, 1,2,4-triazol-1-yl), halo (e.g., F, Br, Cl), haloC$_{1-4}$alkyl (e.g., trifluoromethyl),

—C(O)—R$_{15}$,

—N(R$_{16}$)(R$_{17}$), or

C$_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);

wherein D, E and F are independently and optionally substituted with one or more halo (e.g., F, Cl or Br), C$_{1-4}$alkyl (e.g., methyl), haloC$_{1-4}$alkyl (e.g., trifluoromethyl), for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), haloC$_{1-4}$alkyl (e.g., 5-trifluoromethylpyrid-2-yl) or C$_{1-4}$alkyl (e.g., 5-methylpyrid-2-yl), or F is aryl, e.g., phenyl, substituted with one or more halo (e.g., 4-fluorophenyl) or F is a C$_{3-7}$heterocycloalkyl (e.g., pyrrolidinyl) optionally substituted with a C$_{1-6}$alkyl (e.g., 1-methylpyrrolidin-3-yl); or
b) a substituted heteroarylalkyl, e.g., substituted with haloalkyl;
c) attached to the nitrogen on the pyrrolo portion of Formula I-A or I-B and is a moiety of Formula A

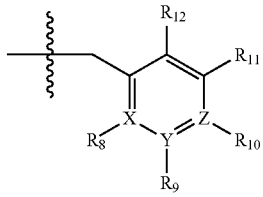

Formula A wherein X, Y and Z are, independently, N or C, and R$_8$, R$_9$, R$_{11}$ and R$_{12}$ are independently H or halogen (e.g., Cl or F), and R$_{10}$ is
halogen,
C$_{1-4}$alkyl,
C$_{3-7}$cycloalkyl,
C$_{1-4}$haloalkyl (e.g., trifluoromethyl),
aryl (e.g., phenyl),
heteroaryl (e.g., pyridyl (for example pyrid-2-yl), or thiadiazolyl (e.g., 1,2,3-thiadiazol-4-yl)), diazolyl, triazolyl, tetrazolyl,
arylcarbonyl (e.g., benzoyl),
alkylsulfonyl (e.g., methylsulfonyl),
heteroarylcarbonyl, or
alkoxycarbonyl;
provided that when X, Y, or Z is nitrogen, R$_8$, R$_9$, or R$_{10}$, respectively, is not present;
(vi) R$_6$ is
H,
C$_{1-4}$alkyl,
C$_{3-7}$cycloalkyl (e.g., cyclopentyl),
aryl (e.g., phenyl),
heteroaryl (e.g., pyrid-4-yl),
arylC$_{1-4}$alkyl (e.g., benzyl),
arylamino (e.g., phenylamino),
heteroarylamino,
N,N-diC$_{1-4}$alkylamino,
N,N-diarylamino,
N-aryl-N-(arylC$_{1-4}$alkyl)amino (e.g., N-phenyl-N-(1,1'-biphen-4-ylmethyl)amino), or
—N(R$_{18}$)(R$_{19}$);
wherein the aryl or heteroaryl is optionally substituted with one or more halo (e.g., F, Cl), hydroxy or C$_{1-6}$alkoxy;
(vii) R$_7$ is H, C$_{1-6}$alkyl, halogen (e.g., Cl), —N(R$_{18}$)(R$_{19}$);
(viii) n=0 or 1;
(ix) when n=1, A is —C(R$_{13}$R$_{14}$)—, wherein R$_{13}$ and R$_{14}$, are, independently, H or C$_{1-4}$alkyl, aryl, heteroaryl, (optionally hetero)arylC$_{1-4}$alkoxy or (optionally hetero)arylC$_{1-4}$alkyl;
(x) R$_{15}$ is C$_{1-4}$alkyl, haloC$_{1-4}$alkyl, —OH or —OC$_{1-4}$alkyl (e.g., —OCH$_3$)
(xi) R$_{16}$ and R$_{17}$ are independently H or C$_{1-4}$alkyl;
(xii) R$_{18}$ and R$_{19}$ are independently H, C$_{1-4}$alky or aryl (e.g., phenyl) wherein said aryl is optionally substituted with one or more halo (e.g., fluorophenyl, e.g., 4-fluorophenyl) or hydroxy (e.g., hydroxyphenyl, e.g., 4-hydroxyphenyl or 2-hydroxyphenyl)
(xiii) R$_{20}$ is H, C$_{1-4}$alkyl or C$_{3-7}$cycloalkyl;
in free, salt or prodrug form.

The invention further provides compounds of Formula I (I-A and I-B) as follows:
1.1 Formula I-A or I-B, wherein Q is C(=O), C(=S), C(=N(R$_{20}$)) or CH$_2$;
1.2 Formula I-A or I-B or 1.1, wherein Q is C(=S);
1.3 Formula I-A or I-B or 1.1, wherein Q is C(=N(R$_{20}$));
1.4 Formula I-A or I-B or 1.1, wherein Q is CH$_2$;
1.5 Formula I-A or I-B or 1.1, wherein Q is C(=O);
1.6 Formula I-A or I-B, or any of 1.1-1.5, wherein L is a single bond, —N(H)—, —CH$_2$—, —S—, —S(O)— or —S(O$_2$)—;
1.7 Formula 1.6, wherein L is a single bond;
1.8 Formula 1.6, wherein L is —N(H)—;
1.9 Formula 1.6, wherein L is —CH$_2$—;
1.10 Formula 1.6, wherein L is —S—;
1.11 Formula 1.6, wherein L is —S(O)—;
1.12 Formula 1.6, wherein L is —S(O$_2$)—;
1.13 Formula I-A or I-B, or any of 1.1-1.12, wherein R$_1$ is H or C$_{1-4}$ alkyl (e.g., methyl);
1.14 Formula 1.13, wherein R$_1$ is H;
1.15 Formula 1.13, wherein R$_1$ is C$_{1-4}$ alkyl (e.g., methyl);
1.16 Formula I-A or I-B, or any of 1.1-1.15, wherein R$_4$ is H or C$_{1-6}$ alkyl (e.g., methyl, isopropyl) and R$_2$ and R$_3$ are, independently,
H or C$_{1-6}$alkyl optionally substituted with halo or hydroxy (e.g., R$_2$ and R$_3$ are both methyl, or R$_2$ is H and R$_3$ is methyl, ethyl, isopropyl or hydroxyethyl),
aryl,
heteroaryl,
(optionally hetero)arylalkoxy, or
(optionally hetero)arylC$_{1-6}$alkyl;
1.17 Formula I-A or I-B, or any of 1.1-1.15, wherein R$_2$ is H and R$_3$ and R$_4$ together form a di-, tri- or tetramethylene bridge (pref. wherein the R$_3$ and R$_4$ together have the cis configuration, e.g., where the carbons carrying R$_3$ and R$_4$ have the R and S configurations, respectively);
1.18 Formula I-A or I-B or any of 1.1-1.17, wherein R$_5$ is -D-E-F;
1.19 Formula 1.18, wherein D is C$_{1-4}$alkylene (e.g., methylene, ethylene or prop-2-yn-1-ylene);
1.20 Formula 1.19, wherein D is methylene;
1.21 Any of formulae 1.18-1.20, wherein E is a single bond, C$_{2-4}$alkynylene (e.g., —C≡C—), arylene (e.g., phenylene) or heteroarylene (e.g., pyridylene);
1.22 Any of formulae 1.18-1.20, wherein E is arylene (e.g., phenylene);
1.23 Any of formulae 1.18-1.20, wherein E is phenylene;
1.24 Any of formulae 1.18-1.20, wherein E is heteroarylene (e.g., pyridylene);
1.25 Any of formulae 1.18-1.20, wherein E is phenylene wherein F is para-substituted;
1.26 Any of formulae 1.18-1.20, wherein E is heteroarylene (e.g., pyridylene);
1.27 Any of formulae 1.18-1.20, wherein E is a single bond;
1.28 Any of formulae 1.18-1.27, wherein F is H, aryl (e.g., phenyl), heteroaryl (e.g., pyridyl, e.g., pyrid-2-yl), halo (e.g., F, Br, Cl), haloC$_{1-4}$alkyl (e.g., trifluoromethyl), —C(O)—R$_{15}$, —N(R$_{16}$)(R$_{17}$), or C$_{3-4}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
1.29 Formula 1.28, wherein F is haloC$_{1-4}$alkyl (e.g., trifluoromethyl);
1.30 Formula 1.28, wherein F is trifluoromethyl;
1.31 Formula 1.28, wherein F is halo (e.g., F, Br, Cl);
1.32 Formula 1.28, wherein F is Cl;
1.33 Formula 1.28, wherein F is heteroaryl (e.g., pyridyl, e.g., pyrid-2-yl);

1.34 Formula 1.28, wherein F is pyridyl;
1.35 Formula 1.28, wherein F is pyrid-2-yl;
1.36 Formula 1.28, wherein F is $C_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, morpholinyl);
1.37 Formula 1.28, wherein F is cyclohexyl;
1.38 Formula 1.28, wherein F is pyrrolidinyl (e.g., pyrrolidin-3-yl);
1.39 Formula 1.28, wherein F is cyclopentyl;
1.40 Formula 1.28, wherein F is tetrahydro-2H-pyran-4-yl;
1.41 Formula 1.28, wherein F is aryl (e.g., phenyl);
1.42 Formula 1.28, wherein F is phenyl;
1.43 Formula 1.28, wherein F is 4-fluorophenyl;
1.44 Formula 1.28, wherein F is —C(O)—$R_{15}$ and $R_{15}$ is $C_{1-4}$alkyl (e.g., methyl), halo$C_{1-4}$alkyl (e.g., trifluoromethyl), —OH or —O$C_{1-4}$alkyl (e.g., —OCH$_3$);
1.45 Any of formulae 1.18-1.44, wherein D, E and F are independently and optionally substituted with one or more halo (e.g., F, Cl or Br), $C_{1-4}$alkyl (e.g., methyl), halo$C_{1-4}$alkyl (e.g., trifluoromethyl), for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-4}$alkyl (e.g., 5-trifluoromethylpyrid-2-yl) or $C_{1-4}$alkyl (e.g., 5-methylpyrid-2-yl), or F is aryl, e.g., phenyl, substituted with one or more halo (e.g., 4-fluorophenyl), or F is a $C_{3-7}$heterocycloalkyl (e.g., pyrrolidinyl) optionally substituted with a $C_{1-6}$alkyl (e.g., 1-methylpyrrolidin-3-yl);
1.46 Formula 1.45, wherein F is substituted with one or more halo (e.g., F, Cl or Br), $C_{1-4}$alkyl (e.g., methyl), halo$C_{1-4}$alkyl (e.g., trifluoromethyl);
1.47 Formula 1.45, wherein F is 6-fluoropyrid-2-yl;
1.48 Formula 1.45, wherein F is 3-fluoropyrid-2-yl;
1.49 Formula 1.45, wherein F is 4-fluoropyrid-2-yl;
1.50 Formula 1.45, wherein F is 5-fluoropyrid-2-yl;
1.51 Formula 1.45, wherein F is heteroaryl, e.g., pyridyl, optionally substituted with one or more halo$C_{1-4}$alkyl (e.g., 5-trifluoromethylpyrid-2-yl);
1.52 Formula 1.45, wherein F is 5-trifluoromethylpyrid-2-yl;
1.53 Formula 1.45, wherein F is heteroaryl, e.g., pyridyl, optionally substituted with one or more $C_{1-4}$alkyl (e.g., 5-methylpyrid-2-yl);
1.54 Formula 1.45, wherein F is 5-methylpyrid-2-yl;
1.55 Formula 1.28, wherein F is —C(O)—$R_{15}$ and $R_{15}$ is methyl;
1.56 Formula 1.28, wherein F is —C(O)—$R_{15}$ and $R_{15}$ is trifluoromethyl;
1.57 Formula 1.28, wherein F is —C(O)—$R_{15}$ and $R_{15}$ is —OH;
1.58 Formula 1.28, wherein F is —C(O)—$R_{15}$ and $R_{15}$ is —O$C_{1-4}$alkyl (e.g., —OCH$_3$);
1.59 Formula 1.28, wherein F is —C(O)—$R_{15}$ and $R_{15}$ is —OCH$_3$;
1.60 Formula 1.28, wherein F is —N($R_{16}$)($R_{17}$);
1.61 Formula I-A or I-B or any of 1.1-1.17, wherein $R_5$ is a substituted heteroarylalkyl, e.g., substituted with haloalkyl;
1.62 Formula I-A or I-B or any of 1.1-1.17, wherein $R_5$ is attached to one of the nitrogens on the pyrazolo portion of Formula I-A or I-B and is a moiety of Formula A

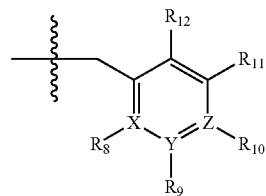

Formula A wherein X, Y and Z are, independently, N or C, and $R_8$, $R_9$, $R_{11}$ and $R_{12}$ are independently H or halogen (e.g., Cl or F), and $R_{10}$ is halogen, $C_{1-4}$alkyl, $C_{3-7}$cycloalkyl, $C_{1-4}$haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, $R_8$, $R_9$, or $R_{10}$, respectively, is not present
1.63 Formula 1.62, wherein $R_5$ is a substituted heteroarylmethyl, e.g., para-substituted with haloalkyl;
1.64 Formula 1.62, wherein $R_5$ is a moiety of Formula A wherein $R_8$, $R_9$, $R_{11}$, and $R_{12}$ are H and $R_{10}$ is phenyl;
1.65 Formula 1.62, wherein $R_5$ is a moiety of Formula A wherein $R_8$, $R_9$, $R_{11}$, and $R_{12}$ are H and $R_{10}$ is pyridyl or thiadiazolyl;
1.66 Formula 1.62, wherein $R_5$ is a moiety of Formula A wherein $R_8$, $R_9$, $R_{11}$, and $R_{12}$ are, independently, H or halogen, and $R_{10}$ is haloalkyl;
1.67 Formula 1.62, wherein $R_5$ is a moiety of Formula A wherein $R_8$, $R_9$, $R_{11}$, and $R_{12}$ are, independently, H, and $R_{10}$ is alkyl sulfonyl;
1.68 Formula I-A or I-B or any of 1.1-1.67, wherein $R_6$ is H, $C_{1-4}$alkyl, $C_{3-7}$cycloalkyl (e.g., cyclopentyl), aryl, heteroaryl, aryl$C_{1-4}$alkyl (e.g., benzyl), arylamino (e.g., phenylamino), heteroarylamino, N,N-di$C_{1-4}$alkylamino, N,N-diarylamino, N-aryl-N-(aryl$C_{1-4}$alkyl)amino (e.g., N-phenyl-N-(1,1'-biphen-4-ylmethyl)amino), or —N($R_{18}$)($R_{19}$), wherein the aryl or heteroaryl is optionally substituted with one or more halo (e.g., F, Cl), hydroxy or $C_{1-6}$alkoxy;
1.69 Formula 1.68, wherein $R_6$ is H;
1.70 Formula 1.68, wherein $R_6$ is aryl (e.g., phenyl) optionally substituted with one or more halo (e.g., F, Cl), hydroxy or $C_{1-6}$alkoxy;
1.71 Formula 1.68, wherein $R_6$ is $C_{1-4}$alkyl;
1.72 Formula 1.68, wherein $R_6$ is $C_{3-7}$cycloalkyl (e.g., cyclopentyl);
1.73 Formula 1.68, wherein $R_6$ is fluorophenyl (e.g., 4-fluorophenyl) or hydroxyphenyl (e.g., 4-hydroxyphenyl or 2-hydroxyphenyl);
1.74 Formula I-A or I-B or any of 1.1-1.73, wherein $R_7$ is H, $C_{1-6}$alkyl (e.g., methyl), halogen, —N($R_{18}$)($R_{19}$);
1.75 Formula 1.74, wherein $R_7$ is H;
1.76 Formula 1.74, wherein $R_7$ is $C_{1-6}$alkyl (e.g., methyl);
1.77 Formula 1.74, wherein $R_7$ is methyl;
1.78 Formula 1.74, wherein $R_7$ is ethyl;
1.79 Formula I-A or I-B or any of 1.1-1.78, wherein n=0;
1.80 Formula I-A or I-B or any of 1.1-1.78, wherein n=1;
1.81 Formula 1.80, wherein n=1, A is —C($R_{13}R_{14}$)—, wherein $R_{13}$ and $R_{14}$ are, independently, H or $C_{1-4}$alkyl, aryl, heteroaryl, (optionally hetero)aryl$C_{1-4}$alkoxy or (optionally hetero)aryl$C_{1-4}$alkyl;

1.82 any of the preceding formulae wherein the compound is Formula I-A;
1.83 any of the preceding formulae wherein the compound is selected from a group consisting of:
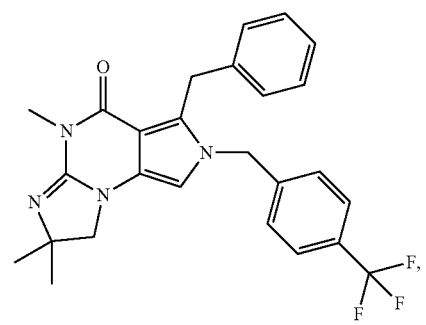
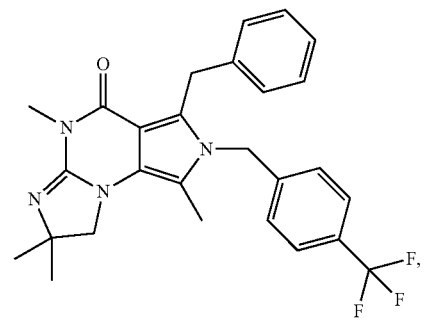
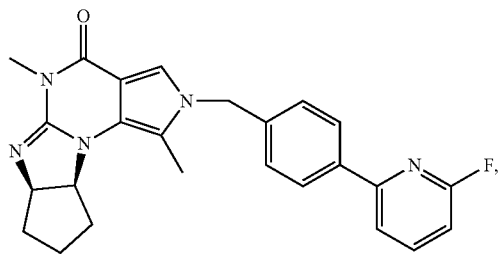
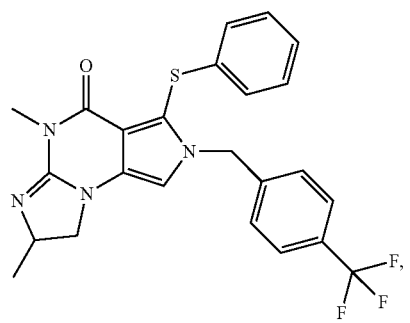
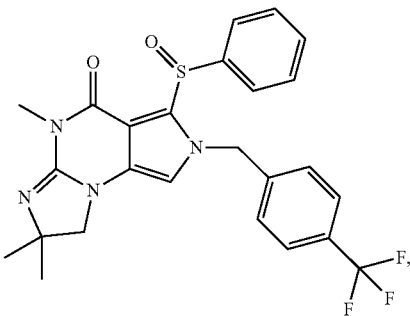
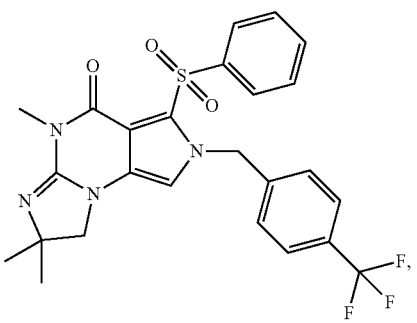
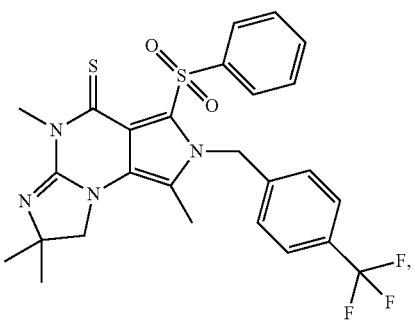
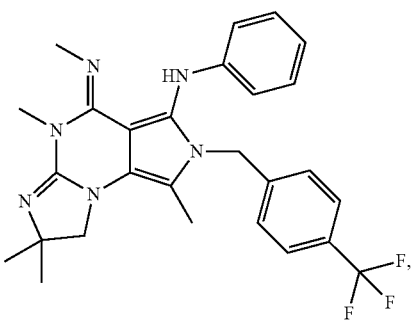
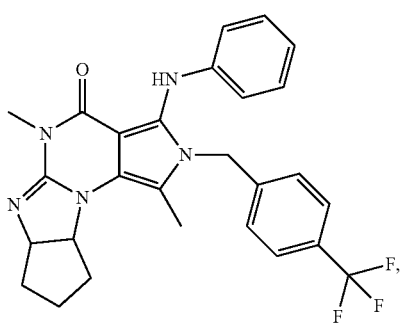
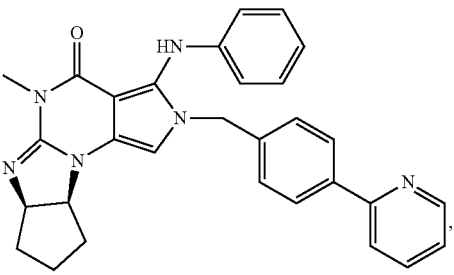

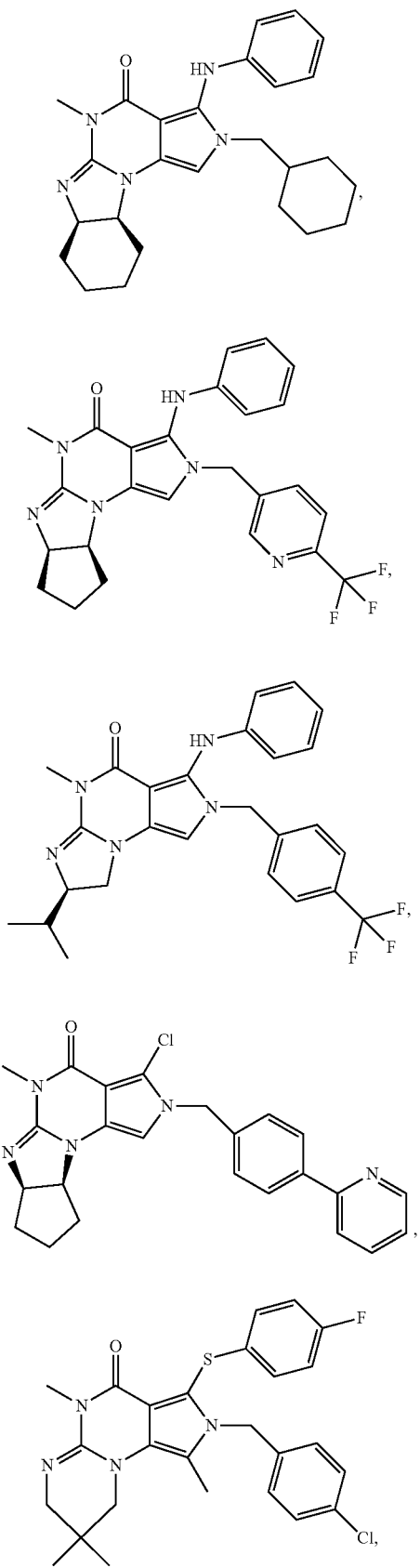

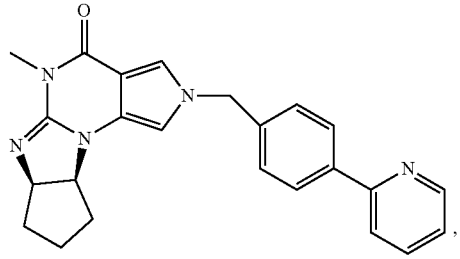,

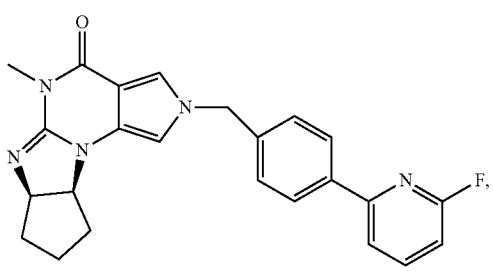,

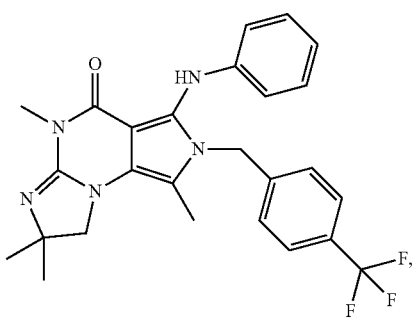,

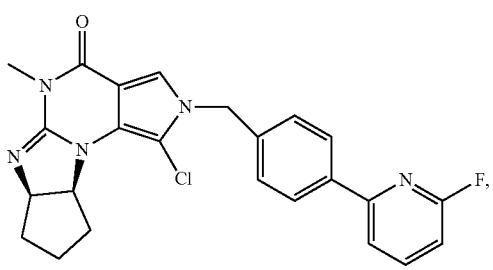,

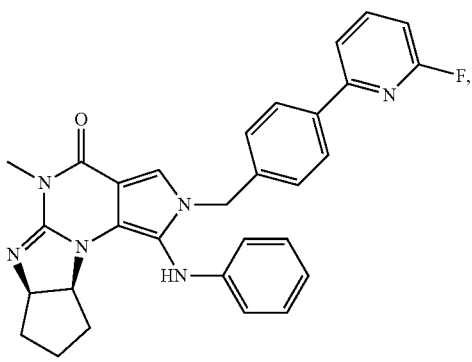,

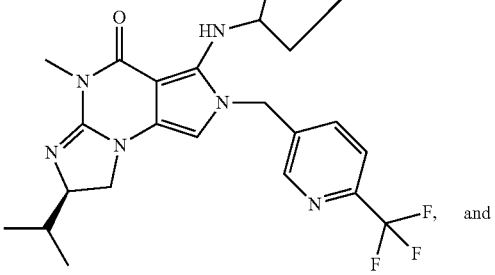 and

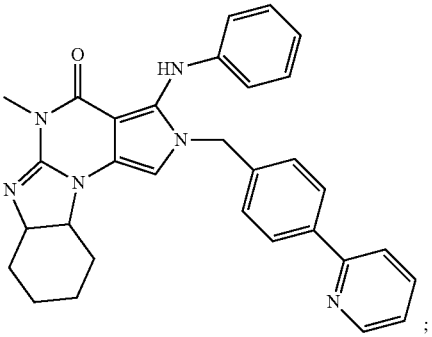;

1.84 any of the preceding formulae wherein the compounds inhibit phosphodiesterase-mediated (e.g., PDE1-mediated, especially PDE1B-mediated) hydrolysis of cGMP, e.g., with an $IC_{50}$ of less than 1 µM, preferably less than 750 nM, more preferably less than 500 nM, more preferably less than 50 nM in an immobilized-metal affinity particle reagent PDE assay, for example, as described in Example 16, in free or salt form.

In still another embodiment, the invention provides a compound as follows:

2.1 a Compound of Formula I-A, I-B, II-A or II-B, or any of 1.1-1.6, 1.14-1.67, 1.74-1.84, wherein L is a single bond or —$CH_2$—;

2.2 formula 2.1, wherein $R_6$ is
H,
arylamino (e.g., phenylamino),
heteroarylamino,
N,N-di$C_{1-4}$alkylamino,
N,N-diarylamino,
N-aryl-N-(aryl$C_{1-4}$alkyl)amino (e.g., N-phenyl-N-(1,1'-biphen-4-ylmethyl)amino), or
—N($R_{18}$)($R_{19}$),
wherein the aryl and heteroaryl are optionally substituted with one or more $C_{1-4}$alkyl (e.g., methyl), halogen (e.g., chloro or fluoro), halo$C_{1-4}$alkyl (e.g., trifluoromethyl), hydroxy, $C_{1-4}$carboxy, or an additional aryl, heteroaryl (e.g., biphenyl or pyridylphenyl) or $C_{3-8}$cycloalkyl;

2.3 a Compound of Formula I-A, I-B, II-A or II-B, or any of 1.1-1.6, 1.14-1.67, 1.74-1.84, wherein L is a single bond, —$CH_2$—, —N(H)—, —S—, —S(O)— or —$S(O_2)$—;

2.4 a formula 2.3, wherein $R_6$ is
H,
$C_{1-4}$alkyl (e.g., methyl, ethyl, n-propyl, isobutyl),
$C_{3-7}$cycloalkyl (e.g., cyclopentyl or cyclohexyl),
hetero$C_{3-7}$cycloalkyl (e.g., pyrrolidinyl, piperidinyl, morpholinyl),
aryl (e.g., phenyl), heteroaryl (e.g., pyrid-4-yl),
arylC$_{1-4}$alkyl (e.g., benzyl),
   wherein the aryl and heteroaryl are optionally substituted with one or more C$_{1-4}$alkyl (e.g., methyl), halogen (e.g., chloro or fluoro), haloC$_{1-4}$alkyl (e.g., trifluoromethyl), hydroxy, C$_{1-4}$carboxy, or an additional aryl, heteroaryl (e.g., biphenyl or pyridylphenyl) or C$_{3-8}$cycloalkyl;
2.5 a Compound of Formula I-A, I-B, II-A or II-B, or any of 2.1[0010]-2.4, wherein R$_5$ is attached to the nitrogen on the pyrrolo portion of Formula I-A, I-B, II-A or II-B and is a moiety of Formula A

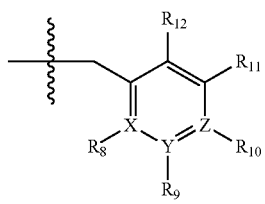

Formula A wherein X, Y and Z are, independently, N or C, and R$_8$, R$_9$, R$_{11}$ and R$_{12}$ are independently H or halogen (e.g., Cl or F), and R$_{10}$ is
C$_{3-7}$cycloalkyl,
heteroC$_{3-7}$cycloalkyl (e.g., pyrrolidinyl or piperidinyl),
aryl (e.g., phenyl), or
heteroaryl (e.g., pyridyl (for example pyrid-2-yl or pyrid-4-yl), or thiadiazolyl (e.g., 1,2,3-thiadiazol-4-yl)), diazolyl (e.g., imidazol-1-yl), triazolyl (e.g., 1,2,4-triazol-1-yl), tetrazolyl,
wherein the aryl, heteroaryl, cycloalkyl or heterocycloalkyl is independently, optionally substituted with one or more C$_{1-4}$alkyl (e.g., methyl), halogen (e.g., chloro or fluoro), haloC$_{1-4}$alkyl (e.g., trifluoromethyl), hydroxy, C$_{1-4}$carboxy, —SH or an additional aryl or heteroaryl (e.g., biphenyl or pyridylphenyl),
provided that when X, Y, or Z is nitrogen, R$_8$, R$_9$, or R$_{10}$, respectively, is not present;
2.6 Formula I-A, I-B, II-A or II-B or any of 2.1-2.5, wherein n=0;
2.7 Formula I-A, I-B, II-A or II-B or any of 2.1-2.5, wherein n=1;
2.8 Any of the preceding formulae wherein L is —N(H)—, —S—, —S(O)— or —S(O$_2$)— and R$_6$ is:
H,
C$_{1-4}$alkyl (e.g., methyl, ethyl, n-propyl, isobutyl),
C$_{3-7}$cycloalkyl (e.g., cyclopentyl or cyclohexyl),
heteroC$_{3-7}$cycloalkyl (e.g., pyrrolidinyl, piperidinyl, morpholinyl),
aryl (e.g., phenyl),
heteroaryl (e.g., pyrid-4-yl),
arylC$_{1-4}$alkyl (e.g., benzyl),
wherein the aryl and heteroaryl are optionally substituted with one or more C$_{1-4}$alkyl (e.g., methyl), halogen (e.g., chloro or fluoro), haloC$_{1-4}$alkyl (e.g., trifluoromethyl), hydroxy, C$_{1-4}$carboxy, or an additional aryl, heteroaryl (e.g., biphenyl or pyridylphenyl) or C$_{3-8}$cycloalkyl;
2.9 a Compound of Formula I-A, I-B, II-A or II-B, or any of the preceding formulae, wherein the remaining substituents are as defined in any of formula 1.1-1.84;
2.10 any of the preceding formulae, wherein the compound is selected from any of the following:

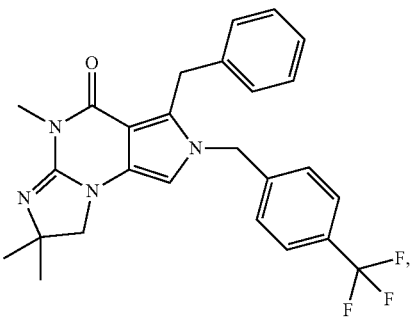

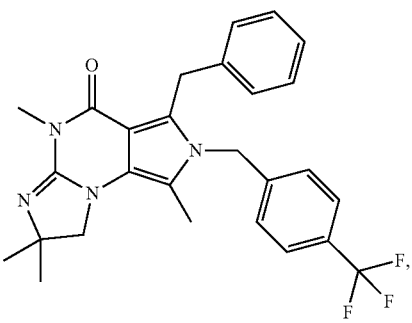

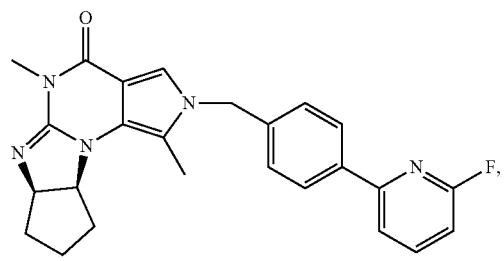

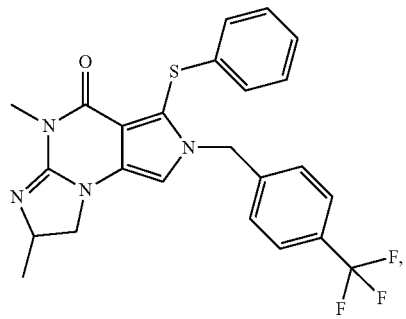

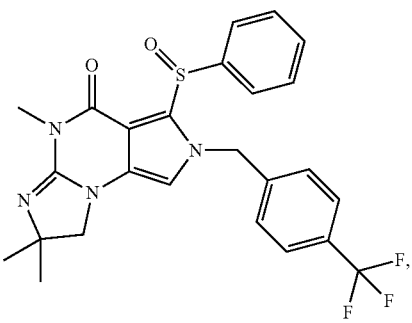

21
-continued
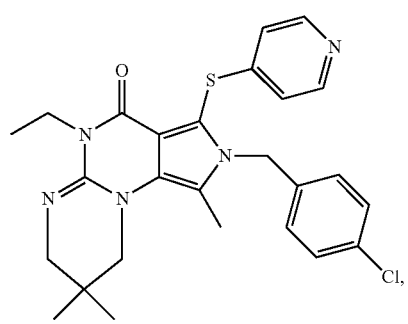
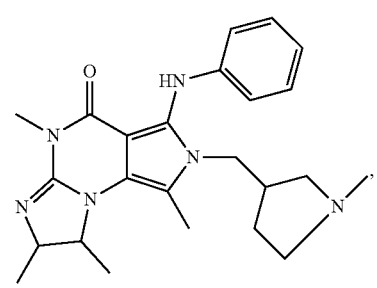
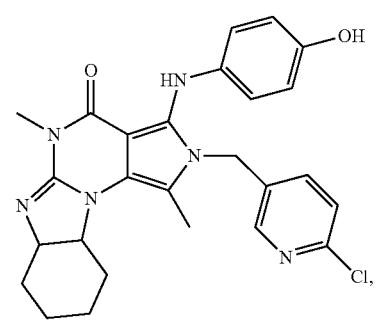
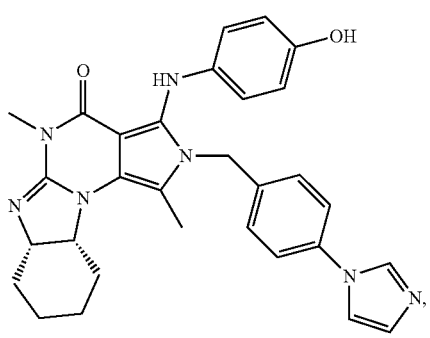
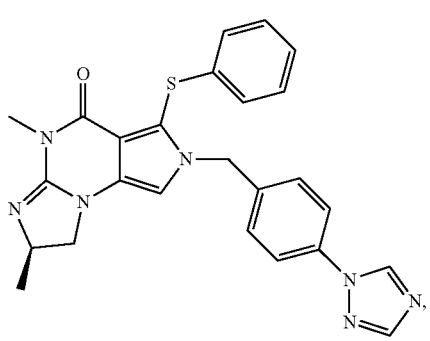
22
-continued
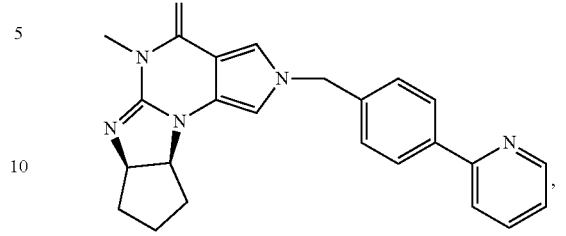
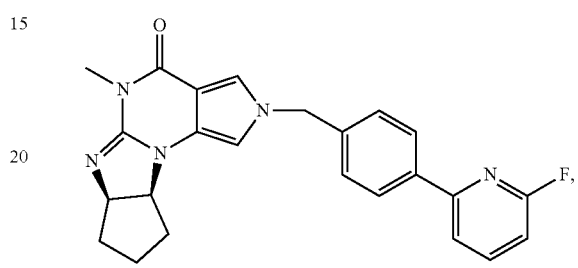
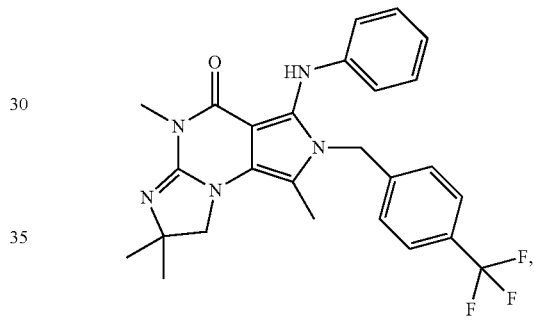
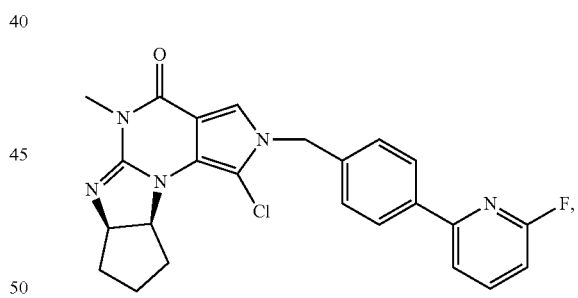
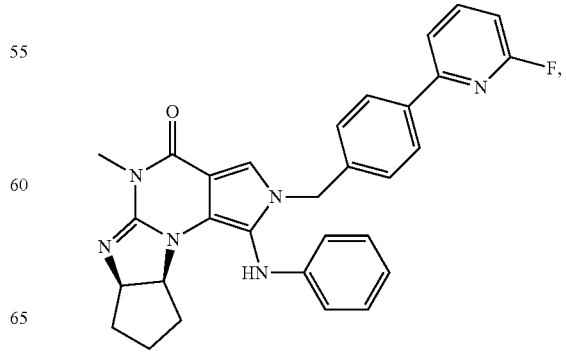

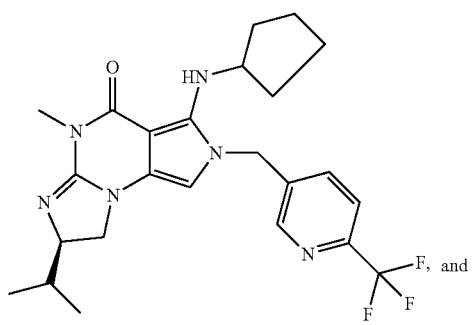
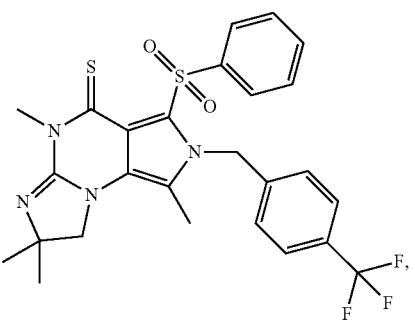
2.11 any of the preceding formulae, wherein the compound is selected from any of the following
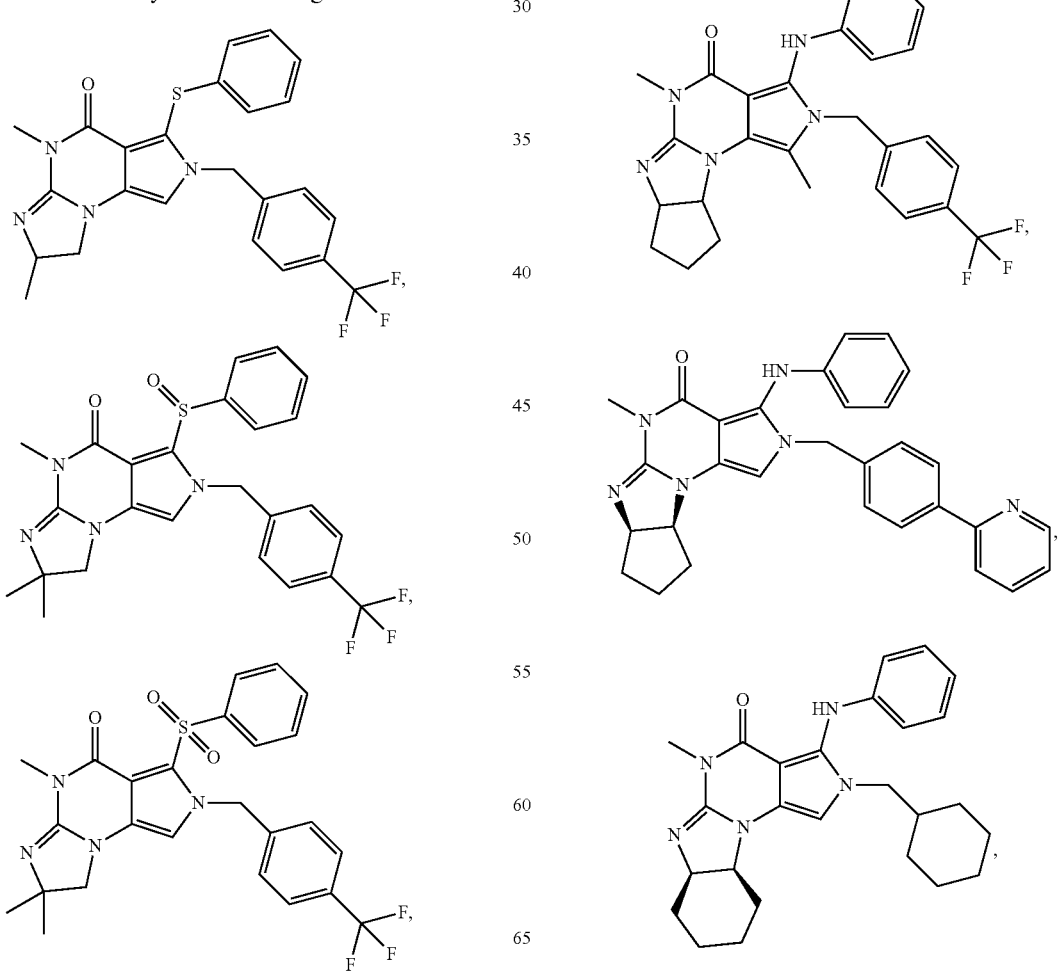

25
-continued
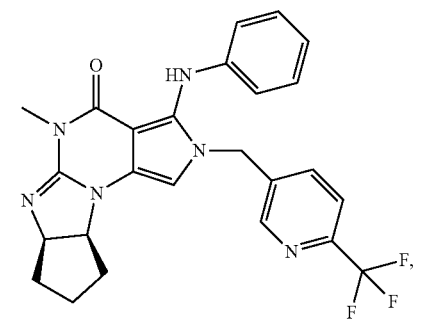
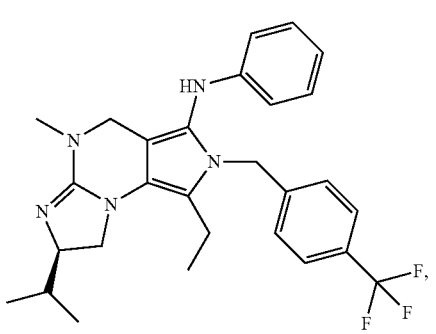
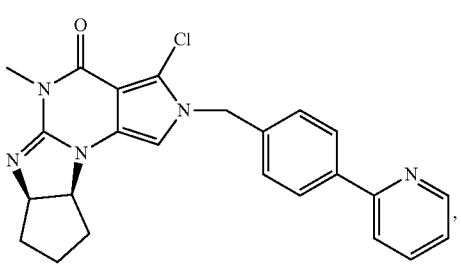
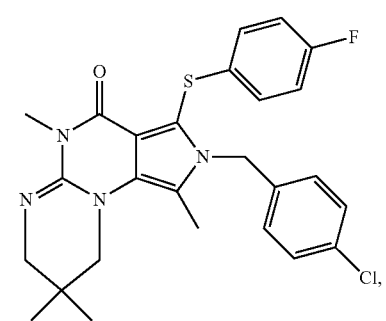
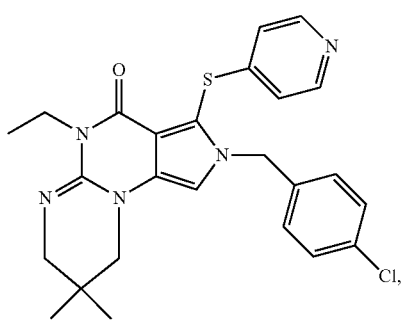
26
-continued
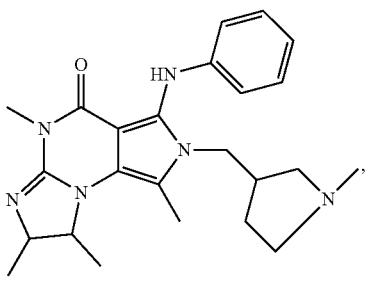
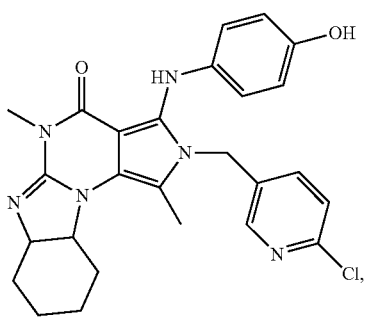
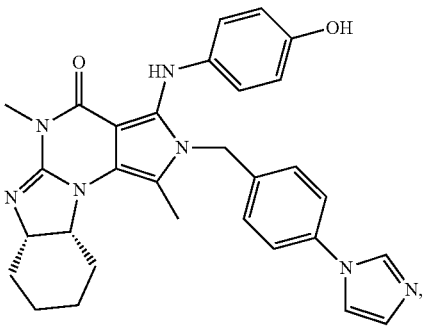
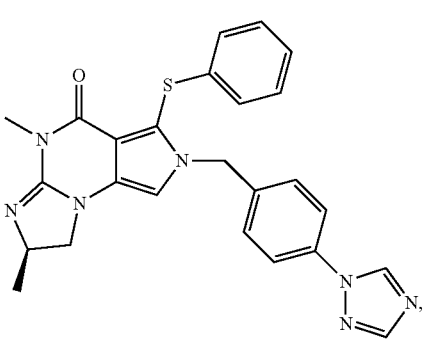
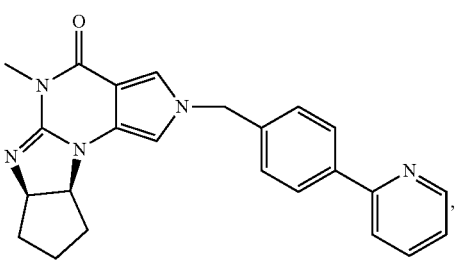

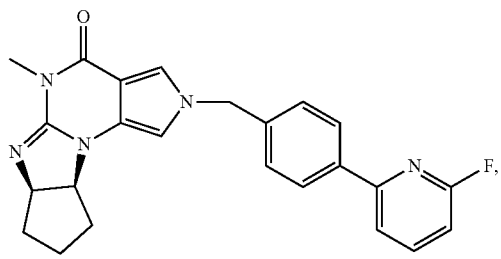
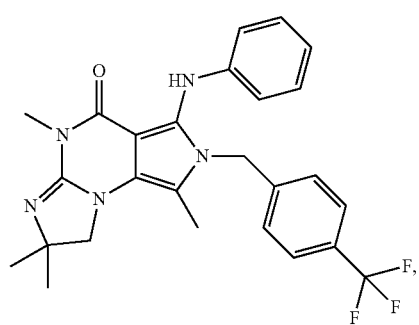
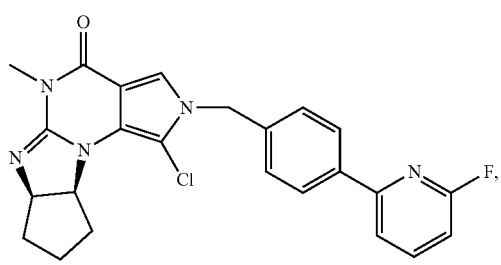
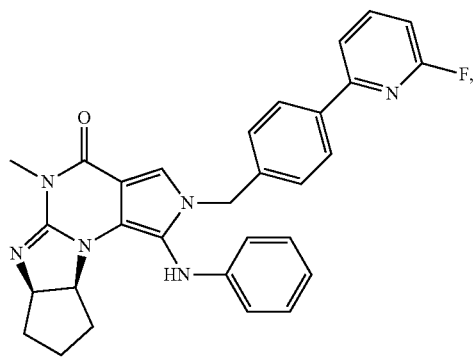
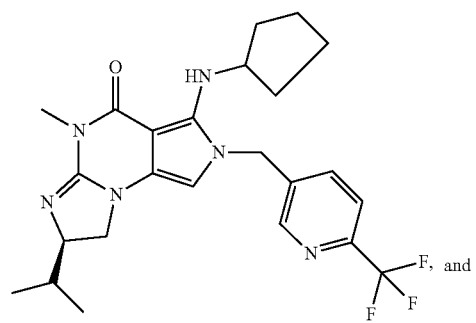
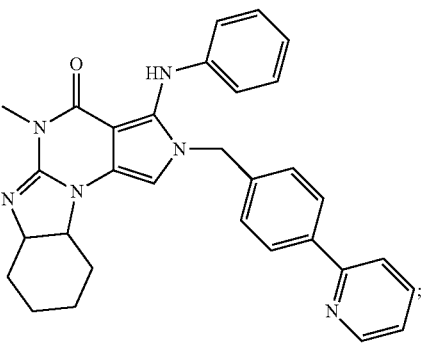
2.12 any of the preceding formulae, wherein the compound is selected from any of the following:
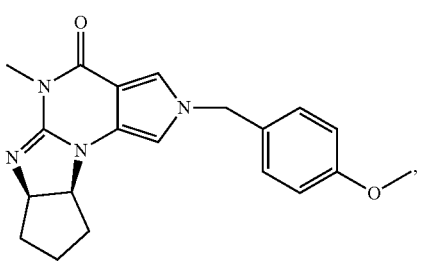
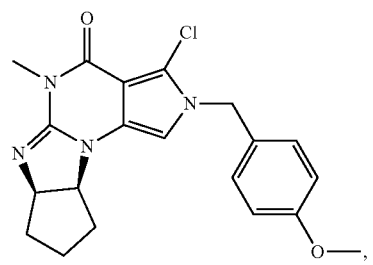
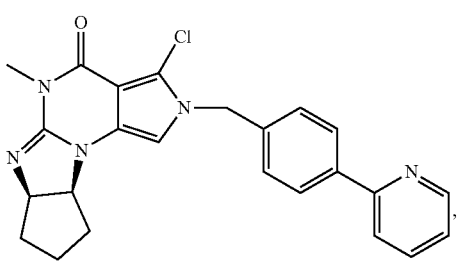
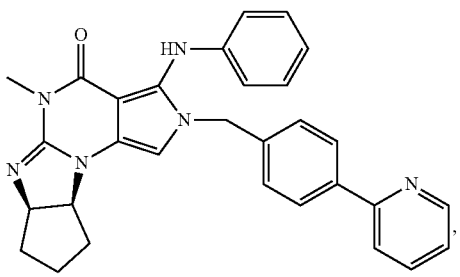

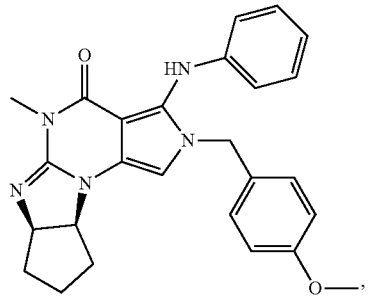

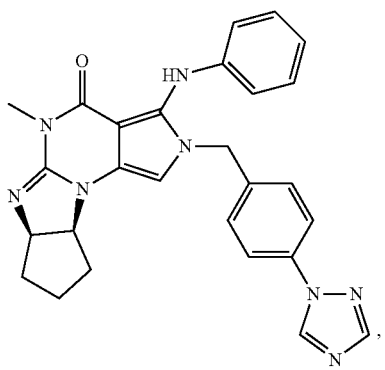

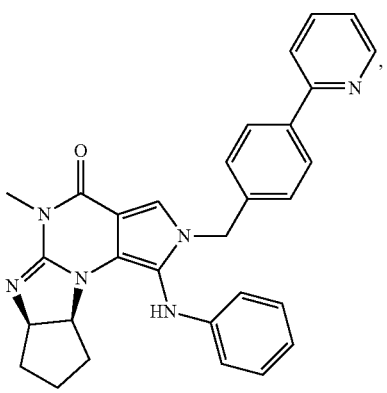

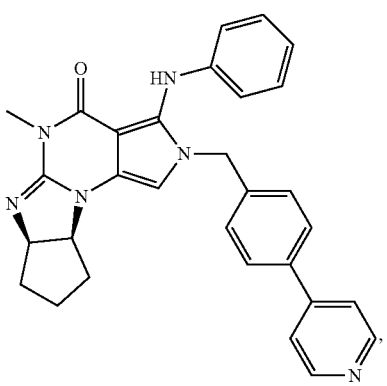

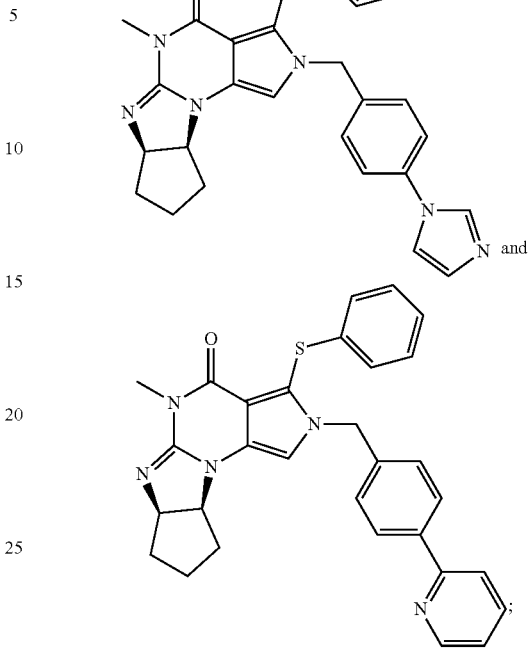

2.13 any of the preceding formulae, wherein the compounds inhibit phosphodiesterase-mediated (e.g., PDE1-mediated, especially PDE1A- and/or PDE1B-mediated) hydrolysis of cGMP, e.g., with an $IC_{50}$ of less than 10 μM, preferably less than 1 μM, still preferably less than 750 nM, more preferably less than 500 nM, more preferably less than 50 nM especially less than 10 nM in an immobilized-metal affinity particle reagent PDE assay, for example, as described in Example 16, in free or salt form.

In one embodiment, the Compound of the Invention is a Compound of Formula I-A, I-B, II-A or II-B, wherein:
(i) Q is C(=O), C(=S), C(=N($R_{20}$)) or $CH_2$;
(ii) L is a single bond, —$CH_2$—, —N(H)—, —S—, —S(O)— or —S($O_2$)—;
(iii) $R_1$ is H or $C_{1-4}$ alkyl (e.g., methyl);
(iv) $R_4$ is H or $C_{1-6}$ alkyl (e.g., methyl or isopropyl) and $R_2$ and $R_3$ are, independently,
   H
   $C_{1-6}$alkyl (e.g., methyl, isopropyl) optionally substituted with halo or hydroxy (e.g., $R_2$ and $R_3$ are both methyl, or $R_2$ is H and $R_3$ is methyl, ethyl, isopropyl or hydroxyethyl),
   aryl,
   heteroaryl,
   (optionally hetero)arylalkoxy,
   (optionally hetero)aryl$C_{1-6}$alkyl, or
   $R_2$ and $R_3$ together form a 3-6-membered ring;
   or
   $R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(v) $R_5$ is
   a) -D-E-F, wherein:
      D is $C_{1-4}$alkylene (e.g., methylene, ethylene or prop-2-yn-1-ylene);

E is a single bond, $C_{2-4}$alkynylene (e.g., —C≡C—), arylene (e.g., phenylene) or heteroarylene (e.g., pyridylene);

F is
  H,
  aryl (e.g., phenyl),
  heteroaryl (e.g., pyridyl, diazolyl, triazolyl, for example, pyrid-2-yl, imidazol-1-yl, 1,2,4-triazol-1-yl),
  halo (e.g., F, Br, Cl),
  halo$C_{1-4}$alkyl (e.g., trifluoromethyl),
  —C(O)—$R_{15}$,
  —N($R_{16}$)($R_{17}$), or
  $C_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
  wherein D, E and F are independently and optionally substituted with one or more halo (e.g., F, Cl or Br), $C_{1-4}$alkyl (e.g., methyl), halo$C_{1-4}$alkyl (e.g., trifluoromethyl), $C_{1-4}$alkoxy (e.g., methoxy), hydroxy, $C_{1-4}$carboxy, or an additional aryl or heteroaryl (e.g., biphenyl or pyridylphenyl),
  for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-4}$alkyl (e.g., 5-trifluoromethylpyrid-2-yl) or $C_{1-4}$alkyl (e.g., 5-methylpyrid-2-yl), or F is aryl, e.g., phenyl, substituted with one or more halo (e.g., 4-fluorophenyl) or F is a $C_{3-7}$heterocycloalkyl (e.g., pyrrolidinyl) optionally substituted with a $C_{1-6}$alkyl (e.g., 1-methylpyrrolidin-3-yl); or b) a substituted heteroarylalkyl, e.g., substituted with halo$C_{1-4}$alkyl;

c) attached to the nitrogen on the pyrrolo portion of Formula I-A, I-B, II-A or II-B and is a moiety of Formula A

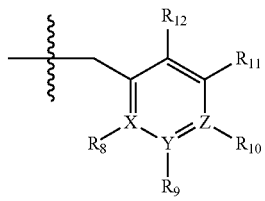

Formula A wherein X, Y and Z are, independently, N or C, and $R_8$, $R_9$, $R_{11}$ and $R_{12}$ are independently H or halogen (e.g., Cl or F), and $R_{10}$ is
  halogen,
  $C_{1-4}$alkyl,
  halo$C_{1-4}$alkyl (e.g., triflouromethyl)
  $C_{1-4}$alkoxy (e.g. methoxy),
  $C_{3-7}$cycloalkyl,
  hetero$C_{3-7}$cycloalkyl (e.g., pyrrolidinyl or piperidinyl),
  hetero $C_{1-4}$haloalkyl (e.g., trifluoromethyl),
  aryl (e.g., phenyl),
  heteroaryl (e.g., pyridyl (for example pyrid-2-yl or pyrid-4-yl), or thiadiazolyl (e.g., 1,2,3-thiadiazol-4-yl)), diazolyl (e.g., imidazol-1-yl), triazolyl (e.g., 1,2,4-triazol-1-yl), tetrazolyl,
  arylcarbonyl (e.g., benzoyl),
  alkylsulfonyl (e.g., methylsulfonyl),
  heteroarylcarbonyl, or
  alkoxycarbonyl;
  wherein the aryl, heteroaryl, cycloalkyl or heterocloalkyl is independently, optionally substituted with one or more $C_{1-4}$alkyl (e.g., methyl), halogen (e.g., chloro or fluoro), halo$C_{1-4}$alkyl (e.g., trifluoromethyl), hydroxy, $C_{1-4}$carboxy, —SH or an additional aryl or heteroaryl (e.g., biphenyl or pyridylphenyl),
  provided that when X, Y, or Z is nitrogen, $R_8$, $R_9$, or $R_{10}$, respectively, is not present;

(vi) $R_6$ is
  H,
  $C_{1-4}$alkyl (e.g., methyl, ethyl, n-propyl, isobutyl),
  $C_{3-7}$cycloalkyl (e.g., cyclopentyl or cyclohexyl),
  hetero$C_{3-7}$cycloalkyl (e.g., pyrrolidinyl, piperidinyl, morpholinyl),
  aryl (e.g., phenyl),
  heteroaryl (e.g., pyrid-4-yl),
  aryl$C_{1-4}$alkyl (e.g., benzyl),
  wherein the aryl and heteroaryl are optionally substituted with one or more $C_{1-4}$alkyl (e.g., methyl), halogen (e.g., chloro or fluoro), halo$C_{1-4}$alkyl (e.g., trifluoromethyl), hydroxy, $C_{1-4}$carboxy, or an additional aryl, heteroaryl (e.g., biphenyl or pyridylphenyl) or $C_{3-8}$cycloalkyl;
  when L is a single bond, —$CH_2$—, —N(H)—, —S—, —S(O)— or $S(O_2)$—,
  or
  $R_6$ is
  H,
  arylamino (e.g., phenylamino),
  heteroarylamino,
  N,N-di$C_{1-4}$alkylamino,
  N,N-diarylamino,
  N-aryl-N-(aryl$C_{1-4}$alkyl)amino (e.g., N-phenyl-N-(1,1'-biphen-4-ylmethyl)amino), or
  —N($R_{18}$)($R_{19}$),
  wherein the aryl and heteroaryl are optionally substituted with one or more $C_{1-4}$alkyl (e.g., methyl), halogen (e.g., chloro or fluoro), halo$C_{1-4}$alkyl (e.g., trifluoromethyl), hydroxy, $C_{1-4}$carboxy, or an additional aryl, heteroaryl (e.g., biphenyl or pyridylphenyl) or $C_{3-8}$cycloalkyl;
  when L is a single bond or —$CH_2$—;

(vii) $R_7$ is H, $C_{1-6}$alkyl (e.g., methyl or ethyl), halogen (e.g., Cl), —N($R_{18}$)($R_{19}$), hydroxy or $C_{1-6}$alkoxy;

(viii) n=0 or 1;

(ix) when n=1, A is —C($R_{13}R_{14}$)—, wherein $R_{13}$ and $R_{14}$ are, independently, H or $C_{1-4}$alkyl, aryl, heteroaryl, (optionally hetero)aryl$C_{1-4}$alkoxy, (optionally hetero)aryl$C_{1-4}$alkyl or $R_{14}$ can form a bridge with $R_2$ or $R_4$;

(x) $R_{15}$ is —OH or —O$C_{1-4}$alkyl (e.g., —$OCH_3$);

(xi) $R_{16}$ and $R_{17}$ are independently H or $C_{1-4}$alkyl;

(xii) $R_{18}$ and $R_{19}$ are independently H, $C_{1-4}$alky (e.g., methyl, ethyl, n-propyl, isobutyl), $C_{3-8}$cycloalky (e.g., cyclohexyl or cyclopenyl), hetero$C_{3-8}$cycloalky (e.g., pyrrolidinyl, piperidinyl, morpholinyl), aryl (e.g., phenyl) or heteroaryl, wherein said aryl and heteroaryl are optionally substituted with one or more halo (e.g., fluorophenyl, e.g., 4-fluorophenyl), hydroxy (e.g., hydroxyphenyl, e.g., 4-hydroxyphenyl or 2-hydroxyphenyl)

$C_{1-4}$alkyl (e.g., methyl), halo$C_{1-4}$alkyl (e.g., trifluoromethyl), $C_{1-4}$carboxy, or an additional aryl, heteroaryl (e.g., biphenyl or pyridylphenyl) or $C_{3-8}$cycloalkyl;

(xiii) $R_{20}$ is H, $C_{1-4}$alkyl or $C_{3-7}$cycloalkyl;

in free or salt form.

In still another embodiment, the Compound of the Invention is a Compound of Formula I-A, I-B, II-A or II-B, wherein:

(i) Q is C(=O), C(=S), C(=N($R_{20}$)) or CH$_2$;
(ii) L is a single bond, —CH$_2$—, —N(H)—, —S—, —S(O)— or —S(O$_2$)—;
(iii) $R_1$ is H or $C_{1-4}$ alkyl (e.g., methyl);
(iv) $R_4$ is H or $C_{1-6}$ alkyl (e.g., methyl or isopropyl) and $R_2$ and $R_3$ are, independently,
H
$C_{1-6}$alkyl (e.g., methyl, isopropyl) optionally substituted with halo or hydroxy (e.g., $R_2$ and $R_3$ are both methyl, or $R_2$ is H and $R_3$ is methyl, ethyl, isopropyl or hydroxyethyl),
aryl,
heteroaryl,
(optionally hetero)arylalkoxy,
(optionally hetero)aryl$C_{1-6}$alkyl, or
$R_2$ and $R_3$ together form a 3- to 6-membered ring;
or
$R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(v) $R_5$ is attached to the nitrogen on the pyrrolo portion of Formula I-A, I-B, II-A or II-B and is a moiety of Formula A

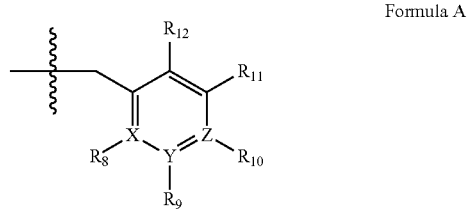

Formula A wherein X, Y and Z are, independently, N or C, and $R_8$, $R_9$, $R_{11}$ and $R_{12}$ are independently H or halogen (e.g., Cl or F), and $R_{10}$ is halogen,
$C_{1-4}$alkyl,
halo$C_{1-4}$alkyl (e.g., triflouromethyl)
$C_{1-4}$alkoxy (e.g. methoxy),
$C_{3-7}$cycloalkyl,
hetero$C_{3-7}$cycloalkyl (e.g., pyrrolidinyl or piperidinyl),
$C_{1-4}$haloalkyl (e.g., trifluoromethyl),
aryl (e.g., phenyl),
heteroaryl (e.g., pyridyl (for example pyrid-2-yl or pyrid-4-yl), or thiadiazolyl (e.g., 1,2,3-thiadiazol-4-yl)), diazolyl (e.g., imidazol-1-yl), triazolyl (e.g., 1,2,4-triazol-1-yl), tetrazolyl,
arylcarbonyl (e.g., benzoyl),
alkylsulfonyl (e.g., methylsulfonyl),
heteroarylcarbonyl, or
alkoxycarbonyl;
wherein the aryl, heteroaryl, cycloalkyl or heterocycloalkyl is independently, optionally substituted with one or more $C_{1-4}$alkyl (e.g., methyl), halogen (e.g., chloro or fluoro), halo$C_{1-4}$alkyl (e.g., trifluoromethyl), hydroxy, $C_{1-4}$carboxy, —SH or an additional aryl or heteroaryl (e.g., biphenyl or pyridylphenyl),
provided that when X, Y, or Z is nitrogen, $R_8$, $R_9$, or $R_{10}$, respectively, is not present;

(vi) $R_6$ is
H,
$C_{1-4}$alkyl (e.g., methyl, ethyl, n-propyl, isobutyl),
$C_{3-7}$cycloalkyl (e.g., cyclopentyl or cyclohexyl),
hetero$C_{3-7}$cycloalkyl (e.g., pyrrolidinyl, piperidinyl, morpholinyl),
aryl (e.g., phenyl),
heteroaryl (e.g., pyrid-4-yl),
aryl$C_{1-4}$alkyl (e.g., benzyl),
wherein the aryl and heteroaryl are optionally substituted with one or more $C_{1-4}$alkyl (e.g., methyl), halogen (e.g., chloro or fluoro), halo$C_{1-4}$alkyl (e.g., trifluoromethyl), hydroxy, $C_{1-4}$carboxy, or an additional aryl, heteroaryl (e.g., biphenyl or pyridylphenyl) or $C_{3-8}$cycloalkyl;
when L is a single bond, —CH$_2$—, —N(H)—, —S—, —S(O)— or S(O$_2$)—,
or
$R_6$ is
H,
arylamino (e.g., phenylamino),
heteroarylamino,
N,N-di$C_{1-4}$alkylamino,
N,N-diarylamino,
N-aryl-N-(aryl$C_{1-4}$alkyl)amino (e.g., N-phenyl-N-(1,1'-biphen-4-ylmethyl)amino), or
—N($R_{18}$)($R_{19}$),
wherein the aryl and heteroaryl are optionally substituted with one or more $C_{1-4}$alkyl (e.g., methyl), halogen (e.g., chloro or fluoro), halo$C_{1-4}$alkyl (e.g., trifluoromethyl), hydroxy, $C_{1-4}$carboxy, or an additional aryl, heteroaryl (e.g., biphenyl or pyridylphenyl) or $C_{3-8}$cycloalkyl;
when L is a single bond or —CH$_2$—;
(vii) $R_7$ is H, $C_{1-6}$alkyl (e.g., methyl or ethyl), halogen (e.g., Cl), —N($R_{18}$)($R_{19}$), hydroxy or $C_{1-6}$alkoxy;
(viii) n=0 or 1;
(ix) when n=1, A is —C($R_{13}R_{14}$)—, wherein $R_{13}$ and $R_{14}$, are, independently, H or $C_{1-4}$alkyl, aryl, heteroaryl, (optionally hetero)aryl$C_{1-4}$alkoxy, (optionally hetero)aryl$C_{1-4}$alkyl or $R_{14}$ can form a bridge with $R_2$ or $R_4$;
(x) $R_{18}$ and $R_{19}$ are independently H, $C_{1-4}$alkyl (e.g., methyl, ethyl, n-propyl, isobutyl), $C_{3-8}$cycloalky (e.g., cyclohexyl or cyclopenyl), hetero$C_{3-8}$cycloalky (e.g., pyrrolidinyl, piperidinyl, morpholinyl), aryl (e.g., phenyl) or heteroaryl, wherein said aryl and heteroaryl are optionally substituted with one or more halo (e.g., fluorophenyl, e.g., 4-fluorophenyl), hydroxy (e.g., hydroxyphenyl, e.g., 4-hydroxyphenyl or 2-hydroxyphenyl) $C_{1-4}$alkyl (e.g., methyl), halo$C_{1-4}$alkyl (e.g., trifluoromethyl), $C_{1-4}$carboxy, or an additional aryl, heteroaryl (e.g., biphenyl or pyridylphenyl) or $C_{3-8}$cycloalkyl;
(xi) $R_{20}$ is H, $C_{1-4}$alkyl or $C_{3-7}$cycloalkyl;
in free or salt form.

In yet another embodiment, the Compound of the Invention is a Compound of Formula I-A, I-B, II-A or II-B, wherein:
(i) Q is C(=O), C(=S), C(=N($R_{20}$)) or CH$_2$;
(ii) L is —N(H)—, —S—, —S(O)— or —S(O$_2$)—;
(iii) $R_1$ is H or $C_{1-4}$ alkyl (e.g., methyl);
(iv) $R_4$ is H or $C_{1-6}$ alkyl (e.g., methyl or isopropyl) and $R_2$ and $R_3$ are, independently,

H $C_{1-6}$alkyl (e.g., methyl, isopropyl) optionally substituted with halo or hydroxy (e.g., $R_2$ and $R_3$ are both methyl, or $R_2$ is H and $R_3$ is methyl, ethyl, isopropyl or hydroxyethyl), aryl, heteroaryl, (optionally hetero)arylalkoxy, (optionally hetero)aryl$C_{1-6}$alkyl, or $R_2$ and $R_3$ together form a 3- to 6-membered ring;

or $R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);

(v) $R_5$ is attached to the nitrogen on the pyrrolo portion of Formula I-A, I-B, II-A or II-B and is a moiety of Formula A

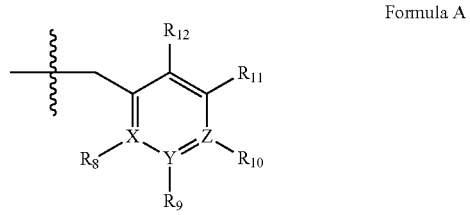

Formula A wherein X, Y and Z are, independently, N or C, and $R_8$, $R_9$, $R_{11}$ and $R_{12}$ are independently H or halogen (e.g., Cl or F), and $R_{10}$ is $C_{1-4}$alkoxy (e.g. methoxy), $C_{3-7}$cycloalkyl, hetero$C_{3-7}$cycloalkyl (e.g., pyrrolidinyl or piperidinyl), aryl (e.g., phenyl), heteroaryl (e.g., pyridyl (for example pyrid-2-yl or pyrid-4-yl), or thiadiazolyl (e.g., 1,2,3-thiadiazol-4-yl)), diazolyl (e.g., imidazol-1-yl), triazolyl (e.g., 1,2,4-triazol-1-yl), tetrazolyl, wherein the aryl, heteroaryl, cycloalkyl or heterocycloalkyl is independently, optionally substituted with one or more $C_{1-4}$alkyl (e.g., methyl), halogen (e.g., chloro or fluoro), halo$C_{1-4}$alkyl (e.g., trifluoromethyl), hydroxy, $C_{1-4}$carboxy, —SH or an additional aryl or heteroaryl (e.g., biphenyl or pyridylphenyl), provided that when X, Y, or Z is nitrogen, $R_8$, $R_9$, or $R_{10}$, respectively, is not present;

(vi) $R_6$ is

H, $C_{1-4}$alkyl (e.g., methyl, ethyl, n-propyl, isobutyl), $C_{3-7}$cycloalkyl (e.g., cyclopentyl or cyclohexyl), hetero$C_{3-7}$cycloalkyl (e.g., pyrrolidinyl, piperidinyl, morpholinyl), aryl (e.g., phenyl), heteroaryl (e.g., pyrid-4-yl), aryl$C_{1-4}$alkyl (e.g., benzyl), wherein the aryl and heteroaryl are optionally substituted with one or more $C_{1-4}$alkyl (e.g., methyl), halogen (e.g., chloro or fluoro), halo$C_{1-4}$alkyl (e.g., trifluoromethyl), hydroxy, $C_{1-4}$carboxy, or an additional aryl, heteroaryl (e.g., biphenyl or pyridylphenyl) or $C_{3-8}$cycloalkyl;

(vii) $R_7$ is H, $C_{1-6}$alkyl (e.g., methyl or ethyl), halogen (e.g., Cl), —N($R_{18}$)($R_{19}$), hydroxy or $C_{1-6}$alkoxy;

(viii) n=0 or 1;

(ix) when n=1, A is —C($R_{13}R_{14}$)—, wherein $R_{13}$ and $R_{14}$, are, independently, H or $C_{1-4}$alkyl, aryl, heteroaryl, (optionally hetero)aryl$C_{1-4}$alkoxy, (optionally hetero)aryl$C_{1-4}$alkyl or $R_{14}$ can form a bridge with $R_2$ or $R_4$;

(x) $R_{18}$ and $R_{19}$ are independently H, $C_{1-4}$alky (e.g., methyl, ethyl, n-propyl, isobutyl), $C_{3-8}$cycloalky (e.g., cyclohexyl or cyclopenyl), hetero$C_{3-8}$cycloalky (e.g., pyrrolidinyl, piperidinyl, morpholinyl), aryl (e.g., phenyl) or heteroaryl, wherein said aryl and heteroaryl are optionally substituted with one or more halo (e.g., fluorophenyl, e.g., 4-fluorophenyl), hydroxy (e.g., hydroxyphenyl, e.g., 4-hydroxyphenyl or 2-hydroxyphenyl) $C_{1-4}$alkyl (e.g., methyl), halo$C_{1-4}$alkyl (e.g., trifluoromethyl), $C_{1-4}$carboxy, or an additional aryl, heteroaryl (e.g., biphenyl or pyridylphenyl) or $C_{3-8}$cycloalkyl;

(xi) $R_{20}$ is H, $C_{1-4}$alkyl or $C_{3-7}$cycloalkyl;

in free or salt form.

If not otherwise specified or clear from context, the following terms herein have the following meanings:

(a) "Alkyl" as used herein is a saturated or unsaturated hydrocarbon moiety, preferably saturated, preferably having one to six carbon atoms, which may be linear or branched, and may be optionally mono-, di- or tri-substituted, e.g., with halogen (e.g., chloro or fluoro), hydroxy, or carboxy.

(b) "Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy. Wherein the cycloalkyl optionally contains one or more atoms selected from N and O and/or S, said cycloalkyl may also be a heterocycloalkyl.

(c) "Heterocycloalkyl" is, unless otherwise indicated, saturated or unsaturated nonaromatic hydrocarbon moiety, preferably saturated, preferably comprising three to nine carbon atoms, at least some of which form a nonaromatic mono- or bicyclic, or bridged cyclic structure, wherein at least one carbon atom is replaced with N, O or S, which heterocycloalkyl may be optionally substituted, e.g., with halogen (e.g., chloro or fluoro), hydroxy, or carboxy.

(d) "Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

(e) "Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.

(f) For ease of reference, the atoms on the pyrazolo-pyrimidine core of the Compounds of the Invention are numbered in accordance with the numbering depicted in Formula I, unless otherwise noted.

(g) Wherein E is phenylene, the numbering is as follows:

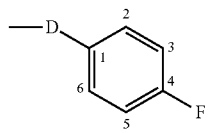

(h) It is intended that wherein the substitutents end in "ene", for example, alkylene, phenylene or arylalkylene, said substitutents are intended to bridge or be connected to two other substituents. Therefore, methylene is intended to be —$CH_2$— and phenylene intended to be —$C_6H_4$— and arylalkylene is intended to be —$C_6H_4$—$CH_2$— or —$CH_2$—$C_6H_4$—.

(i) The Compounds of the Invention are intended to be numbered as follows:

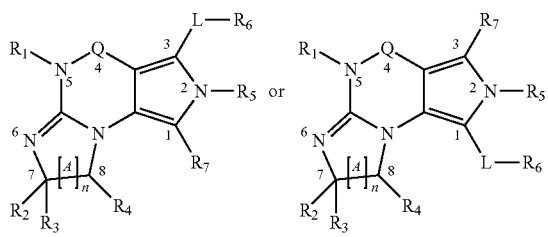

Compounds of the Invention, e.g., substituted 4,5,7,8-tetrahydro-2H-imidazo[1,2-a]pyrrolo[3,4-e]pyrimidine or 4,5,7,8,9-pentahydro-2H-pyrimido[1,2-a]pyrrolo[3,4-e]pyrimidine, e.g., Compounds of Formula I (Formula I-A and I-B), e.g., any of formulae 1.1-1.84, or a Compound of Formula II (e.g., II-A or II-B), any of formulae 2.1-2.13 may exist in free or salt form, e.g., as acid addition salts. In this specification unless otherwise indicated, language such as "Compounds of the Invention" is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included.

Compounds of the Invention may in some cases also exist in prodrug form. A prodrug form is compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. Therefore, wherein the Compound of the Invention contains a hydroxy group, for example, Compound-OH, the acyl ester prodrug of such compound, i.e., Compound-O—C(O)—$C_{1-4}$ alkyl, can hydrolyze in the body to form physiologically hydrolysable alcohol (Compound-OH) on the one hand and acid on the other (e.g., HOC(O)—$C_{1-4}$alkyl). Alternatively, wherein the Compound of the Invention contains a carboxylic acid, for example, Compound-C(O)OH, the acid ester prodrug of such compound, Compound-C(O)O—$C_{1-4}$alkyl can hydrolyze to form Compound-C(O)OH and HO—$C_{1-4}$alkyl. As will be appreciated the term thus embraces conventional pharmaceutical prodrug forms.

The invention also provides methods of making the Compounds of the Invention and methods of using the Compounds of the Invention for treatment of diseases and disorders as set forth below (especially treatment of diseases characterized by reduced dopamine D1 receptor signaling activity, such as Parkinson's disease, Tourette's Syndrome, Autism, fragile X syndrome, ADHD, restless leg syndrome, depression, cognitive impairment of schizophrenia, narcolepsy and diseases that may be alleviated by the enhancement of progesterone-signaling such as female sexual dysfunction, or a disease or disorder such as psychosis or glaucoma). This list is not intended to be exhaustive and may include other diseases and disorders as set forth below.

In another embodiment, the invention further provides a pharmaceutical composition comprising a Compound of the Invention, in free, pharmaceutically acceptable salt or prodrug form, in admixture with a pharmaceutically acceptable carrier.

DETAILED DESCRIPTION OF THE INVENTION

Methods of Making Compounds of the Invention

The compounds of the Invention and their pharmaceutically acceptable salts may be made using the methods as described and exemplified herein and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds. Various starting materials and/or Compounds of the Invention may be prepared using methods described in WO 2006/133261 and PCT/US2007/070551. All references cited herein are hereby incorporated by reference in their entirety.

The Compounds of the Invention include their enantiomers, diastereoisomers and racemates, as well as their polymorphs, hydrates, solvates and complexes. Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

It is also intended that the Compounds of the Invention encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Invention may be replaced with deuterium (a stable isotope which is non-raradioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}I$, $^{131}I$, $^{125}I$, $^{11}C$, $^{18}F$, may replace the corresponding abundant species of I, C and F. Another example of useful isotope of the compound of the invention is the $^{11}C$ isotope. These radio isotopes are useful for radio-imaging and/or pharmacokinetic studies of the compounds of the invention.

Melting points are uncorrected and (dec) indicates decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks Solvent mixture compositions are given as volume percentages or volume ratios. In cases where the NMR spectra are complex, only diagnostic signals are reported.

Terms and Abbreviations:
BuLi=n-butyllithium
Bu$^t$OH=tert-butyl alcohol,
CAN=ammonium cerium (IV) nitrate,
DIPEA=diisopropylethylamine,
DMF=N,N-dimethylforamide,
DMSO=dimethyl sulfoxide,
Et$_2$O=diethyl ether,
EtOAc=ethyl acetate,
equiv.=equivalent(s),
h=hour(s),
HPLC=high performance liquid chromatography,
LDA=lithium diisopropylamide
MeOH=methanol,
NBS=N-bromosuccinimide
NCS=N-chlorosuccinimide
NaHCO$_3$=sodium bicarbonate,
NH$_4$OH=ammonium hydroxide,
Pd$_2$(dba)$_3$=tris[dibenzylideneacetone]dipalladium(0)
PMB=p-methoxybenzyl,
POCl$_3$=phosphorous oxychloride,
SOCl$_2$=thionyl chloride,
TFA=trifluoroacetic acid,
THF=tetrahedrofuran.

The synthetic methods in this invention are illustrated below. The significances for the R groups are as set forth above for formula I unless otherwise indicated.

In an aspect of the invention, Compounds (I)-A and (I)-B may be formed by reacting a compound of 1-A and 1-B respectively with for example a R$_5$—X in a solvent such as DMF and a base such as K$_2$CO$_3$ at room temperature or with heating:

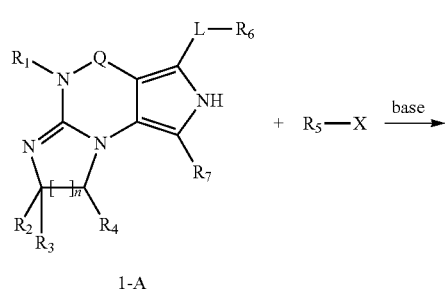

1-A

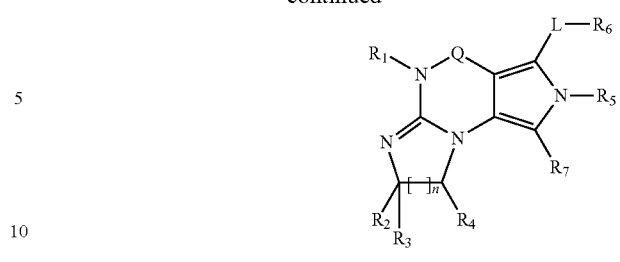

1-B

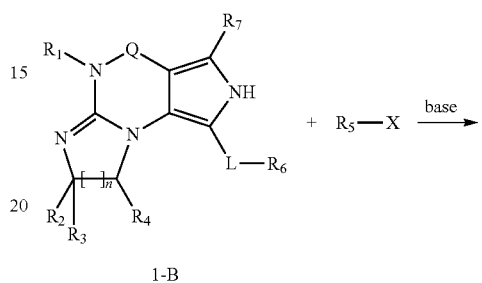

(I)-A

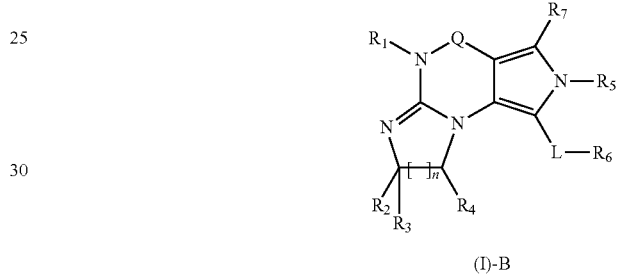

(I)-B wherein all the substitutents are as defined previously in Formula I-A, I-B, II-A or II-B above; X is a leaving group such as a halogen, mesylate, or tosylate.

Alternatively, compounds I-A, I-B, II-A and II-B, wherein L is —N(H)—, —S—, —S(O)— or S(O)$_2$— may be synthesized by reacting a compound of 1-C and 1-D respectively with for example a R$_6$-L-H in a solvent such as DMF or in neat condition with heating:

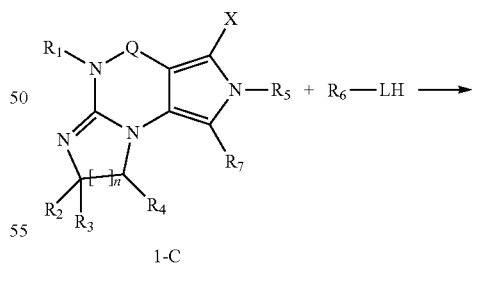

1-C

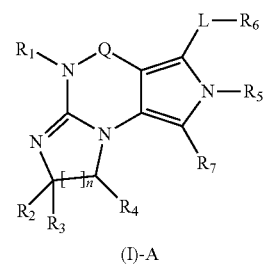

(I)-A

-continued

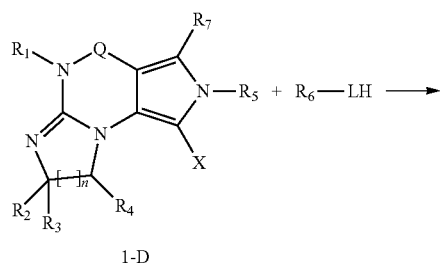

1-D

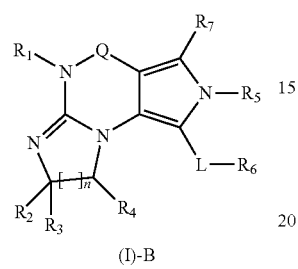

(I)-B wherein all the other substituents are as defined previously in Formula I-A, I-B, II-A or II-B above; X is a leaving group such as a halogen group.

Compound 1-C, e.g., wherein Q is C(=O) and X is a chloro group, may be prepared by, e.g., reacting compound 1-E with a chlorinating reagent such as hexachloroethane in the presence of a strong base or lithium reagent such as LiHMDS. Compound 1-D, e.g., wherein Q is C(=O) and X is a chloro group, may be prepared by, e.g., reacting compound 1-F with a chlorinating reagent such NCS (N-chlorosuccinimide) in a solvent such as CCl$_4$. Sometimes, when R$_5$ is H, a protective group such as a para-methoxybenzyl (PMB) group may be added prior to the reaction. Under this circumstance, compound 1-C or 1-D with the PMB at the pyrrolo nitrogen can be deprotected using a reagent such as TFA/TFMSA, and then reacts the resulting (deprotected pyrrolo compound) with R$_5$X wherein X is a leaving group such as a halogen, mesylate or tosylate, under basic conditions to yield 1-C or 1-D analogs.

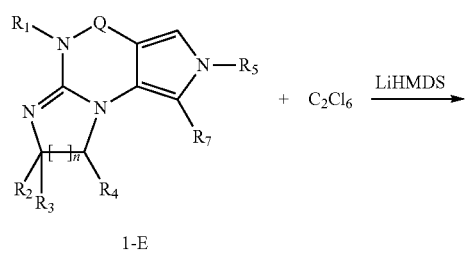

1-E

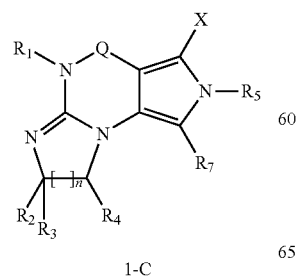

1-C

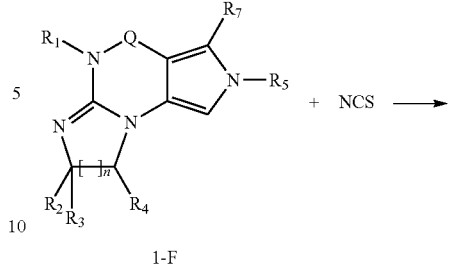

1-F

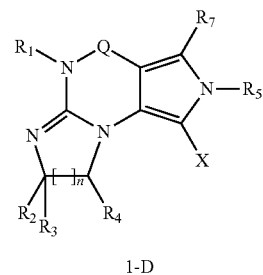

1-D

Compounds (I)-E and (I)-F may be formed by reacting a compound of 1-G and 1-H respectively with for example a R$_5$—X in a solvent such as DMF and a base such as K$_2$CO$_3$ at room temperature or with heating:

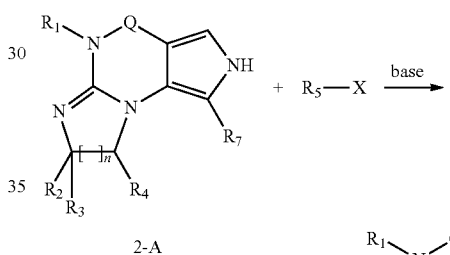

2-A

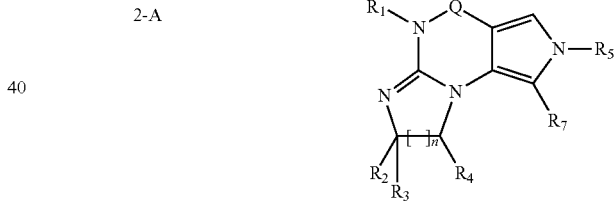

1-E

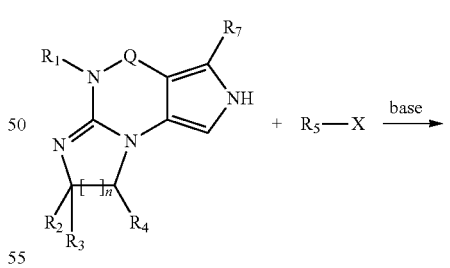

2-B

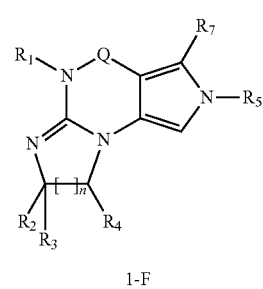

1-F wherein all the substituents are as defined previously in Formula I-A, I-B, II-A or II-B; X is a leaving group such as a halogen group, mesylate or tosylate.

Intermediate 2, e.g., wherein Q is C(=O) may be prepared by, e.g., reacting Intermediate 3 with sodium hydride and para-toluenesulfonylmethyl isocyanide.

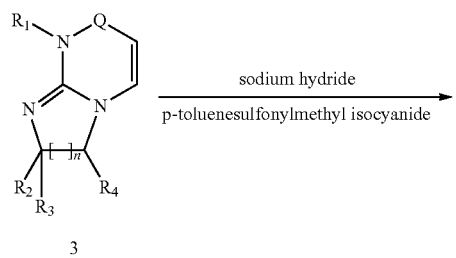

Alternatively and preferably, Intermediate 2, e.g., wherein Q is C(=O) is prepared by, e.g., reacting Intermediate 3 with a strong base such as sodium hydride and a reagent such as TsCHR₇NC in a solvent such as THF:

Intermediate 3 may be prepared by, e.g., reacting Intermediate 4 with diethyl azodicarboxylate in the presence of triphenylphosphine.

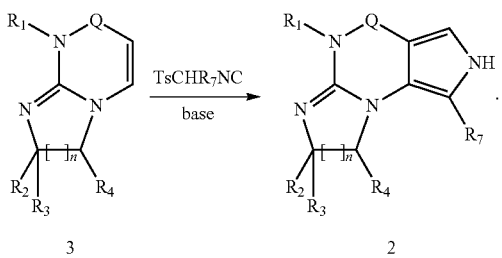

Alternatively and preferably, Intermediate 3 may be prepared by, e.g., reacting Intermediate 4 with a dehydrating reagent such as diethyl azodicarboxylate in the presence of phosphine ligand such as triphenylphosphine.

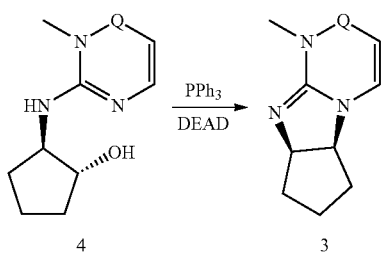

Intermediate 4 may, in turn be made as similarly disclosed in WO 2006/133261, e.g., by reacting a compound of 5-A with an amino alcohol, e.g., (1R,2R)-(−)-2-hydroxycyclopentylamine hydrochloride, e.g., in the presence of, for example, DBU (1,8-Diazabicyclo[5.4.0]undec-7-ene).

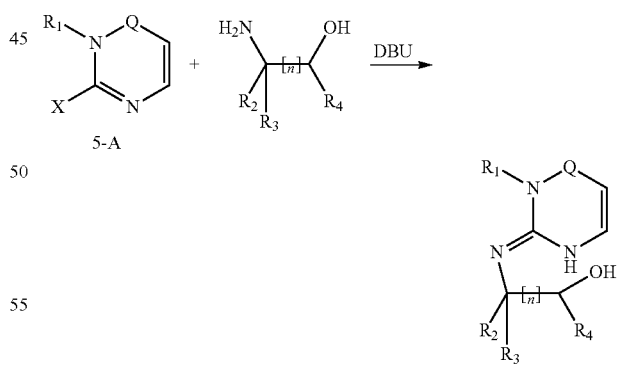

wherein all the substituents are as defined previously; X is a leaving group such as a halogen or methylthio group.

Alternatively and preferably, Intermediate 4 is prepared, e.g., by reacting a compound of 5-A with an amino alcohol in the presence of a strong base, for example, DBU (1,8-Diazabicyclo[5.4.0]undec-7-ene), wherein all the substituents are as defined previously; X is a leaving group such as a halogen or methylthio group.

Still alternatively, intermediate 4 may be made, e.g., by reacting a compound of 5-B with an amino alcohol in the presence of a strong base, for example, DBU (1,8-Diazabicyclo[5.4.0]undec-7-ene) and a coupling reagent such as BOP at room temperature.

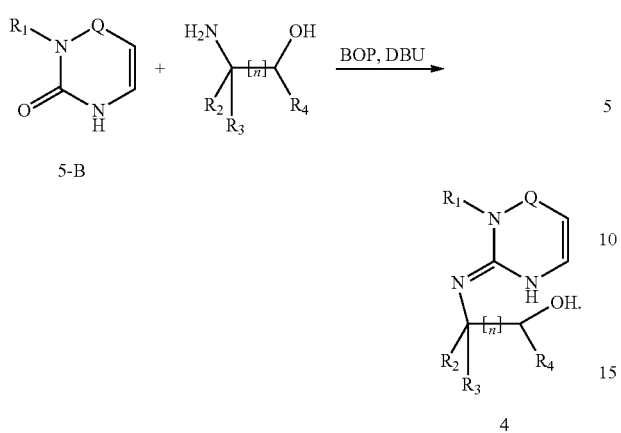

Intermediate 6 wherein X is halo, e.g., Cl, can be prepared by reacting halogenating Compound 7, e.g., reacting Compound 7 with, e.g., N-chlorosuccinimide, N-bromosuccinimide, or I$_2$ in the presence of, e.g., carbontetrachloride in a solvent such as DMF.

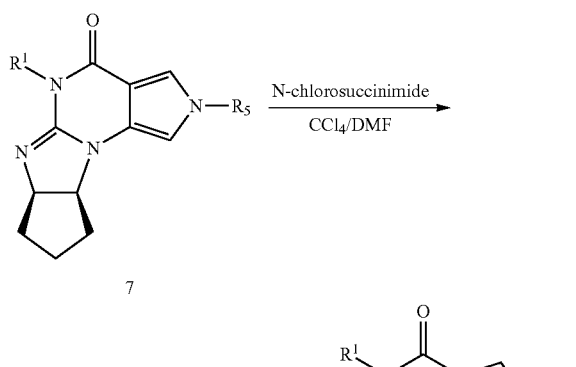

Compound 8 may be formed by reacting a compound of 9 with for example an amine such as aniline in the present of, e.g., TFA.

The thione compounds of the invention, e.g., Compounds of Formula I-A or I-B or II-A or II-B wherein Q is C(=S) may then be prepared by reacting the Compounds of the Invention wherein Q is C(=O) with P$_4$S$_{10}$ in a microwave vial in the presence of a base, e.g., pyridine, and heating the mixture to an elevated temperature, e.g., in a microwave, e.g., to about 150° C. The imine compounds of the Invention, e.g., Compounds of Formula I-A or I-B or II-A or II-B wherein Q is C(=N(R$_{20}$)) may in turn be converted from the thione derivative (i.e., Compounds of Formula I-A or I-B or II-A or II-B wherein with Q is C(=S) by reacting the thione derivative with NH$_2$(R$_{20}$) in the presence of HgCl$_2$, e.g., in a solvent such as THF, and heating the reaction mixture to an elevated temperature, e.g., in a microwave, e.g., to about 110° C.

The Compounds of the Invention, e.g., Compounds of Formula I-A or I-B or II-A or II-B wherein Q is C(R$_{14}$)(R$_{15}$) may also be prepared by reacting the ketone derivative, e.g., Formula I-A or I-B or II-A or II-B wherein Q is C(=O), with a reducing agent, e.g., diisobutylaluminum hydride (DIBAL-H), lithium aluminum hydride, sodium borohydride, preferably, DIBAL-H.

Wherein L of the compounds of the invention is —S— (thiol) or Compound (I)-C, these compounds may be prepared by reacting Compound (IVb), e.g., with phenyl disulfide and lithium bis(trimethylsilyl)azanide (LiHMDS).

wherein R$_6$ is phenyl.

Alternatively and preferably, wherein L of the compounds of the invention is —S— (thiol) or Compound (I)-C, these compounds may be prepared by reacting Compound 1-G, with a disulfide in the presence of a base such as lithium bis(trimethylsilyl)azanide (LiHMDS).

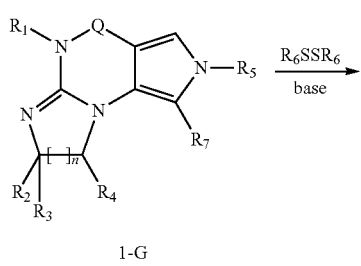

1-G

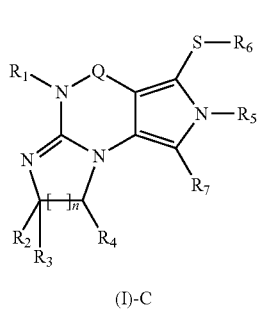

(I)-C

The sulfinyl derivatives of the Invention, e.g., Formula I wherein L is SO or SO₂ may be prepared by the oxidation of (I)-C using a oxidizing reagent such as oxone or a peroxide in a solvent such as acetonitrile and methanol.

The invention thus provides methods of making Compounds of Formula I-A, I-B or II-A or II-B, for example, comprising (i) reacting Intermediate 1-A or 1-B with a compound of formula R₅—X wherein X is a leaving group, e.g., halogen, mesylate, or tosylate, R₅ is as defined above in Formula I, e.g., under basic conditions, for example:

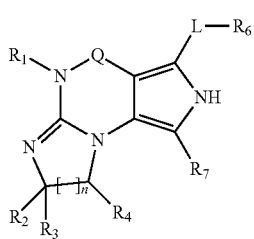

1-A

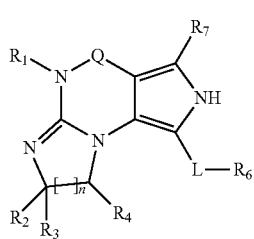

1-B

Methods of Using Compounds of the Invention

The Compounds of the Invention, any of the compounds disclosed herein e.g., any of Compounds of Formula I-A, I-B, e.g., any of 1.1-1.84, or Formula II-A or II-B, e.g., any of 2.1-2.13, in free or salt form are useful in the treatment of diseases characterized by disruption of or damage to cAMP and cGMP mediated pathways, e.g., as a result of increased expression of PDE1 or decreased expression of cAMP and cGMP due to inhibition or reduced levels of inducers of cyclic nucleotide synthesis, such as dopamine and nitric oxide (NO). By preventing the degradation of cAMP and cGMP by PDE1B, thereby increasing intracellular levels of cAMP and cGMP, the Compounds of the Invention potentiate the activity of cyclic nucleotide synthesis inducers.

The invention provides methods of treatment of any one or more of the following conditions:

(i) Neurodegenerative diseases, including Parkinson's disease, restless leg, tremors, dyskinesias, Huntington's disease, Alzheimer's disease, and drug-induced movement disorders;

(ii) Mental disorders, including depression, attention deficit disorder, attention deficit hyperactivity disorder, bipolar illness, anxiety, sleep disorders, e.g., narcolepsy, cognitive impairment, dementia, Tourette's syndrome, autism, fragile X syndrome, psychostimulant withdrawal, and drug addiction;

(iii) Circulatory and cardiovascular disorders, including cerebrovascular disease, stroke, congestive heart disease, hypertension, pulmonary hypertension, and sexual dysfunction;

(iv) Respiratory and inflammatory disorders, including asthma, chronic obstructive pulmonary disease, and allergic rhinitis, as well as autoimmune and inflammatory diseases;

(v) Any disease or condition characterized by low levels of cAMP and/or cGMP (or inhibition of cAMP and/or cGMP signaling pathways) in cells expressing PDE1; and/or (vi) Any disease or condition characterized by reduced dopamine D1 receptor signaling activity, comprising administering an effective amount of a Compound of the Invention, e.g., a compound according to any of Formula I or 1.1-1.84, in free, pharmaceutically acceptable salt or prodrug form, to a human or animal patient in need thereof. In another aspect, the invention provides a method of treatment of the conditions disclosed above comprising administering a therapeutically effective amount of a Compound of Formula II-A or II-B, e.g., any of 2.1-2.13, in free or salt in free or pharmaceutically acceptable salt form, or a composition comprising the same, to a human or animal patient in need thereof.

In an especially preferred embodiment, the invention provides methods of treatment or prophylaxis for narcolepsy. In this embodiment, PDE 1 Inhibitors may be used as a sole therapeutic agent, but may also be used in combination or for co-administration with other active agents. Thus, the invention further comprises a method of treating narcolepsy comprising administering simultaneously, sequentially, or contemporaneously administering therapeutically effective amounts of (i) a PDE 1 Inhibitor, e.g., a compound according to any of Formula I or any of 1.1-0, and (ii) a compound to promote wakefulness or regulate sleep, e.g., selected from (a) central nervous system stimulants-amphetamines and amphetamine like compounds, e.g., methylphenidate, dextroamphetamine, methamphetamine, and pemoline; (b) modafinil, (c) antidepressants, e.g., tricyclics (including imipramine, desipramine, clomipramine, and protriptyline) and selective serotonin reuptake inhibitors (including fluoxetine and sertraline); and/or (d) gamma hydroxybutyrate (GHB).

in free or pharmaceutically acceptable salt form, to a human or animal patient in need thereof. In still another embodiment, the methods of treatment or prophylaxis for narcolepsy as hereinbefore described, comprises administering a therapeutically effective amount of a Compound of Formula II-A or II-B, or any of Formula 2.1-2.13, in free or pharmaceutically acceptable salt form, as a sole therapeutic agent or use in combination for co-administered with another active agent.

In another embodiment, the invention further provides methods of treatment or prophylaxis of a condition which may be alleviated by the enhancement of the progesterone signaling comprising administering an effective amount of a Compound of the Invention, e.g., a compound according to any of Formula I, or any of 1.1-1.84, in free, pharmaceutically acceptable salt or prodrug form, to a human or animal patient in need thereof. The invention also provides methods of treatment as disclosed here, comprising administering a therapeutically effective amount of a Compound of Formula II-A or II-B, e.g., any of formulae 2.1-2.13, in free or pharmaceutically acceptable salt form. In still another embodiment, the invention further provides methods of treatment or prophylaxis of a condition which may be alleviated by the enhancement of the progesterone signaling comprising administering an effective amount of a Compound of the Invention, e.g., a compound according to any of Formula I, or any of 1.1-1.84, in free, pharmaceutically acceptable salt or prodrug form, to a human or animal patient in need thereof. In another aspect, the invention provides methods of treatment as disclosed herein, comprising administering an effective amount of a Compound of the Invention, e.g., a compound according to any of Formula II-A or II-B, e.g., e.g., any of formulae 2.1-2.13, in free or pharmaceutically acceptable salt form. Disease or condition that may be ameliorated by enhancement of progesterone signaling include, but are not limited to, female sexual dysfunction, secondary amenorrhea (e.g., exercise amenorrhoea, anovulation, menopause, menopausal symptoms, hypothyroidism), pre-menstrual syndrome, premature labor, infertility, for example infertility due to repeated miscarriage, irregular menstrual cycles, abnormal uterine bleeding, osteoporosis, autoimmmune disease, multiple sclerosis, prostate enlargement, prostate cancer, and hypothyroidism. For example, by enhancing progesterone signaling, the PDE 1 inhibitors may be used to encourage egg implantation through effects on the lining of uterus, and to help maintain pregnancy in women who are prone to miscarriage due to immune response to pregnancy or low progesterone function. The novel PDE 1 inhibitors, e.g., as described herein, may also be useful to enhance the effectiveness of hormone replacement therapy, e.g., administered in combination with estrogen/estradiol/estriol and/or progesterone/progestins in postmenopausal women, and estrogen-induced endometrial hyperplasia and carcinoma. The methods of the invention are also useful for animal breeding, for example to induce sexual receptivity and/or estrus in a nonhuman female mammal to be bred.

In this embodiment, PDE 1 Inhibitors may be used in the foregoing methods of treatment or prophylaxis as a sole therapeutic agent, but may also be used in combination or for co-administration with other active agents, for example in conjunction with hormone replacement therapy. Thus, the invention further comprises a method of treating disorders that may be ameliorated by enhancement of progesterone signaling comprising administering simultaneously, sequentially, or contemporaneously administering therapeutically effective amounts of
  (i) a PDE 1 Inhibitor, e.g., a compound according to any of Formula I-A or I-B or any of 1.1-1.84, and
  (ii) a hormone, e.g., selected from estrogen and estrogen analogues (e.g., estradiol, estriol, estradiol esters) and progesterone and progesterone analogues (e.g., progestins)
in free or pharmaceutically acceptable salt form, to a human or animal patient in need thereof. In another embodiment, the invention provides the method described above wherein the PDE 1 inhibitor is a Compound of Formula II-A or II-B, e.g., any of formulae 2.1-2.13, in free or pharmaceutically acceptable salt form.

The invention also provides a method for enhancing or potentiating dopamine D1 intracellular signaling activity in a cell or tissue comprising contacting said cell or tissue with an amount of a Compound of the Invention, e.g., Formula I-A or I-B or any of 1.1-1.84, sufficient to inhibit PDE1B activity. The invention further provides a method for enhancing or potentiating dopamine D1 intracellular signaling activity in a cell or tissue comprising contacting said cell or tissue with an amount of a Compound of Formula II-A or II-B or any of 2.1-2.13, in free or salt form.

The invention also provides a method for treating a PDE1-related, especially PDE1B-related disorder, a dopamine D1 receptor intracellular signaling pathway disorder, or disorders that may be alleviated by the enhancement of the progesterone signaling pathway in a patient in need thereof comprising administering to the patient an effective amount of a Compound of the Invention, e.g., Formula I, e.g., Formula I-A or I-B or any of 1.1-1.84, that inhibits PDE1B, wherein PDE1B activity modulates phosphorylation of DARPP-32 and/or the GluR1 AMPA receptor. Similarly, the invention provides a method for treating a PDE1-related, especially PDE1B-related disorder, a dopamine D1 receptor intracellular signaling pathway disorder, or disorders that may be alleviated by the enhancement of the progesterone signaling pathway in a patient in need thereof comprising administering to the patient an effective amount of a Compound of Formula II, e.g., II-A or II-B or any of 2.1-2.13, in free or pharmaceutically acceptable salt form.

"The Compound of the Invention" referred to above includes a Compound of Formula I-A or I-B, e.g., any of 1.1-1.84, or a Compound of Formula II-A or II-B, e.g., any of 2.1-2.13, in free or pharmaceutically acceptable salt form.

In another aspect, the invention also provides a method for the treatment for glaucoma or elevated intraocular pressure comprising topical administration of a therapeutically effective amount of a phospodiesterase type I (PDE1) Inhibitor of the Invention, e.g., a Compound of Formula I-A or I-B, e.g., any of 1.1-1.84, or a Compound of Formula II-A or II-B, e.g., any of 2.1-2.13, in free or pharmaceutically acceptable salt form, in an opthalmically compatible carrier to the eye of a patient in need thereof. However, treatment may alternatively include a systemic therapy. Systemic therapy includes treatment that can directly reach the bloodstream, or oral methods of administration, for example.

The invention further provides a pharmaceutical composition for topical ophthalmic use comprising a PDE1 inhibitor; for example an ophthalmic solution, suspension, cream or ointment comprising a PDE1 Inhibitor of the Invention, e.g., a Compound of Formula I-A or I-B, e.g., any of 1.1-1.84, or a Compound of Formula II-A or II-B, e.g., any of 2.1-2.13, in free or ophthamalogically acceptable salt form, in combination or association with an ophthamologically acceptable diluent or carrier.

Optionally, the PDE1 inhibitor may be administered sequentially or simultaneously with a second drug useful for treatment of glaucoma or elevated intraocular pressure. Where two active agents are administered, the therapeutically effective amount of each agent may be below the amount needed for activity as monotherapy. Accordingly, a sub-threshold amount (i.e., an amount below the level necessary for efficacy as monotherapy) may be considered therapeutically effective and also may also be referred alternatively as an effective amount. Indeed, an advantage of administering different agents with different mechanisms of action and different side effect profiles may be to reduce the dosage and side effects of either or both agents, as well as to enhance or potentiate their activity as monotherapy.

The invention thus provides the method of treatment of a condition selected from glaucoma and elevated intraocular pressure comprising administering to a patient in need thereof an effective amount, e.g., a subthreshold amount, of an agent known to lower intraocular pressure concomitantly, simultaneously or sequentially with an effective amount, e.g., a subthreshold amount, of a PDE1 Inhibitor of the Invention, e.g., a Compound of Formula I-A or I-B, e.g., any of 1.1-1.84, or a Compound of Formula II-A or II-B, e.g., any of 2.1-2.13, in free or pharmaceutically acceptable salt form, such that amount of the agent known to lower intraocular pressure and the amount of the PDE1 inhibitor in combination are effective to treat the condition.

In one embodiment, one or both of the agents are administered topically to the eye. Thus the invention provides a method of reducing the side effects of treatment of glaucoma or elevated intraocular pressure by administering a reduced dose of an agent known to lower intraocular pressure concomitantly, simultaneously or sequentially with an effective amount of a PDE1 inhibitor. However, methods other than topical administration, such as systemic therapeutic administration, may also be utilized.

The optional additional agent or agents for use in combination with a PDE1 inhibitor may, for example, be selected from the existing drugs comprise typically of instillation of a prostaglandin, pilocarpine, epinephrine, or topical beta-blocker treatment, e.g. with timolol, as well as systemically administered inhibitors of carbonic anhydrase, e.g. acetazolamide. Cholinesterase inhibitors such as physostigmine and echothiopate may also be employed and have an effect similar to that of pilocarpine. Drugs currently used to treat glaucoma thus include, e.g., 1. Prostaglandin analogs such as latanoprost (Xalatan), bimatoprost (Lumigan) and travoprost (Travatan), which increase uveoscleral outflow of aqueous humor. Bimatoprost also increases trabecular outflow.
2. Topical beta-adrenergic receptor antagonists such as timolol, levobunolol (Betagan), and betaxolol, which decrease aqueous humor production by the ciliary body.
3. Alpha$_2$-adrenergic agonists such as brimonidine (Alphagan), which work by a dual mechanism, decreasing aqueous production and increasing uveo-scleral outflow.
4. Less-selective sympathomimetics like epinephrine and dipivefrin (Propine) increase outflow of aqueous humor through trabecular meshwork and possibly through uveoscleral outflow pathway, probably by a beta$_2$-agonist action.
5. Miotic agents (parasympathomimetics) like pilocarpine work by contraction of the ciliary muscle, tightening the trabecular meshwork and allowing increased outflow of the aqueous humour.
6. Carbonic anhydrase inhibitors like dorzolamide (Trusopt), brinzolamide (Azopt), acetazolamide (Diamox) lower secretion of aqueous humor by inhibiting carbonic anhydrase in the ciliary body.
7. Physostigmine is also used to treat glaucoma and delayed gastric emptying.

For example, the invention provides pharmaceutical compositions comprising a PDE1 Inhibitor of the Invention and an agent selected from (i) the prostanoids, unoprostone, latanoprost, travoprost, or bimatoprost; (ii) an alpha adrenergic agonist such as brimonidine, apraclonidine, or dipivefrin and (iii) a muscarinic agonist, such as pilocarpine. For example, the invention provides ophthalmic formulations comprising a PDE-1 Inhibitor of the Invention together with bimatoprost, abrimonidine, brimonidine, timolol, or combinations thereof, in free or ophthamalogically acceptable salt form, in combination or association with an ophthamologically acceptable diluent or carrier. In addition to selecting a combination, however, a person of ordinary skill in the art can select an appropriate selective receptor subtype agonist or antagonist. For example, for alpha adrenergic agonist, one can select an agonist selective for an alpha 1 adrenergic receptor, or an agonist selective for an alpha$_2$ adrenergic receptor such as brimonidine, for example. For a beta-adrenergic receptor antagonist, one can select an antagonist selective for either $\beta_1$, or $\beta_2$, or $\beta_3$, depending on the appropriate therapeutic application. One can also select a muscarinic agonist selective for a particular receptor subtype such as $M_1$-$M_5$.

The PDE 1 inhibitor may be administered in the form of an ophthalmic composition, which includes an ophthalmic solution, cream or ointment. The ophthalmic composition may additionally include an intraocular-pressure lowering agent.

In yet another example, the PDE-1 Inhibitors disclosed may be combined with a subthreshold amount of an intraocular pressure-lowering agent which may be a bimatoprost ophthalmic solution, a brimonidine tartrate ophthalmic solution, or brimonidine tartrate/timolol maleate ophthalmic solution.

In addition to the above-mentioned methods, it has also been surprisingly discovered that PDE1 inhibitors are useful to treat psychosis, for example, any conditions characterized by psychotic symptoms such as hallucinations, paranoid or bizarre delusions, or disorganized speech and thinking, e.g., schizophrenia, schizoaffective disorder, schizophreniform disorder, psychotic disorder, delusional disorder, and mania, such as in acute manic episodes and bipolar disorder. Without intending to be bound by any theory, it is believed that typical and atypical antipsychotic drugs such as clozapine primarily have their antagonistic activity at the dopamine D2 receptor. PDE1 inhibitors, however, primarily act to enhance signaling at the dopamine D1 receptor. By enhancing D1 receptor signaling, PDE1 inhibitors can increase NMDA receptor function in various brain regions, for example in nucleus accumbens neurons and in the prefrontal cortex. This enhancement of function may be seen for example in NMDA receptors containing the NR2B subunit, and may occur e.g., via activation of the Src and protein kinase A family of kinases.

Therefore, the invention provides a new method for the treatment of psychosis, e.g., schizophrenia, schizoaffective disorder, schizophreniform disorder, psychotic disorder, delusional disorder, and mania, such as in acute manic episodes and bipolar disorder, comprising administering a therapeutically effective amount of a phosphodiesterase-1 (PDE1) Inhibitor of the Invention, e.g., a Compound of Formula I-A or I-B, e.g., any of 1.1-1.84, or a Compound of Formula II-A or II-B, e.g., any of 2.1-2.13, in free or pharmaceutically acceptable salt form, to a patient in need thereof.

PDE 1 Inhibitors may be used in the foregoing methods of treatment prophylaxis as a sole therapeutic agent, but may also be used in combination or for co-administration with other active agents. Thus, the invention further comprises a method of treating psychosis, e.g., schizophrenia, schizoaffective disorder, schizophreniform disorder, psychotic disorder, delusional disorder, or mania, comprising administering simultaneously, sequentially, or contemporaneously administering therapeutically effective amounts of:
(i) a PDE 1 Inhibitor of the invention, e.g., a a Compound of Formula I-A or I-B, e.g., any of 1.1-1.84, or a Com pound of Formula II-A or II-B, e.g., any of 2.1-2.13, in free or pharmaceutically acceptable salt form; and (ii) an antipsychotic, e.g., Typical antipsychotics, e.g., Butyrophenones, e.g. Haloperidol (Haldol, Serenace), Droperidol (Droleptan);

Phenothiazines, e.g., Chlorpromazine (Thorazine, Largactil), Fluphenazine (Prolixin), Perphenazine (Trilafon), Prochlorperazine (Compazine), Thioridazine (Mellaril, Melleril), Trifluoperazine (Stelazine), Mesoridazine, Periciazine, Promazine, Triflupromazine (Vesprin), Levomepromazine (Nozinan), Promethazine (Phenergan), Pimozide (Orap);

Thioxanthenes, e.g., Chlorprothixene, Flupenthixol (Depixol, Fluanxol), Thiothixene (Navane), Zuclopenthixol (Clopixol, Acuphase);

Atypical antipsychotics, e.g.,

Clozapine (Clozaril), Olanzapine (Zyprexa), Risperidone (Risperdal), Quetiapine (Seroquel), Ziprasidone (Geodon), Amisulpride (Solian), Paliperidone (Invega), Aripiprazole (Abilify), Bifeprunox; norclozapine, in free or pharmaceutically acceptable salt form, to a patient in need thereof.

In a particular embodiment, the Compounds of the Invention are particularly useful for the treatment or prophylaxis of schizophrenia.

Compounds of the Invention, e.g., a Compound of Formula I-A or I-B, e.g., any of 1.1-1.84, or a Compound of Formula II-A or II-B, e.g., any of 2.1-2.13, in free or pharmaceutically acceptable salt form, are particularly useful for the treatment of Parkinson's disease, schizophrenia, narcolepsy, glaucoma and female sexual dysfunction.

In still another aspect, the invention provides a method of lengthening or enhancing growth of the eyelashes by administering an effective amount of a prostaglandin analogue, e.g., bimatoprost, concomitantly, simultaneously or sequentially with an effective amount of a PDE1 inhibitor of the Invention, e.g., a Compound of Formula I-A or I-B, e.g., any of 1.1-1.84, or a Compound of Formula II-A or II-B, e.g., any of 2.1-2.13, in free or pharmaceutically acceptable salt form, to the eye of a patient in need thereof.

In yet another aspect, the invention provides a method for the treatment or prophylaxis of traumatic brain injury comprising administering a therapeutically effective amount of a Compound of Formula I-A or I-B, e.g., any of 1.1-1.84, or a Compound of Formula II-A or II-B, e.g., any of 2.1-2.13, in free or pharmaceutically acceptable salt form, to a patient in need thereof Traumatic brain injury (TBI) encompasses primary injury as well as secondary injury, including both focal and diffuse brain injuries. Secondary injuries are multiple, parallel, interacting and interdependent cascades of biological reactions arising from discrete subcellular processes (e.g., toxicity due to reactive oxygen species, overstimulation of glutamate receptors, excessive influx of calcium and inflammatory upregulation) which are caused or exacerbated by the inflammatory response and progress after the initial (primary) injury. Abnormal calcium homeostasis is believed to be a critical component of the progression of secondary injury in both grey and white matter. For a review of TBI, see Park et al., CMAJ (2008) 178(9):1163-1170, the contents of which are incorporated herein in their entirety. Studies have shown that the cAMP-PICA signaling cascade is downregulated after TBI and treatment of PDE IV inhibitors such as rolipram to raise or restore cAMP level improves histopathological outcome and decreases inflammation after TBI. As Compounds of the present invention is a PDE1 inhibitor, it is believed that these compounds are also useful for the treatment of TBI, e.g., by restoring cAMP level and/or calcium homeostasis after traumatic brain injury.

The present invention also provides (i) a Compound of the Invention, e.g., Formula I or any of 1.1-1.84, or a Compound of Formula II-A or II-B, e.g., any of 2.1-2.13, in free or pharmaceutically acceptable salt form, for use as a pharmaceutical, for example for use in any method or in the treatment of any disease or condition as hereinbefore set forth, (ii) the use of a Compound of the Invention, e.g., Formula I or any of 1.1-1.84, or a Compound of Formula II-A or II-B, e.g., any of 2.1-2.13, in free or pharmaceutically acceptable salt form, in the manufacture of a medicament for treating any disease or condition as hereinbefore set forth, (iii) a pharmaceutical composition comprising a Compound of the Invention, e.g., Formula I or any of 1.1-1.84, or a Compound of Formula II-A or II-B, e.g., any of 2.1-2.13, in free or pharmaceutically acceptable salt form, in combination or association with a pharmaceutically acceptable diluent or carrier, and (iv) a pharmaceutical composition comprising a Compound of the Invention, e.g., Formula I or any of 1.1-1.84, or a Compound of Formula II-A or II-B, e.g., any of 2.1Error! Reference source not found.-2.13, in free or pharmaceutically acceptable salt form, in combination or association with a pharmaceutically acceptable diluent or carrier for use in the treatment of any disease or condition as hereinbefore set forth.

Therefore, the invention provides use of a Compound of the Invention, e.g., Formula I or any of 1.1-1.84, or a Compound of Formula II-A or II-B, e.g., any of 2.1-2.13, in free or pharmaceutically acceptable salt or prodrug form, or a Compound of the Invention in a pharmaceutical composition form, for the manufacture of a medicament for the treatment or prophylactic treatment of the following diseases: Parkinson's disease, restless leg, tremors, dyskinesias, Huntington's disease, Alzheimer's disease, and drug-induced movement disorders; depression, attention deficit disorder, attention deficit hyperactivity disorder, bipolar illness, anxiety, sleep disorder, narcolepsy, cognitive impairment, dementia, Tourette's syndrome, autism, fragile X syndrome, psychostimulant withdrawal, and/or drug addiction; cerebrovascular disease, stroke, congestive heart disease, hypertension, pulmonary hypertension, and/or sexual dysfunction; asthma, chronic obstructive pulmonary disease, and/or allergic rhinitis, as well as autoimmune and inflammatory diseases; and/or female sexual dysfunction, exercise amenorrhoea, anovulation, menopause, menopausal symptoms, hypothyroidism, pre-menstrual syndrome, premature labor, infertility, irregular menstrual cycles, abnormal uterine bleeding, osteoporosis, multiple sclerosis, prostate enlargement, prostate cancer, hypothyroidism, estrogen-induced endometrial hyperplasia or carcinoma; and/or any disease or condition characterized by low levels of cAMP and/or cGMP (or inhibition of cAMP and/or cGMP signaling pathways) in cells expressing PDE1, and/or by reduced dopamine D1 receptor signaling activity; and/or any disease or condition that may be ameliorated by the enhancement of progesterone signaling;

The invention also provides use of a Compound of the Invention, e.g., a Compound of Formula I-A or I-B, e.g., any of 1.1-1.84, or a Compound of Formula II-A or II-B, e.g., any of 2.1-2.13, in free or pharmaceutically acceptable salt form, for the manufacture of a medicament for the treatment or prophylactic treatment of:
a) glaucoma or elevated intraocular pressure,
b) psychosis, for example, any conditions characterized by psychotic symptoms such as hallucinations, paranoid or bizarre delusions, or disorganized speech and thinking, e.g., schizophrenia, schizoaffective disorder, schizophreniform disorder, psychotic disorder, delusional disorder, and mania, such as in acute manic episodes and bipolar disorder,
c) traumatic brain injury.

The words "treatment" and "treating" are to be understood accordingly as embracing prophylaxis and treatment or amelioration of symptoms of disease as well as treatment of the cause of the disease.

For methods of treatment, the word "effective amount" is intended to encompass a therapeutically effective amount to treat a specific disease or disorder.

The term "pulmonary hypertension" is intended to encompass pulmonary arterial hypertension.

The term "patient" include human or non-human (i.e., animal) patient. In particular embodiment, the invention encompasses both human and nonhuman. In another embodiment, the invention encompasses nonhuman. In other embodiment, the term encompasses human.

The term "comprising" as used in this disclosure is intended to be open-ended and does not exclude additional, unrecited elements or method steps.

Compounds of the Invention are in particular useful for the treatment of Parkinson's disease, narcolepsy and female sexual dysfunction.

Compounds of the Invention, e.g., Formula I-A or I-B or any of 1.1-1.84, or II-A or II-B, any of 2.1-2.13, in free or pharmaceutically acceptable salt form may be used as a sole therapeutic agent, but may also be used in combination or for co-administration with other active agents. For example, as Compounds of the Invention potentiate the activity of D1 agonists, such as dopamine, they may be simultaneously, sequentially, or contemporaneously administered with conventional dopaminergic medications, such as levodopa and levodopa adjuncts (carbidopa, COMT inhibitors, MAO-B inhibitors), dopamine agonists, and anticholinergics, e.g., in the treatment of a patient having Parkinson's disease. In addition, the novel PDE 1 inhibitors, e.g., as described herein, may also be administered in combination with estrogen/estradiol/estriol and/or progesterone/progestins to enhance the effectiveness of hormone replacement therapy or treatment of estrogen-induced endometrial hyperplasia or carcinoma.

Dosages employed in practicing the present invention will of course vary depending, e.g. on the particular disease or condition to be treated, the particular Compound of the Invention used, the mode of administration, and the therapy desired. Compounds of the Invention may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a Compound of the Invention, together with a pharmaceutically acceptable diluent or carrier therefor.

Pharmaceutical compositions comprising Compounds of the Invention may be prepared using conventional diluents or excipients and techniques known in the galenic art. Thus oral dosage forms may include tablets, capsules, solutions, suspensions and the like.

EXAMPLES

The synthetic methods for various Compounds of the Present Invention are illustrated below. Other compounds of the Invention and their salts may be made using the methods as similarly described below and/or by methods similar to those generally described in the detailed description and by methods known in the chemical art.

Example 1

(6aR,9aS)-5,6a,7,8,9,9a-hexahydro-5-methyl-2-((4-Pyridin-2yl)-benzyl)-cyclopent[4,5]imidazo[1,2-a]pyrrolo[4,3-e]pyrimidin-4(2H)-one

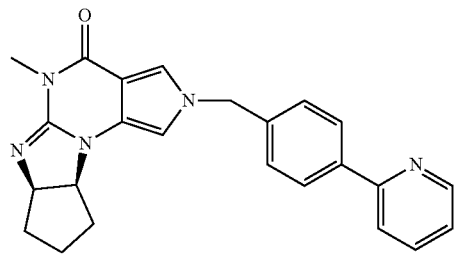 [SMILES: CN1C(=O)c2cn(Cc3ccc(-c4ccccn4)cc3)cc2N2C1=N[C@@H]1CCC[C@@H]12]

1) 2-((1R,2R)-2-hydroxycyclopentylamino)-3-methylpyrimidin-4(3H)-one

3-Methyluracil (12.6 mg, 0.1 mmol) was dissolved in 0.5 mL of DMF, and then BOP (71 mg, 0.16 mmol) was added. The mixture was stirred at room temperature for two minutes, then (1R,2R)-(−)-2-hydroxycyclopentylamine hydrochloride salt (22 mg, 0.16 mmol) was added, followed by DBU (51 uL, 3.4 mmol). The mixture was stirred at room temperature overnight. The reaction mixture was purified by a semi-preparative HPLC to give pure product (16 mg, yield 76%). MS (ESI) m/z 210.1 [M+H]+.

2) (3aS,8aR)-7-Methyl-1,2,3,3a,7,8a-hexahydro-3b,7,8-triaza-cyclopenta[a]inden-6-one To a solution of 2-((1R,2R)-2-hydroxycyclopentylamino)-3-methylpyrimidin-4(3H)-one (130 mg, 0.62 mmol) in anhydrous THF (2 mL) is added triphenylphosphine (163 mg, 0.62 mmol). Five minutes later, diethyl azodicarboxylate (DEAD, 0.45 mL, 0.93 mmol) in toluene is added dropwise. The mixture is stirred at room temperature for 2 hours. Solvent is removed under vacuum, the residue is treated with 0.02 N HCl (40 mL). The precipitate is filtered off, and the filtrate is washed with CH2Cl2. The aqueous phase is evaporated to dryness under high vacuum to give product as solids (108 mg, yield 92%), which is used for the next reaction without further purification. MS (ESI) m/z 192.1 [M+H]+.

3) (6aR,9aS)-5,6a,7,8,9,9a-hexahydro-5-methyl-cyclopent[4,5]imidazo[1,2-a]pyrrolo[4,3-e]pyrimidin-4(2H)-one Sodium hydride (95%, 112 mg, 4.44 mmol) is suspended in 3 mL of anhydrous THF, and then a mixture of (3aS,8aR)-7-Methyl-1,2,3,3a,7,8a-hexahydro-3b,7,8-triaza-cyclopenta[a]inden-6-one (283 mg, 1.48 mmol) and p-toluenesulfonylmethyl isocyanide (97%, 347 mg, 1.77 mmol) in 5 mL of anhydrous THF is added dropwise. The mixture is stirred at room temperature for an hour, and then quenched with water. The mixture is extracted with $CH_2Cl_2$ (5×10 mL). The combined organic phase is washed with brine, and then dried with anhydrous $Na_2SO_4$. After filtration, the filtrate is evaporated to dryness under reduced pressure to give crude product (320 mg, yield 94%) as brown solids, which is used for the next reaction without further purification. MS (ESI) m/z 231.1 $[M+H]^+$.

4) (6aR,9aS)-5,6a,7,8,9,9a-hexahydro-5-methyl-2-((4-Pyridin-2yl)-benzyl)-cyclopent[4,5]imidazo[1,2-a]pyrrolo[4,3-e]pyrimidin-4(2H)-one A suspension of (6aR,9aS)-5,6a,7,8,9,9a-hexahydro-5-methyl-cyclopent[4,5]imidazo[1,2-a]pyrrolo[4,3-e]pyrimidin-4(2H)-one (140 mg, 0.61 mmol), 2-(4-(chloromethyl)phenyl)pyridine (0.12 g, 0.61 mmol) and cesium carbonate (400 mg, 1.22 mmol) in anhydrous DMF is stirred at room temperature overnight. The mixture is filtered through a 0.2 µL microfilter. The filtrate is purified by a semi-preparative HPLC to give 41 mg of pure product as off white solids. MS (ESI) m/z 398.2 $[M+H]^+$.

Example 2

(6aR,9aS)-5,6a,7,8,9,9a-hexahydro-5-methyl-2-(4-(6-fluoropyridin-2-yl)benzyl)-cyclopent[4,5]imidazo[1,2-a]pyrrolo[4,3-e]pyrimidin-4(2H)-one

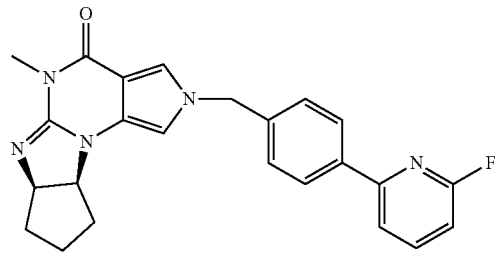 [SMILES: CN1C(=O)c2cn(Cc3ccc(-c4cccc(F)n4)cc3)cc2N2C1=N[C@@H]1CCC[C@@H]12]

The synthetic procedure of this compound is analogous to EXAMPLE 1 wherein 2-(4-(chloromethyl)phenyl)-6-fluoropyridine is used in step 4 instead of 2-(4-(chloromethyl)phenyl)pyridine. MS (ESI) m/z 416.2 $[M+H]^+$.

Example 3

(6aR,9aS)-5,6a,7,8,9,9a-hexahydro-1,5-dimethyl-2-(4-(6-fluoropyridin-2-yl)benzyl)-cyclopent[4,5]imidazo[1,2-a]pyrrolo[4,3-e]pyrimidin-4(2H)-one

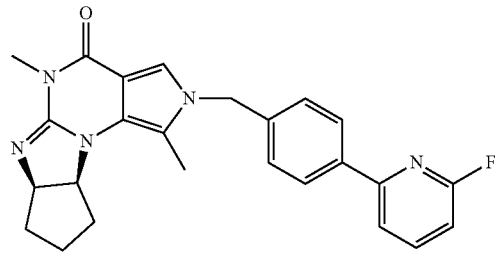 [SMILES: Cc1c2c(cn1Cc1ccc(-c3cccc(F)n3)cc1)C(=O)N(C)C1=N[C@@H]3CCC[C@@H]3N12]

The synthetic procedure of this compound is analogous to EXAMPLE 1 wherein 1-(1-isocyanoethylsulfonyl)-4-methylbenzene is used in step 3 instead of p-toluenesulfonylmethyl isocyanide, and 2-(4-(chloromethyl)phenyl)-6-fluoropyridine is used in step 4 instead of 2-(4-(chloromethyl)phenyl)pyridine. MS (ESI) m/z 416.2 $[M+H]^+$.

Example 4

(6aR,9aS)-5,6a,7,8,9,9a-hexahydro-1-chloro-5-methyl-2-(4-(6-fluoropyridin-2-yl)benzyl)-cyclopent[4,5]imidazo[1,2-a]pyrrolo[4,3-e]pyrimidin-4(2H)-one

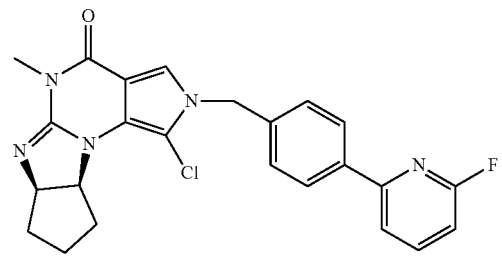 [SMILES: CN1C(=O)c2cn(Cc3ccc(-c4cccc(F)n4)cc3)c(Cl)c2N2C1=N[C@@H]1CCC[C@@H]12]

(6aR,9aS)-5,6a,7,8,9,9a-hexahydro-5-methyl-2-(4-(6-fluoropyridin-2-yl)benzyl)-cyclopent[4,5]imidazo[1,2-a]pyrrolo[4,3-e]pyrimidin-4(2H)-one (38 mg, 0.082 mmol) is dissolved in a mixture of $CCl_4$ and DMF (8/1, v/v). The solution is cooled to 0° C., and then a solution of N-chlorosuccinimide (10.9 mg, 0.082 mmol) in $CCl_4$ and DMF (8/1, v/v) is added dropwise. The reaction mixture is stirred at room temperature for half an hour. Solvents are removed under vacuum, and the residue is purified by a semi-preparative HPLC to give pure product as off white solids (16.5 mg, yield 45%). MS (ESI) m/z 450.1 $[M+H]^+$.

Example 5

(6aR,9aS)-5,6a,7,8,9,9a-hexahydro-5-methyl-1-(phenylamino)-2-(4-(6-fluoropyridin-2-yl)benzyl)-cyclopent[4,5]imidazo[1,2-a]pyrrolo[4,3-e]pyrimidin-4(2H)-one

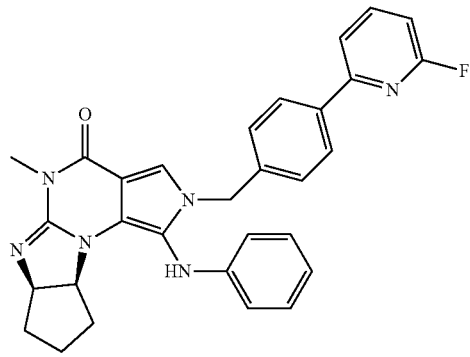 [SMILES: CN1C(=O)c2cn(Cc3ccc(-c4cccc(F)n4)cc3)c(Nc3ccccc3)c2N2C1=N[C@@H]1CCC[C@@H]12]

Crude (6aR,9aS)-5,6a,7,8,9,9a-hexahydro-1-chloro-5-methyl-2-(4-(6-fluoropyridin-2-yl)benzyl)-cyclopent[4,5]imidazo[1,2-a]pyrrolo[4,3-e]pyrimidin-4(2H)-one (approx. 0.03 mmol) is dissolved in anhydrous $CH_2Cl_2$, and then trichloroacetic acid (5.2 mg, 0.03 mmol) is added, followed by aniline (5.8 uL, 0.06 mmol). The reaction mixture is heated in a Biotage microwave instrument at 100° C. for 2 hours. The mixture is purified by a semi-preparative HPLC to give 2.2 mg of product as solids. MS (ESI) m/z 507.2 [M+H]+.

Example 6

(6aR,9aS)-5,6a,7,8,9,9a-hexahydro-5-methyl-2-(4-methoxy-benzyl)-cyclopent[4,5]imidazo[1,2-a]pyrrolo[4,3-e]pyrimidin-4(2H)-one

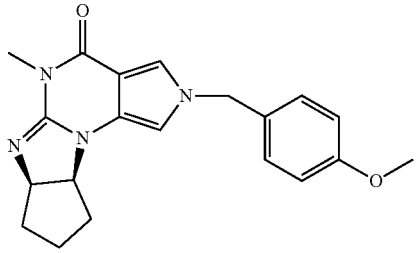

The synthetic procedure of this compound is analogous to EXAMPLE 1 wherein 1-(chloromethyl)-4-methoxybenzene is used in step 4 instead of 2-(4-(chloromethyl)phenyl)pyridine. MS (ESI) m/z 351.2 [M+H]+.

Example 7

(6aR,9aS)-5,6a,7,8,9,9a-hexahydro-3-chloro-5-methyl-2-(4-methoxy-benzyl)-cyclopent[4,5]imidazo[1,2-a]pyrrolo[4,3-e]pyrimidin-4(2H)-one

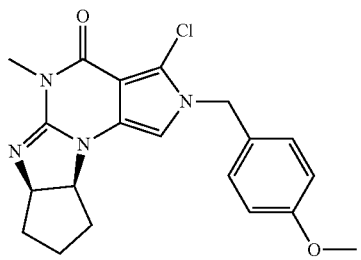

1.0M LiHMDS in THF (4.2 mL, 4.2 mmol) is added dropwise to a solution of (6aR,9aS)-5,6a,7,8,9,9a-hexahydro-5-methyl-2-(4-methoxy-benzyl)-cyclopent[4,5]imidazo[1,2-a]pyrrolo[4,3-e]pyrimidin-4(2H)-one (500 mg, 1.4 mmol) and hexachloroethane (1.69 g, 7.13 mmol) at room temperature under argon. After 30 min, the mixture is quenched with saturated ammonium chloride aqueous solution at 0° C., and then basified with saturated sodium bicarbonate aqueous solution, followed by extractions with methylene chloride. The collected organic phase is washed with brine, dried over anhydrous sodium sulfate, and then evaporated to dryness under reduced pressure. The obtained crude product is purified by silica gel flash chromatography to give 165 mg of pure product as off white solid (yield: 30%). MS (ESI) m/z 385.2 [M+H]+.

Example 8

(6aR,9aS)-5,6a,7,8,9,9a-hexahydro-3-chloro-5-methyl-2-((4-Pyridin-2yl)-benzyl)-cyclopent[4,5]imidazo[1,2-a]pyrrolo[4,3-e]pyrimidin-4(2H)-one

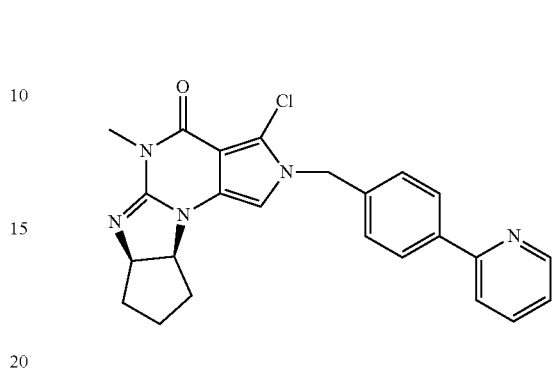

To a solution of (6aR,9aS)-5,6a,7,8,9,9a-hexahydro-3-chloro-5-methyl-2-(4-methoxy-benzyl)-cyclopent[4,5]imidazo[1,2-a]pyrrolo[4,3-e]pyrimidin-4(2H)-one (95 mg, 0.25 mmol) in CH2Cl2 is slowly added TFA and trifluoromethanesulfonic acid (TFMSA). The mixture is stirred at room temperature overnight. Solvents and TFA are removed under reduced pressure. The residue is neutralized and dissolved in DMF, and then purified by a semi-preparative HPLC to give 77 mg of (6aR,9aS)-5,6a,7,8,9,9a-hexahydro-3-chloro-5-methyl-cyclopent[4,5]imidazo[1,2-a]pyrrolo[4,3-e]pyrimidin-4(2H)-one. A suspension of (6aR,9aS)-5,6a,7,8,9,9a-hexahydro-3-chloro-5-methyl-cyclopent[4,5]imidazo[1,2-a]pyrrolo[4,3-e]pyrimidin-4(2H)-one (79 mg, 0.3 mmol), 2-(4-(chloromethyl)phenyl)pyridine (61 mg, 0.3 mmol) and cesium carbonate (192 mg, 0.6 mmol) in anhydrous DMF is stirred at room temperature for 4 h. The mixture is filtered through a 0.2 μL microfilter. The filtrate is purified by a semi-preparative HPLC to give pure product. MS (ESI) m/z 432.2 [M+H]+.

Example 9

(6aR,9aS)-5,6a,7,8,9,9a-hexahydro-5-methyl-3-(phenylamino)-2-((4-Pyridin-2yl)-benzyl)-cyclopent[4,5]imidazo[1,2-a]pyrrolo[4,3-e]pyrimidin-4(2H)-one

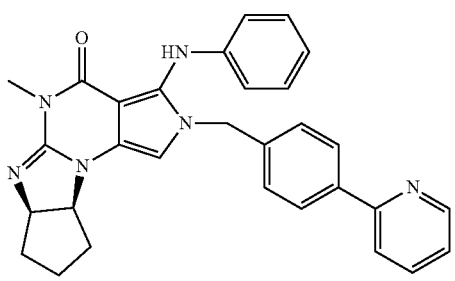 [SMILES: CN1C(=O)c2c(cn(Cc3ccc(-c4ccccn4)cc3)c2Nc2ccccc2)N2C1=N[C@@H]1CCC[C@@H]12]

(6aR,9aS)-5,6a,7,8,9,9a-hexahydro-3-chloro-5-methyl-2-((4-Pyridin-2yl)-benzyl)-cyclopent[4,5]imidazo[1,2-a]pyrrolo[4,3-e]pyrimidin-4(2H)-one (5.6 mg, 0.013 mmol) is placed in a Biotage microwave tube, and then aniline (0.2 mL) is added. The mixture is heated at 150° C. for an hour. The mixture is purified by a semi-preparative HPLC to give product. MS (ESI) m/z 489.3 [M+H]+.

Example 10

(6aR,9aS)-5,6a,7,8,9,9a-hexahydro-5-methyl-3-(phenylamino)-2-(4-methoxy-benzyl)-cyclopent[4,5]imidazo[1,2-a]pyrrolo[4,3-e]pyrimidin-4(2H)-one

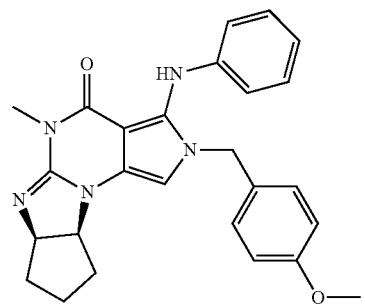

The synthetic procedure of this compound is analogous to EXAMPLE 9 wherein (6aR,9aS)-5,6a,7,8,9,9a-hexahydro-3-chloro-5-methyl-2-(4-methoxy-benzyl)-cyclopent[4,5]imidazo[1,2-a]pyrrolo[4,3-e]pyrimidin-4(2H)-one is used instead of (6aR,9aS)-5,6a,7,8,9,9a-hexahydro-3-chloro-5-methyl-2-((4-Pyridin-2yl)-benzyl)-cyclopent[4,5]imidazo[1,2-a]pyrrolo[4,3-e]pyrimidin-4(2H)-one. MS (ESI) m/z 442.2 [M+H]+.

Example 11

(6aR,9aS)-5,6a,7,8,9,9a-hexahydro-5-methyl-3-(phenylamino)-2-(4-(1H-1,2,4-triazol-1-yl)-benzyl)-cyclopent[4,5]imidazo[1,2-a]pyrrolo[4,3-e]pyrimidin-4(2H)-one

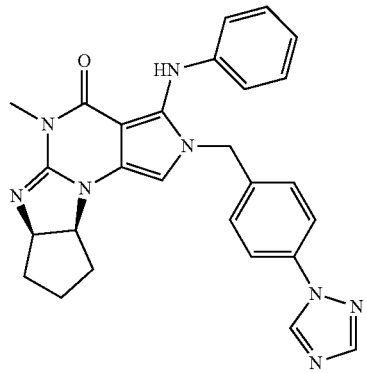 [SMILES: CN1C(=O)c2c(cn(Cc3ccc(-n4cncn4)cc3)c2Nc2ccccc2)N2C1=N[C@@H]1CCC[C@@H]12]

The synthetic procedure of this compound is analogous to EXAMPLE 9 wherein (6aR,9aS)-5,6a,7,8,9,9a-hexahydro-3-chloro-5-methyl-2-(4-(1H-1,2,4-triazol-1-yl)-benzyl)-cyclopent[4,5]imidazo[1,2-a]pyrrolo[4,3-e]pyrimidin-4(2H)-one is used instead of (6aR,9aS)-5,6a,7,8,9,9a-hexahydro-3-chloro-5-methyl-2-((4-Pyridin-2yl)-benzyl)-cyclopent[4,5]imidazo[1,2-a]pyrrolo[4,3-e]pyrimidin-4(2H)-one. MS (ESI) m/z 479.3 [M+H]+.

Example 12

(6aR,9aS)-5,6a,7,8,9,9a-hexahydro-5-methyl-1-(phenylamino)-2-(4-(pyridin-2-yl)benzyl)-cyclopent[4,5]imidazo[1,2-a]pyrrolo[4,3-e]pyrimidin-4(2H)-one

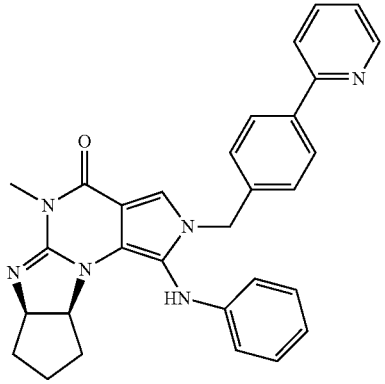 [SMILES: CN1C(=O)c2cn(Cc3ccc(-c4ccccn4)cc3)c(Nc3ccccc3)c2N2C1=N[C@@H]1CCC[C@@H]12]

The synthetic procedure of this compound is analogous to EXAMPLE 9 wherein (6aR,9aS)-5,6a,7,8,9,9a-hexahydro-5-methyl-1-chloro-2-(4-(pyridin-2-yl)benzyl)-cyclopent[4,5]imidazo[1,2-a]pyrrolo[4,3-e]pyrimidin-4(2H)-one is used instead of (6aR,9aS)-5,6a,7,8,9,9a-hexahydro-3-chloro-5-methyl-2-((4-Pyridin-2yl)-benzyl)-cyclopent[4,5]imidazo[1,2-a]pyrrolo[4,3-e]pyrimidin-4(2H)-one. MS (ESI) m/z 489.2 [M+H]+.

Example 13

(6aR,9aS)-5,6a,7,8,9,9a-hexahydro-5-methyl-3-(phenylamino)-2-(4-(pyridin-4-yl)benzyl)-cyclopent[4,5]imidazo[1,2-a]pyrrolo[4,3-e]pyrimidin-4(2H)-one

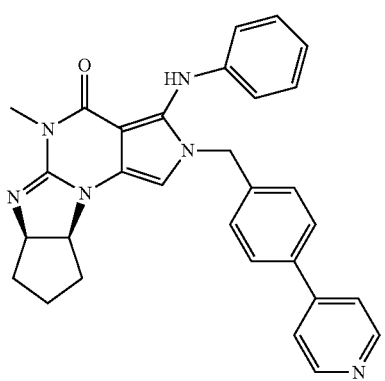 [SMILES: CN1C(=O)c2c(cn(Cc3ccc(-c4ccncc4)cc3)c2Nc2ccccc2)N2C1=N[C@@H]1CCC[C@@H]12]

The synthetic procedure of this compound is analogous to EXAMPLE 9 wherein (6aR,9aS)-5,6a,7,8,9,9a-hexahydro-5-methyl-3-chloro-2-(4-(pyridin-4-yl)benzyl)-cyclopent[4,5]imidazo[1,2-a]pyrrolo[4,3-e]pyrimidin-4(2H)-one is used instead of (6aR,9aS)-5,6a,7,8,9,9a-hexahydro-3-chloro-5- methyl-2-((4-Pyridin-2yl)-benzyl)-cyclopent[4,5]imidazo[1,2-a]pyrrolo[4,3-e]pyrimidin-4(2H)-one. MS (ESI) m/z 489.3 [M+H]⁺.

Example 14

(6aR,9aS)-5,6a,7,8,9,9a-hexahydro-5-methyl-3-(phenylamino)-2-(4-(1H-imidazol-1-yl)benzyl)-cyclopent[4,5]imidazo[1,2-a]pyrrolo[4,3-e]pyrimidin-4(2H)-one

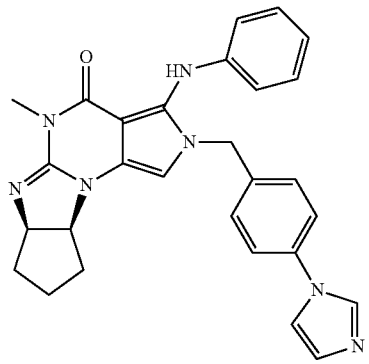 [SMILES: CN1C(=O)c2c(cn(Cc3ccc(-n4ccnc4)cc3)c2Nc2ccccc2)N2C1=N[C@@H]1CCC[C@@H]12]

The synthetic procedure of this compound is analogous to EXAMPLE 9 wherein (6aR,9aS)-5,6a,7,8,9,9a-hexahydro-5-methyl-3-chloro-2-(4-(1H-imidazol-1-yl)benzyl)-cyclopent[4,5]imidazo[1,2-a]pyrrolo[4,3-e]pyrimidin-4(2H)-one is used instead of (6aR,9aS)-5,6a,7,8,9,9a-hexahydro-3-chloro-5-methyl-2-((4-Pyridin-2yl)-benzyl)-cyclopent[4,5]imidazo[1,2-a]pyrrolo[4,3-e]pyrimidin-4(2H)-one. MS (ESI) m/z 478.2 [M+H]⁺.

Example 15

(6aR,9aS)-5,6a,7,8,9,9a-hexahydro-5-methyl-3-(phenylthio)-2-(4-(pyridin-2-yl)benzyl)-cyclopent[4,5]imidazo[1,2-a]pyrrolo[4,3-e]pyrimidin-4(2H)-one

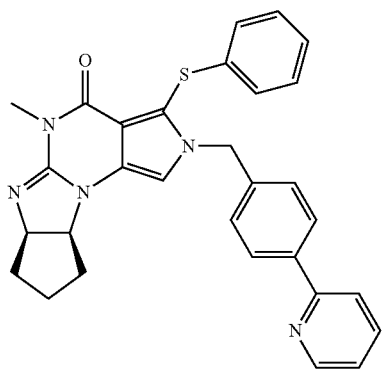 [SMILES: CN1C(=O)c2c(cn(Cc3ccc(-c4ccccn4)cc3)c2Sc2ccccc2)N2C1=N[C@@H]1CCC[C@@H]12]

(6aR,9aS)-5,6a,7,8,9,9a-hexahydro-5-methyl-2-((4-Pyridin-2yl)-benzyl)-cyclopent[4,5]imidazo[1,2-a]pyrrolo[4,3-e]pyrimidin-4(2H)-one (20 mg, 0.05 mmol) and phenyl disulfide (22 mg, 0.10 mmol) are dissolved in 400 μL of anhydrous THF, and then 1.0 M LiHMDS in THF (150 μL, 0.15 mmol) is added dropwise. The mixture is stirred at room temperature for 10 min, and then quenched with ammonium chloride aqueous solution. The mixture is diluted with DMF, and then purified by a semi-preparative HPLC to give pure product as pale yellow solid. MS (ESI) m/z 506.2 [M+H]⁺.

Example 16

Measurement of PDE1B Inhibition In Vitro Using IMAP Phosphodiesterase Assay Kit

Phosphodiesterase 1B (PDE1B) is a calcium/calmodulin dependent phosphodiesterase enzyme that converts cyclic guanosine monophosphate (cGMP) to 5'-guanosine monophosphate (5'-GMP). PDE1B can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein—IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization (Δmp). Inhibition of phosphodiesterase, therefore, is detected as a decrease in Δmp.

Enzyme Assay

Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: 3',5'-cyclic-nucleotide-specific bovine brain phosphodiesterase (Sigma, St. Louis, Mo.) is reconstituted with 50% glycerol to 2.5 U/ml. One unit of enzyme will hydrolyze 1.0 μmole of 3',5'-cAMP to 5'-AMP per min at pH 7.5 at 30° C. One part enzyme is added to 1999 parts reaction buffer (30 μM CaCl₂, 10 U/ml of calmodulin (Sigma P2277), 10 mM Tris-HCl pH 7.2, 10 mM MgCl₂, 0.1% BSA, 0.05% NaN₃) to yield a final concentration of 1.25 mU/ml. 99 μl of diluted enzyme solution is added into each well in a flat bottom 96-well polystyrene plate to which 1 μl of test compound dissolved in 100% DMSO is added. The compounds are mixed and pre-incubated with the enzyme for 10 min at room temperature.

The FL-GMP conversion reaction is initiated by combining 4 parts enzyme and inhibitor mix with 1 part substrate solution (0.225 μM) in a 384-well microtiter plate. The reaction is incubated in dark at room temperature for 15 min. The reaction is halted by addition of 60 μl of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization (Δmp).

A decrease in GMP concentration, measured as decreased Δmp, is indicative of inhibition of PDE activity. IC₅₀ values are determined by measuring enzyme activity in the presence of 8 to 16 concentrations of compound ranging from 0.0037 nM to 80,000 nM and then plotting drug concentration versus ΔmP, which allows $IC_{50}$ values to be estimated using nonlinear regression software (XLFit; IDBS, Cambridge, Mass.).

The Compounds of the Invention may be tested in an assay as described or similarly described herein for PDE1 inhibitory activity. The exemplified compounds generally have $IC_{50}$ values of less than 100 μM, some less than 10 μM, some less than 500 nM, some less than 10 nM, some against PDE1A. the Compounds of Examples 1, 3 and 5 generally have $IC_{50}$ values of about or less than 10 μM, some less than 500 nM, some less than 10 nM, particularly against PDE1A.

Example 17

PDE1 Inhibitor Effect on Sexual Response in Female Rats

The effect of PDE1 inhibitors on Lordosis Response in female rats may be measured as described in Mani, et al., Science (2000) 287: 1053. Ovariectomized and cannulated wild-type rats are primed with 2 μg estrogen followed 24 hours later by intracerebroventricular (icy) injection of progesterone (2 μg), PDE1 inhibitors of the present invention (0.1 mg, 1.0 mg or 2.5 mg) or sesame oil vehicle (control). The rats are tested for lordosis response in the presence of male rats. Lordosis response is quantified by the lordosis quotient (LQ=number of lordosis/10 mounts×100).

What is claimed is:

1. An optionally substituted 4,5,7,8-tetrahydro-(optionally 4-oxo, 4-thioxo or 4-imino)-2H-imidazo[1,2-a]pyrrolo[3,4-e]pyrimidine or 4,5,7,8,9-pentahydro-(optionally 4-oxo, 4-thioxo or 4-imino)-2H-pyrimido[1,2-a]pyrrolo[3,4-e]pyrimidine, in free or salt form.

2. The compound according to claim 1, wherein said compound is a Compound of Formula II-A or II-B

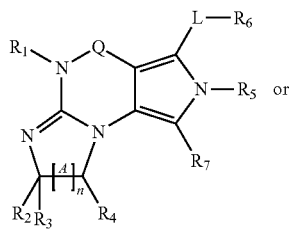

Formula II-A

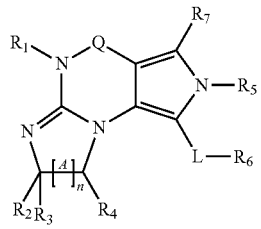

Formula II-B wherein
(i) Q is C(=O), C(=S), C(=N($R_{20}$)) or $CH_2$;
(ii) L is a single bond, —N(H)—, —$CH_2$—, —S—, —S(O)— or —S($O_2$)—;
(iii) $R_1$ is H or $C_{1-4}$ alkyl;
(iv) $R_4$ is H or $C_{1-6}$ alkyl and $R_2$ and $R_3$ are, independently, H
$C_{1-6}$alkyl optionally substituted with halo or hydroxy, aryl,
heteroaryl,
(optionally hetero)arylalkoxy,
(optionally hetero)aryl$C_{1-6}$alkyl,
$R_2$ and $R_3$ together form a 3- to 6-membered ring;
or
$R_2$ is H and $R_3$ and $R_4$ together form a di-, tri- or tetramethylene bridge;
(v) $R_5$ is
a) -D-E-F, wherein:
D is $C_{1-4}$alkylene;
E is a single bond, $C_{2-4}$alkynylene, arylene or heteroarylene;
F is
H,
aryl,
heteroaryl,
halo,
halo$C_{1-4}$alkyl,
—N($R_{16}$)($R_{17}$), or
$C_{3-7}$cycloalkyl optionally containing at least one atom selected from a group consisting of N or O;
wherein D, E and F are independently and optionally substituted with one or more halo, $C_{1-4}$alkyl, halo$C_{1-4}$alkyl, $C_{1-4}$alkoxy, hydroxy, carboxy, or an additional aryl or heteroaryl; or
b) a halo$C_{1-4}$alkyl substituted heteroarylalkyl; or
c) attached to the nitrogen on the pyrrolo portion of Formula II-A or II-B and is a moiety of Formula A

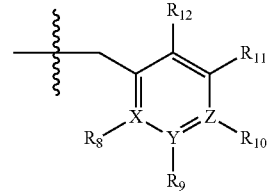

Formula A wherein X, Y and Z are, independently, N or C, and $R_8$, $R_9$, $R_{11}$ and $R_{12}$ are independently H or halogen, and $R_{10}$ is
halogen,
$C_{1-4}$alkyl,
halo$C_{1-4}$alkyl,
$C_{1-4}$alkoxy,
$C_{3-7}$cycloalkyl,
hetero$C_{3-7}$cycloalkyl,
$C_{1-4}$haloalkyl,
aryl,
heteroaryl,
arylcarbonyl,
alkylsulfonyl,
heteroarylcarbonyl, or
alkoxycarbonyl;
wherein the aryl, heteroaryl, cycloalkyl or heterocycloalkyl is independently, optionally substituted with one or more $C_{1-4}$alkyl, halogen, halo$C_{1-4}$alkyl, hydroxy, carboxy, —SH or an additional aryl or heteroaryl,
provided that when X, Y, or Z is nitrogen, $R_8$, $R_9$, or $R_{10}$, respectively, is not present;
(vi) $R_6$ is
H,
$C_{1-4}$alkyl,
$C_{3-7}$cycloalkyl,
hetero$C_{3-7}$cycloalkyl, aryl,
heteroaryl,
arylC$_{1-4}$alkyl,
when L is a single bond, —CH$_2$—, —N(H)—, —S—, —S(O)— or S(O$_2$)—,
wherein the aryl and heteroaryl are optionally substituted with one or more C$_{1-4}$alkyl, halogen, haloC$_{1-4}$alkyl, hydroxy, carboxy, or an additional aryl, heteroaryl or C$_{3-8}$cycloalkyl;
or R$_6$ is
H,
arylamino,
heteroarylamino,
N,N-diC$_{1-4}$alkylamino,
N,N-diarylamino,
N-aryl-N-(arylC$_{1-4}$alkyl)amino, or
—N(R$_{18}$)(R$_{19}$),
when L is a single bond or —CH$_2$—,
(vii) wherein the aryl and heteroaryl are optionally substituted with one or more C$_{1-4}$alkyl, halogen, haloC$_{1-4}$alkyl, hydroxy, carboxy, or an additional aryl, heteroaryl or C$_{3-8}$cycloalkyl;
(viii) R$_7$ is H, C$_{1-6}$alkyl, halogen, —N(R$_{18}$)(R$_{19}$), hydroxy or C$_{1-6}$alkoxy;
(ix) n=0 or 1;
(x) when n=1, A is —C(R$_{13}$R$_{14}$)—, wherein R$_{13}$ and R$_{14}$, are, independently, H or C$_{1-4}$alkyl, aryl, heteroaryl, (optionally hetero)arylC$_{1-4}$alkoxy, (optionally hetero)arylC$_{1-4}$alkyl or R$_{13}$ or R$_{14}$ can form a bridge with R$_2$ or R$_4$;
(xi) R$_{15}$ is C$_{1-4}$alkyl, haloC$_{1-4}$alkyl, —OH or —OC$_{1-4}$alkyl;
(xii) R$_{16}$ and R$_{17}$ are independently H or C$_{1-4}$alkyl;
(xiii) R$_{18}$ and R$_{19}$ are independently H, C$_{1-4}$alkyl, C$_{3-8}$cycloalkyl, heteroC$_{3-8}$cycloalky, aryl or heteroaryl, wherein said aryl and heteroaryl are optionally substituted with one or more halo, hydroxy, C$_{1-4}$alkyl, halo C$_{1-4}$alkyl, carboxy, or an additional aryl, heteroaryl or C$_{3-8}$cycloalkyl,
(xiv) R$_{20}$ is H, C$_{1-4}$alkyl or C$_{3-7}$cycloalkyl;
in free or salt form.

3. A Compound of Formula I-A or I-B

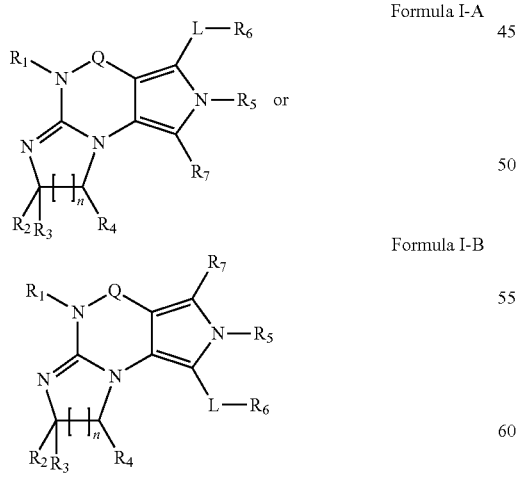

Formula I-A

Formula I-B wherein
(i) Q is C(=O), C(=S), C(=N(R$_{20}$)) or CH$_2$;
(ii) L is a single bond, —N(H)—, —CH$_2$—, —S—, —S(O)— or —S(O$_2$)—;
(iii) R$_1$ is H or C$_{1-4}$ alkyl;

(iv) R$_4$ is H or C$_{1-6}$ alkyl and R$_2$ and R$_3$ are, independently, H or C$_{1-6}$alkyl optionally substituted with halo or hydroxy, aryl, heteroaryl, (optionally hetero)arylalkoxy, or (optionally hetero)arylC$_{1-6}$alkyl;
or
R$_2$ is H and R$_3$ and R$_4$ together form a di-, tri- or tetramethylene bridge;
(v) R$_5$ is
a) -D-E-F, wherein:
D is C$_{1-4}$alkylene;
E is a single bond, C$_{2-4}$alkynylene, arylene or heteroarylene;
F is H, aryl, heteroaryl, halo, haloC$_{1-4}$alkyl, —C(O)—R$_{15}$, —N(R$_{16}$)(R$_{17}$), or C$_{3-7}$cycloalkyl optionally containing at least one atom selected from a group consisting of N or O;
wherein D, E and F are independently and optionally substituted with one or more halo, C$_{1-4}$alkyl, haloC$_{1-4}$alkyl; or
b) a haloalkyl substituted heteroarylalkyl; or
c) attached to the nitrogen on the pyrrolo portion of Formula I-A or I-B and is a moiety of Formula A

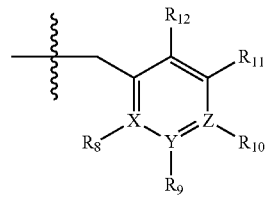

Formula A wherein X, Y and Z are, independently, N or C, and R$_8$, R$_9$, R$_{11}$ and R$_{12}$ are independently H or halogen, and R$_{10}$ is halogen, C$_{1-4}$alkyl, C$_{3-7}$cycloalkyl, C$_{1-4}$haloalkyl, aryl, heteroaryl, arylcarbonyl, alkylsulfonyl, heteroarylcarbonyl, or alkoxycarbonyl; provided that when X, Y, or Z is nitrogen, R$_8$, R$_9$, or R$_{10}$, respectively, is not present;
(vi) R$_6$ is
H,
C$_{1-4}$alkyl,
C$_{3-7}$cycloalkyl,
aryl,
heteroaryl,
arylC$_{1-4}$alkyl,
arylamino,
heteroarylamino,
N,N-diC$_{1-4}$alkylamino,
N,N-diarylamino,
N-aryl-N-(arylC$_{1-4}$alkyl)amino, or
—N(R$_{18}$)(R$_{19}$);
wherein the aryl or heteroaryl is optionally substituted with one or more halo, hydroxy or C$_{1-6}$alkoxy;
(vii) R$_7$ is H, C$_{1-6}$alkyl, halogen, or —N(R$_{18}$)(R$_{19}$);
(viii) n=0 or 1;
(ix) when n=1, A is —C(R$_{13}$R$_{14}$)—, wherein R$_{13}$ and R$_{14}$, are, independently, H or C$_{1-4}$alkyl, aryl, heteroaryl, (optionally hetero)arylC$_{1-4}$alkoxy or (optionally hetero)arylC$_{1-4}$alkyl;
(x) R$_{15}$ is C$_{1-4}$alkyl, haloC$_{1-4}$alkyl, —OH or —OC$_{1-4}$alkyl;
(xi) R$_{16}$ and R$_{17}$ are independently H or C$_{1-4}$alkyl;
(xii) R$_{18}$ and R$_{19}$ are independently H, C$_{1-4}$alky or aryl wherein said aryl is optionally substituted with one or more halo or hydroxy;

(xiii) R$_{20}$ is H, C$_{1-4}$alkyl or C$_{3-7}$cycloalkyl,
in free or salt form.
4. The compound according to claim 2, selected from any of the following:
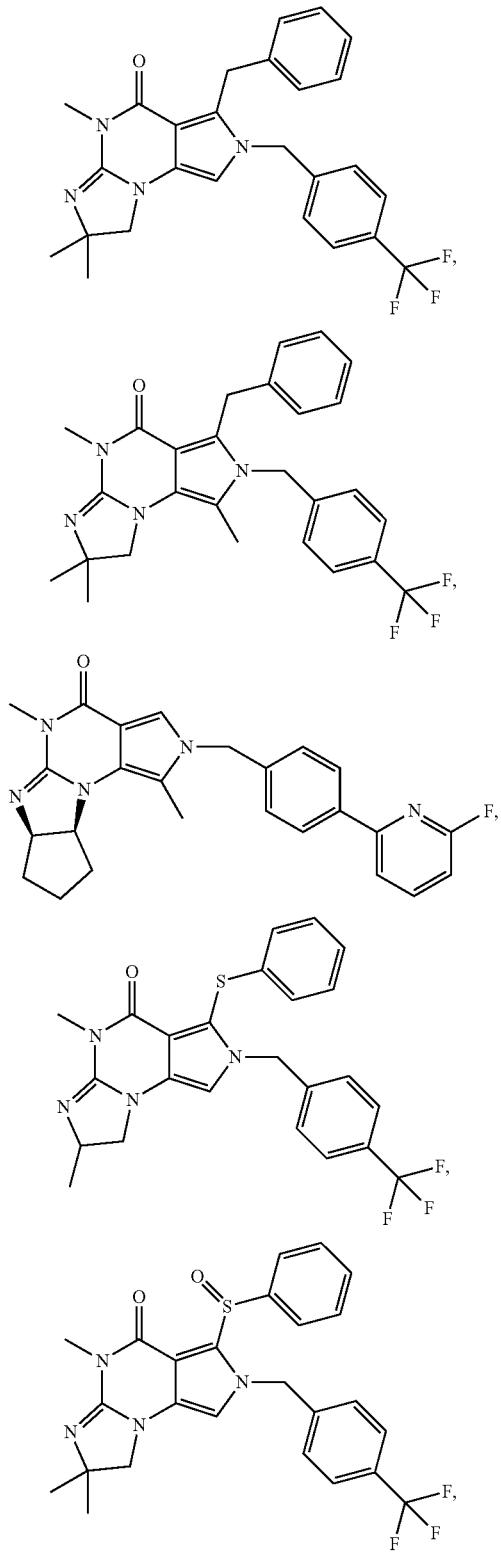
-continued
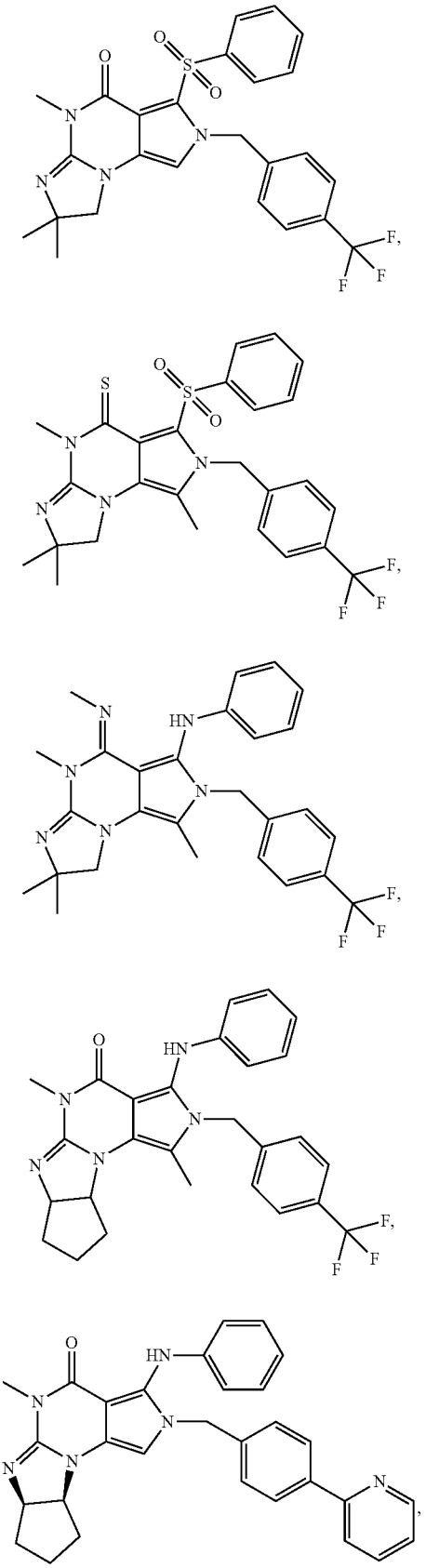

71
-continued
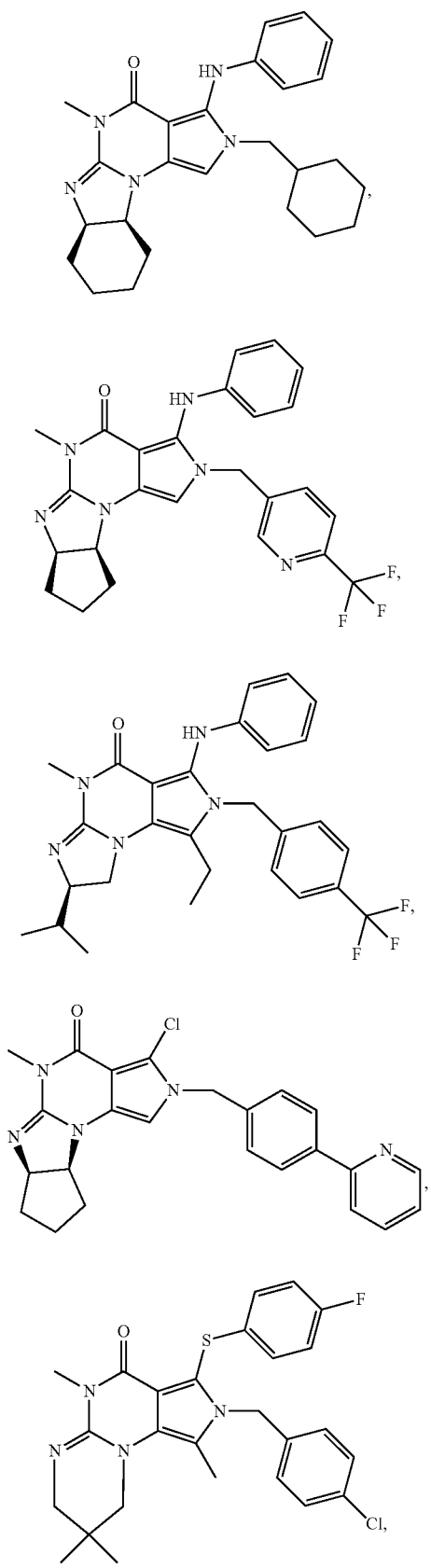
72
-continued
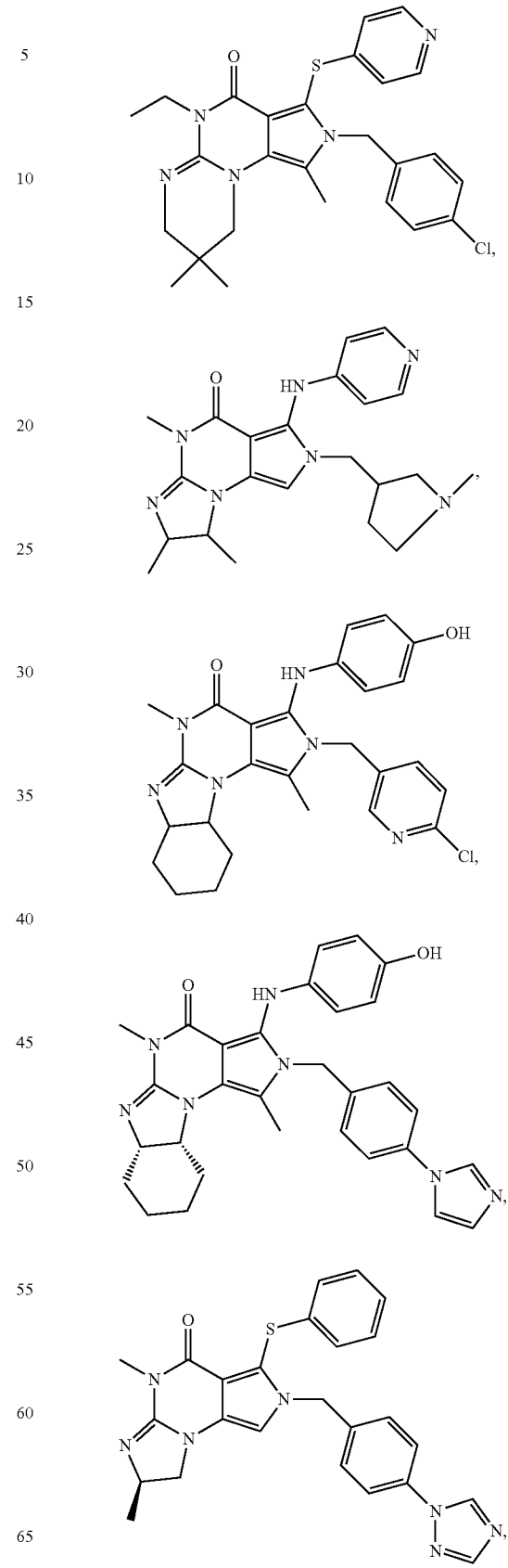

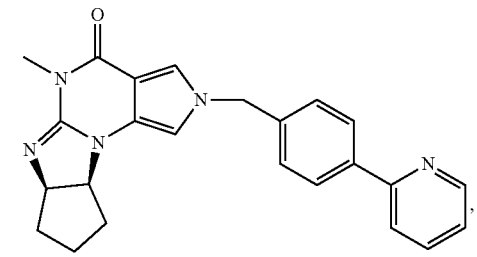
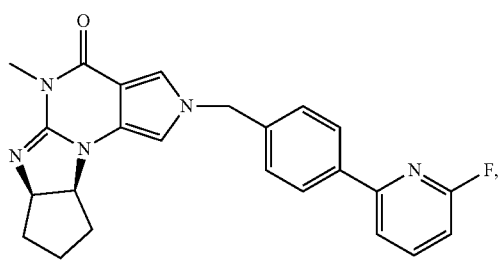
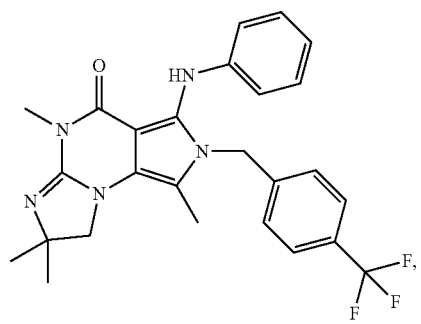
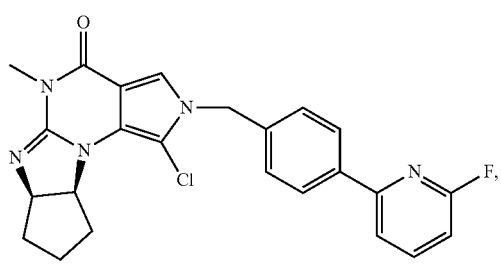
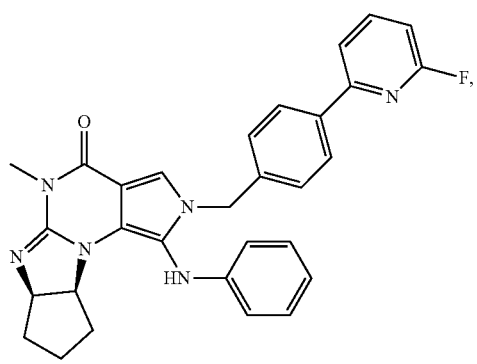
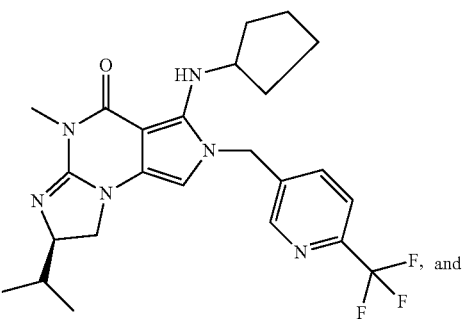
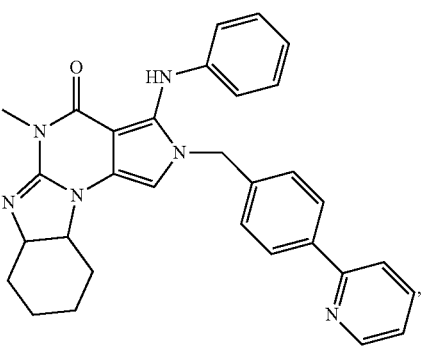
in free or salt form.
5. The compound according to claim 2, selected from any of the following:
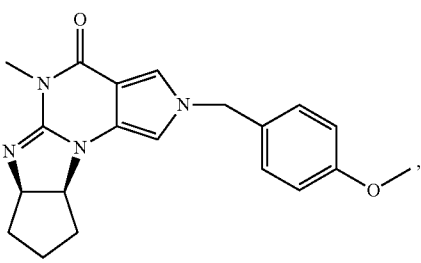
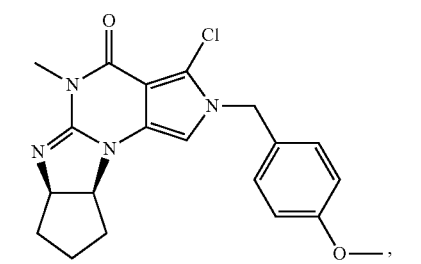
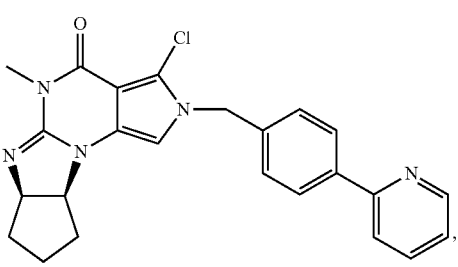

-continued

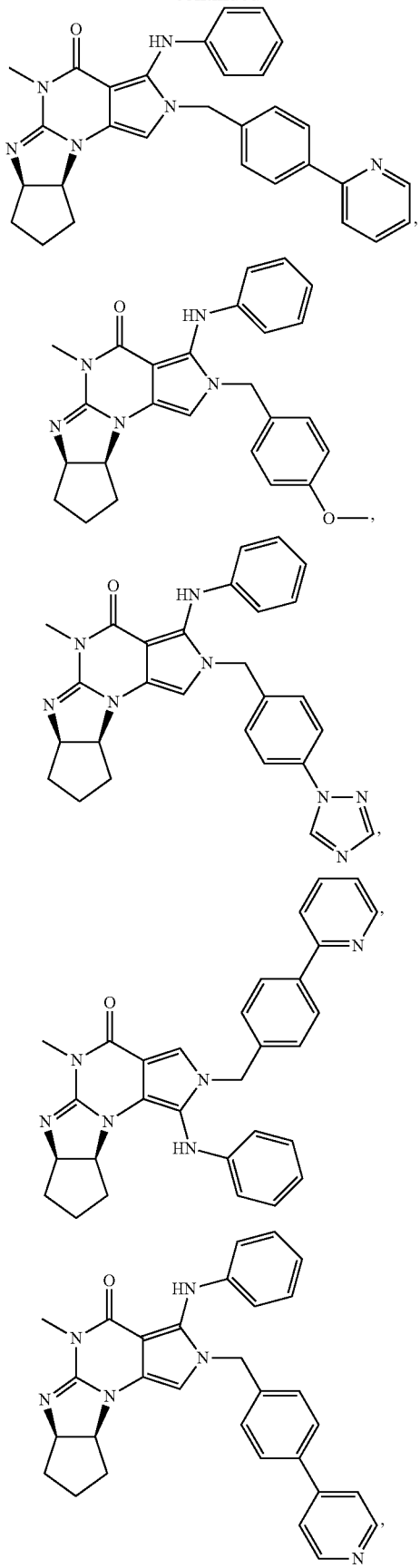

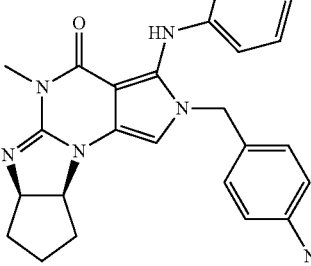

and

in free or salt form.

6. A pharmaceutical composition comprising a compound according to claim 2, in free or pharmaceutically acceptable salt form, in admixture with a pharmaceutically acceptable diluent or carrier.

7. The pharmaceutical composition according to claim 6, wherein salt and the diluents or carrier are opthalmically acceptable.

8. A method of treating any of the following conditions: Parkinson's disease, restless leg, tremors, dyskinesias, Huntington's disease, Alzheimer's disease, and drug-induced movement disorders; depression, attention deficit disorder, attention deficit hyperactivity disorder, bipolar illness, anxiety, sleep disorder, narcolepsy, cognitive impairment, dementia, Tourette's syndrome, autism, fragile X syndrome, psychostimulant withdrawal, and/or drug addiction; cerebrovascular disease, stroke, congestive heart disease, hypertension, pulmonary hypertension, and/or sexual dysfunction; asthma, chronic obstructive pulmonary disease, and/or allergic rhinitis, as well as autoimmune and inflammatory diseases; and/or female sexual dysfunction, exercise amenorrhoea, anovulation, menopause, menopausal symptoms, hypothyroidism, pre-menstrual syndrome, premature labor, infertility, irregular menstrual cycles, abnormal uterine bleeding, osteoporosis, multiple sclerosis, prostate enlargement, prostate cancer, hypothyroidism, estrogen-induced endometrial hyperplasia or carcinoma; and/or any disease or condition characterized by low levels of cAMP and/or cGMP (or inhibition of cAMP and/or cGMP signaling pathways) in cells expressing PDE1, and/or by reduced dopamine D1 receptor signaling activity; and/or any disease or condition that may be ameliorated by the enhancement of progesterone signaling; comprising administering an effective amount of a compound according to claim 2, to a patient in need of such treatment.

9. The method of claim 8, wherein the condition is Parkinson's disease.

10. The method of claim 8, wherein the condition is cognitive impairment.

11. The method of claim 8, wherein the condition is narcolepsy.

12. The method of claim 11 further comprising administering a compound or compounds selected from central nervous system stimulants, modafinil, antidepressants, and gamma hydroxybutyrate, to a patient in need thereof.

13. The method of claim 8, wherein said condition is female sexual dysfunction.

14. The method of claim 13, further comprising administering a compound or compounds selected from a group consisting of estradiol, estriol, estradiol esters, progesterone and progestins to a patient in need thereof.

15. A method for the treatment of glaucoma or elevated intraocular pressure comprising topical administration of a therapeutically effective amount of a compound according to claim 2, in free or pharmaceutically acceptable salt form, in an opthalmically compatible carrier to the eye of a patient in need thereof.

16. A method for the treatment of psychosis, schizophrenia, schizoaffective disorder, schizophreniform disorder, psychotic disorder, delusional disorder, and mania, such as in acute manic episodes and bipolar disorder, comprising administering a therapeutically effective amount of a compound according to claim 2, in free or pharmaceutically acceptable salt form, to a patient in need thereof.

17. A method for the treatment of traumatic brain injury comprising administering to a patient in need thereof, a compound according to claim 2, in free or pharmaceutically acceptable salt form.

18. A method for lengthening or enhancing growth of the eyelashes by administering an effective amount of a prostaglandin analogue concomitantly, simultaneously or sequentially with an effective amount of a compound according to claim 2, in free or salt form.

19. The compound according to claim 2, wherein
(i) Q is C(=O), C(=S), C(=N($R_{20}$)) or $CH_2$;
(ii) L is —N(H)—, —S—, —S(O)— or —S($O_2$)—;
(iii) $R_1$ is H or $C_{1-4}$ alkyl;
(iv) $R_4$ is H or $C_{1-6}$ alkyl and $R_2$ and $R_3$ are, independently,
H
$C_{1-6}$alkyl optionally substituted with halo or hydroxy,
aryl,
heteroaryl,
(optionally hetero)arylalkoxy,
(optionally hetero)aryl$C_{1-6}$alkyl, or
$R_2$ and $R_3$ together form a 3- to 6-membered ring;
or
$R_2$ is H and $R_3$ and $R_4$ together form a di-, tri- or tetramethylene bridge;
(v) $R_5$ is attached to the nitrogen on the pyrrolo portion of Formula II-A or II-B and is a moiety of Formula A

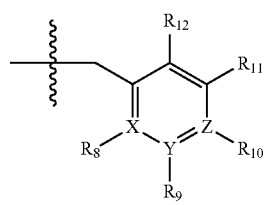

Formula A wherein X, Y and Z are, independently, N or C, and $R_8$, $R_9$, $R_{11}$ and $R_{12}$ are independently H or halogen, and $R_{10}$ is
$C_{1-4}$alkoxy,
$C_{3-7}$cycloalkyl,
hetero$C_{3-7}$cycloalkyl,
aryl,
heteroaryl,
wherein the aryl, heteroaryl, cycloalkyl or heterocloalkyl is independently, optionally substituted with one or more $C_{1-4}$alkyl, halogen, halo$C_{1-4}$alkyl, hydroxy, carboxy, —SH or an additional aryl or heteroaryl,
provided that when X, Y, or Z is nitrogen, $R_9$, $R_9$, or $R_{10}$, respectively, is not present;
(vi) $R_6$ is
H,
$C_{1-4}$alkyl,
$C_{3-7}$cycloalkyl,
hetero$C_{3-7}$cycloalkyl,
aryl,
heteroaryl,
wherein the aryl and heteroaryl are optionally substituted with one or more $C_{1-4}$alkyl, halogen, halo$C_{1-4}$alkyl, hydroxy, carboxy, or an additional aryl, heteroaryl or $C_{3-8}$cycloalkyl;
(vii) $R_7$ is H, $C_{1-6}$alkyl, halogen, —N($R_{18}$)($R_{19}$), hydroxy or $C_{1-6}$alkoxy;
(viii) n=0 or 1;
(ix) when n=1, A is —C($R_{13}R_{14}$)—, wherein $R_{13}$ and $R_{14}$, are, independently, H or $C_{1-4}$alkyl, aryl, heteroaryl, (optionally hetero)aryl$C_{1-4}$alkoxy, (optionally hetero)aryl$C_{1-4}$alkyl or $R_{13}$ or $R_{14}$ can form a bridge with $R_2$ or $R_4$;
(x) $R_{18}$ and $R_{19}$ are independently H, $C_{1-4}$alky, $C_{3-8}$cycloalky, hetero$C_{3-8}$cycloalky, aryl or heteroaryl, wherein said aryl and heteroaryl are optionally substituted with one or more halo, hydroxy, $C_{1-4}$alkyl, halo $C_{1-4}$alkyl, carboxy, or an additional aryl, heteroaryl or $C_{3-8}$cycloalkyl;
(xi) $R_{20}$ is H, $C_{1-4}$alkyl or $C_{3-7}$cycloalkyl;
in free or salt form.

20. The compound according to claim 2, which is the compound of Formula I-A,

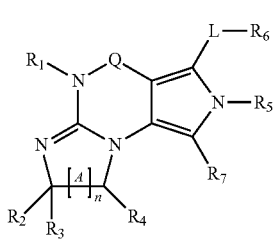

Formula I-A wherein
(i) Q is C(=O);
(ii) L is a —N(H), $CH_2$ or S;
(iii) $R_1$ is H or $C_{1-4}$ alkyl;
(iv) $R_2$ is H and $R_3$ and $R_4$ together form a di-, tri- or tetramethylene bridge;
(v) $R_5$ is attached to the nitrogen on the pyrrolo portion of Formula I-A and is a moiety of Formula A

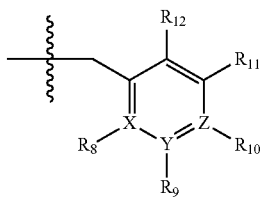

Formula A wherein X, Y and Z are, independently, N or C, and $R_8$, $R_9$, $R_{11}$ and $R_{12}$ are independently H or halogen, and $R_{10}$ is $C_{3-7}$cycloalkyl, hetero$C_{3-7}$cycloalkyl, aryl, or heteroaryl, wherein the aryl, heteroaryl, cycloalkyl or heterocycloalkyl is independently, optionally substituted with one or more $C_{1-4}$alkyl, halogen, halo$C_{1-4}$alkyl, hydroxy, carboxy, —SH or an additional aryl or heteroaryl, provided that when X, Y, or Z is nitrogen, $R_8$, $R_9$, or $R_{10}$, respectively, is not present;

(vi) $R_6$ is aryl optionally substituted with one or more halo, hydroxy;

(vii) $R_7$ is H; and (viii) n=0, in free or salt form.

21. The compound according to claim 3, wherein:
(i) Q is C(=O);
(ii) L is a —N(H)—;
(iii) $R_1$ is H or $C_{1-4}$ alkyl;
(iv) $R_2$ is H and $R_3$ and $R_4$ together form a di-, tri- or tetramethylene bridge;
(v) $R_5$ is -D-E-F, wherein:
D is methylene;
E is phenylene;
F is heteroaryl,
(vi) $R_6$ is H or aryl optionally substituted with one or more halo, hydroxy or $C_{1-6}$alkoxy;
(vii) $R_7$ is H; and
(viii) n=0,
in free or salt form.

22. The compound according to claim 3, wherein:
(i) Q is C(=O);
(ii) L is a —N(H)—;
(iii) $R_1$ is H or $C_{1-4}$ alkyl;
(iv) $R_2$ is H and $R_3$ and $R_4$ together form a di-, tri- or tetramethylene bridge;
(v) $R_5$ is -D-E-F, wherein:
D is methylene;
E is phenylene;
F is heteroaryl substituted with one or more halo, halo$C_{1-4}$alkyl or $C_{1-4}$alkyl,
(vi) $R_6$ is H or aryl optionally substituted with one or more halo, hydroxy or $C_{1-6}$alkoxy;
(vii) $R_7$ is H; and
(viii) n=0,
in free or salt form.

23. The compound according to claim 3, wherein
(i) Q is C(=O);
(ii) L is a —N(H)—;
(iii) $R_1$ is H or $C_{1-4}$ alkyl;
(iv) $R_2$ is H and $R_3$ and $R_4$ together form a di-, tri- or tetramethylene bridge;

(v) $R_5$ is -D-E-F, wherein:
D is methylene;
E is phenylene;
F is pyridyl;
(vi) $R_6$ is H or aryl optionally substituted with one or more halo, hydroxy or $C_{1-6}$alkoxy;
(vii) $R_7$ is H; and
(viii) n=0,
in free or salt form.

24. The compound according to claim 2 selected from any of the following:

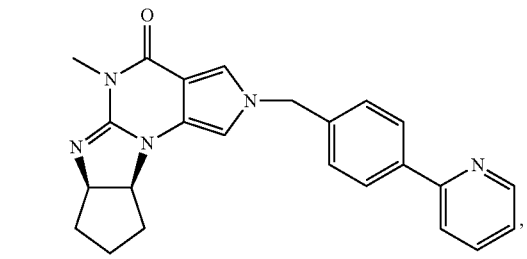

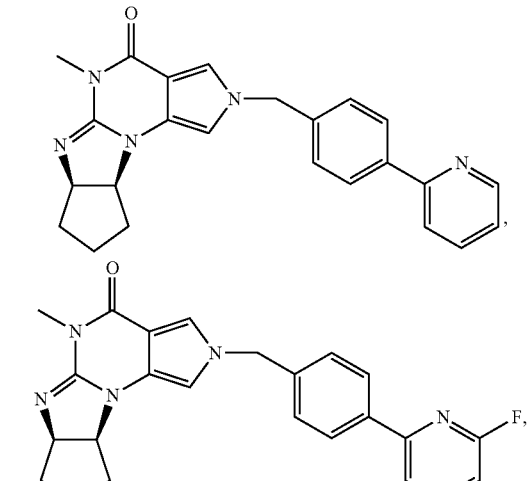

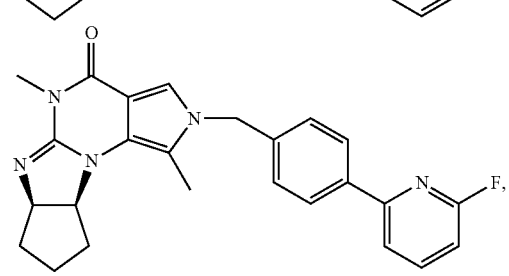

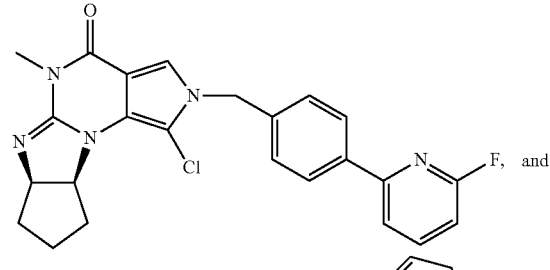

and

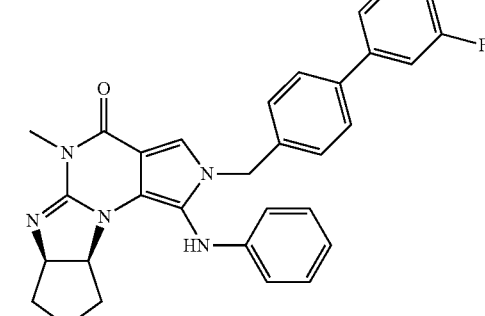

in free or salt form.

25. The compound according to claim 2 selected from any of the following:
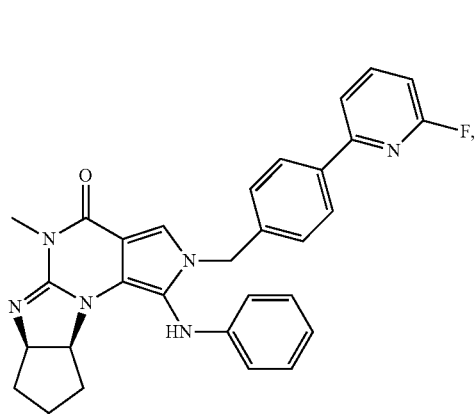
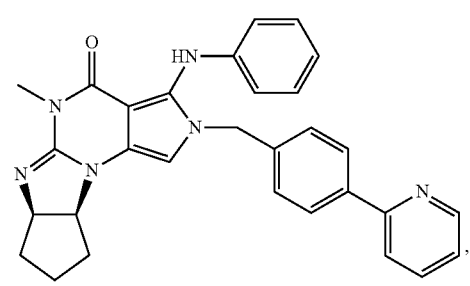
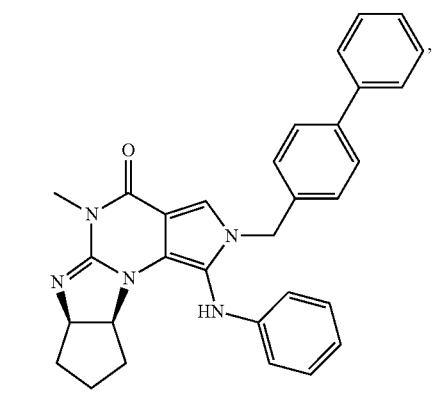
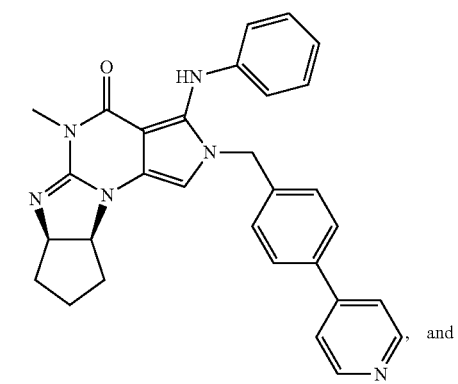
and
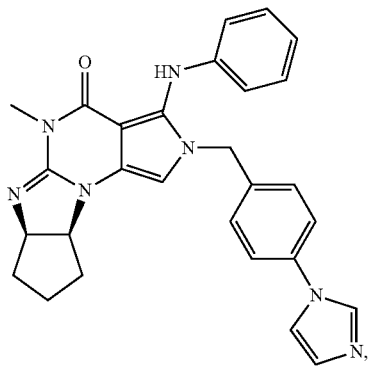
in free or salt form.
26. The compound according to claim 2 wherein the compound is:
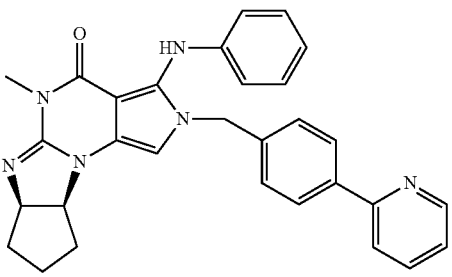 [SMILES: CN1C(=O)c2c(cn(Cc3ccc(-c4ccccn4)cc3)c2Nc2ccccc2)N2C1=N[C@@H]1CCC[C@@H]12]
in free or salt form.
27. The compound according to claim 2 wherein the compound is:
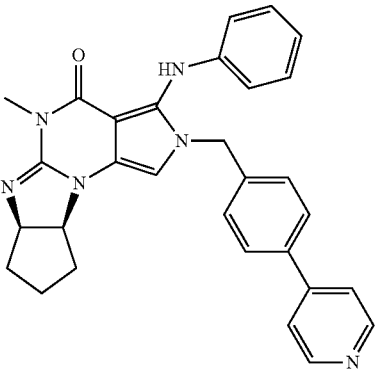 [SMILES: CN1C(=O)c2c(cn(Cc3ccc(-c4ccncc4)cc3)c2Nc2ccccc2)N2C1=N[C@@H]1CCC[C@@H]12]
in free or salt form.
28. The compound according to claim 2, which is formula I-A:
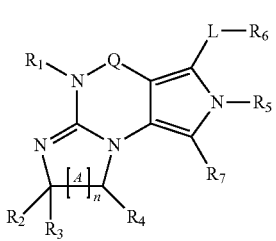
Formula I-A wherein Q is C(=O) and L is —N(H), CH$_2$ or S, R$_1$-R$_7$ are as defined in claim 2, in free or salt form.

29. The compound according to claim 2, which is the compound:

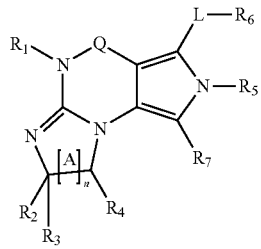

Formula I-A wherein:
(i) Q is C(=O);
(ii) L is —N(H)—, —CH$_2$— or —S—;
(iii) R1 is H or C$_{1-4}$alkyl;
(iv) R$_2$ is H and R$_3$ and R$_4$ together form a di-, tri- or tetramethylene bridge;
(v) R$_5$ is -D-E-F and D is methylene; E is phenylene; F is heteroaryl;
(vi) R$_6$ is aryl optionally substituted with one or more halo, hydroxy or C$_{1-6}$alkoxy;
(vii) R$_7$ is H; and
(viii) n=0,
in free or salt form.

30. The compound according to claim 2, wherein F is pyridyl, in free or salt form.

31. The compound according to claim 2 selected from:

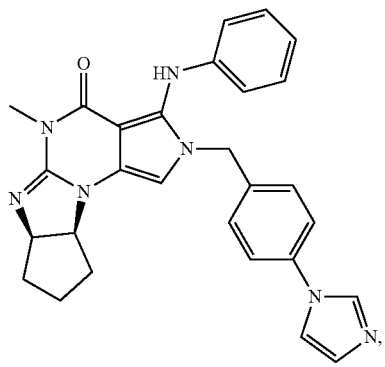

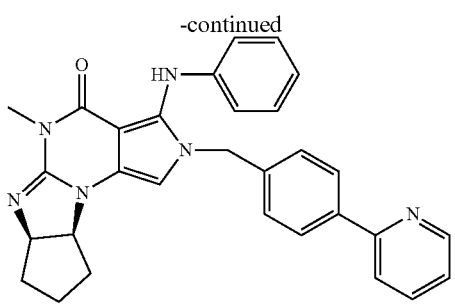

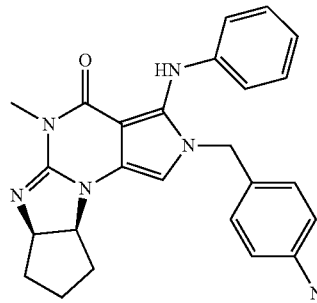 or

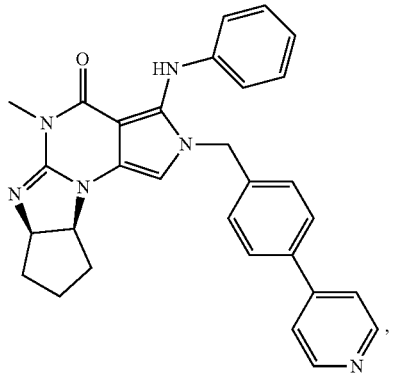

in free or salt form.

* * * * *

UNITED STATES PATENT AND TRADEMARK OFFICE
CERTIFICATE OF CORRECTION

PATENT NO. : 8,664,207 B2  
APPLICATION NO. : 13/133101  
DATED : March 4, 2014  
INVENTOR(S) : Li et al.

Page 1 of 1

It is certified that error appears in the above-identified patent and that said Letters Patent is hereby corrected as shown below:

In the Claims

Claim 2, section (v), Column 66, line 17, please insert the substituent -- -C(O)-$R_{15}$ -- between lines 17 and 18.

Claim 2, subsection (xiii), Column 67, line 35, please replace "heteroC3-8cycloalky" with "heteroC$_{3-8}$cycloalkyl".

Claim 19, subsection (v), Column 78, lines 14 - 15, please replace "R9, R9 or R10" with "$R_8$, $R_9$, and $R_{10}$".

Signed and Sealed this  
First Day of July, 2014

Michelle K. Lee  
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,664,207 B2 | Page 1 of 1 |
| APPLICATION NO. | : 13/133101 | |
| DATED | : March 4, 2014 | |
| INVENTOR(S) | : Li et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 170 days.

Signed and Sealed this
Second Day of June, 2015

Michelle K. Lee
*Director of the United States Patent and Trademark Office*